United States Patent
Naftchi

[11] Patent Number: 5,958,933
[45] Date of Patent: Sep. 28, 1999

[54] NEUROLOGICALLY ACTIVE COMPOUNDS AND COMPOUNDS WITH MULTIPLE ACTIVITIES

[76] Inventor: N. Eric Naftchi, 389 Forest Ave., Teaneck, N.J. 10170

[21] Appl. No.: 08/488,893

[22] Filed: Jun. 6, 1995

Related U.S. Application Data

[63] Continuation of application No. 08/147,150, Nov. 2, 1993, abandoned, which is a continuation-in-part of application No. 07/956,600, Oct. 5, 1992, abandoned, and application No. 07/150,767, Feb. 1, 1988, Pat. No. 4,855,325, which is a continuation-in-part of application No. 06/691,830, Jan. 16, 1985, Pat. No. 4,742,054, which is a continuation of application No. 06/443,915, Nov. 23, 1982, abandoned, said application No. 07/956,600, is a continuation-in-part of application No. 07/189,464, May 2, 1988, which is a continuation-in-part of application No. 07/150,767.

[51] Int. Cl.$^6$ .................. A61K 31/52; C07D 473/10; C07D 473/06; C07D 473/08
[52] U.S. Cl. ................. 514/263; 514/245; 514/261; 514/388; 514/395; 514/396; 514/397; 544/194; 544/197; 544/205; 544/206; 544/208; 544/267; 544/272; 544/276; 544/277
[58] Field of Search .................. 544/194, 197, 544/206, 208; 514/245, 263, 388, 395, 397, 401, 634, 635, 267, 272

[56] References Cited

FOREIGN PATENT DOCUMENTS

| | | | |
|---|---|---|---|
| 0025809 | 3/1970 | Japan | 544/197 |
| 7215245 | 11/1971 | Netherlands | 544/197 |

OTHER PUBLICATIONS

Tani et al, CA75: 36137n, 1971.

Rostyslaw, J. Org. Chem. 29(9), 2766–8, 1964.

*Primary Examiner*—John M. Ford
*Assistant Examiner*—Pavanaram K Sripada
*Attorney, Agent, or Firm*—Barry G. Magidoff; Thelen Reid & Priest

[57] ABSTRACT

A method for treating a mammal having a damaged central nervous system, as the result of trauma or disease, for reestablishing previously destroyed neurological functions in a traumatized or diseased mammal, or for controlling spasticity and for providing protection from such injury to the central nervous system. The method comprises administering to the mammal at least one neurologically active compound comprising two groups, one group providing alpha-adrenergic agonist activity, specifically a guanidino group, and the second group providing agonist activity selected from the group consisting of beta-adrenergic agonist activity, serotinergic agonist activity, and GABA-ergic agonist activity (for example a methylated xanthine group, having beta-adrenergic agonist activity) as the primary therapeutic agent. The neurologically active compound is administered in a dosage amount and at a dosage rate sufficient to at least partially restore the lost neurological function or to control spasticity.

6 Claims, No Drawings

NEUROLOGICALLY ACTIVE COMPOUNDS AND COMPOUNDS WITH MULTIPLE ACTIVITIES

This application is a continuation of 08/147,150, filed Nov. 2, 1993 now abandoned, which is a continuation-in-part of copending application Ser. No. 07/956,600, filed Oct. 5, 1992, now abandoned, which in turn is a continuation-in-part of copending application Ser. No. 07/189,464, filed May 2, 1988, which in turn is a continuation-in-part of Ser. No. 07/150,767, filed Feb. 1, 1988, now U.S. Pat. No. 4,855,325, which is a C.I.P. of Ser. No. 06/691,830, filed Jan. 16, 1985, now U.S. Pat. No. 4,742,054, which is a continuation of Ser. No. 06/443,915, filed Nov. 23, 1982, now abandoned. Ser. No. 08/147,150 filed Nov. 2, 1993, now abandoned, is a continuation in part of Ser. No. 07/150,767, filed Feb. 1, 1988, now U.S. Pat. No. 4,855,325 which is a C.I.P. Ser. No. 06/691,830, filed Jan. 16, 1985, now U.S. Pat. No. 4,742,054, issued on May 3, 1988, which was a continuation of Ser. No. 06/443,915, filed Nov. 23, 1982 abandoned.

This invention relates to a group of receptor active compounds, primarily adrenergically active, and more particularly to compounds that contain a guanidino group or an amidino group.

It has previously been recognized that a variety of guanidine derivatives have alpha-adrenergic receptor activity in vivo. A variety of guanidine derivatives have also been used clinically as anti-hypertensive agents, including clonidine, guanabenz, guanacline, guanadrel, guanazodine, guanethidine, guanfacine and guanochlor, guanoxabenz and guanoxan.

There has recently been interest in the treatment of severe spinal trauma. The treatment has resulted in reduction of the ensuing spasticity in human, and in many spinal cord injured mammals. It has also resulted in partial or complete recovery of sensory-motor control below the trauma level. Publications by the present inventor and by others, confirming by independent tests the inventor's results with the use of clonidine, a known alpha$_2$-adrenoceptor agonist, include, for example: "Functional Restoration of the Traumatically Injured Spinal Cord in Cats by Clonidine", Naftchi, N. E., SCIENCE 217, pages 1042–1044 (1982); THE PHYSIOLOGIST, Volume 27, page 220, August, 1984, "Histochemical Correlates Of Behavioral Effect of Alpha-2 Adrenergic Agonist in Spinal Rats", N. E. Naftchi, et al, and a more complete text provided in a paper given at the American Congress For Rehabilitation Medicine, 61st Annual Session, October 23, 1984, "Newer Research in Spinal Cord Injury, Mechanism and Prevention of Acute Spinal Cord Injury" "Treatment of Mammalian Spinal Cord Injury With Antioxidants", by N. Eric Naftchi, INT. J. DEVL. NEUROSCIENCE, vol. 9, No. 2, pp 113–126 (1991).

Clonidine and guanabenz, both alpha$_2$-adrenergic receptor agonists used in the earlier work, had limited usefulness because long-term treatment with these two agents resulted in the sedation, sleepiness and desensitization of the subjects. In addition to these side effects, these agents also cause hypotension and syncopy, which tend to reduce mobility and thus delay rehabilitation and recovery of the spinal cord injured subjects. Further other side effects include constipation and rectal impaction which in tetraplegic subjects and paraplegic subjects with lesions above thoracic sixth vertebrae can paradoxically result in severe hypertension, a syndrome known as autonomic hyperreflexia.

This application further relates to new anesthetic and hypothermic agents, and more particularly to the use as general anesthetic and/or hypothermic agents, in mammals, of a previously known pharmacologic compound, guanabenz and certain of its related compounds ("guanidino compounds"). When both properties, anesthesia and hypothermia are found in the same compound, its administration results in pseudo-hibernation, that results in a relatively bloodless operating field, which can be beneficial when undergoing major surgery. These guanidino compounds also have other valuable pharmocologic properties.

Guanabenz has long been used in clinical pharmacology, generally by oral administration, as an antihypertensive agent. It is known to be a stimulant, or agonist, of central alpha$_2$-adrenergic receptors, resulting in a decrease of sympathetic outflow from the brain at the bulbar level to the peripheral circulatory system.

Among the known "adverse effects" of guanabenz as an antihypertensive agent are sedation, anxiety, ataxia, depression, and sleep disturbances. Although most prior clinical use of guanabenz has involved oral administration, earlier parenteral testing in dogs had produced natriuresis, thus contraindicating long-term administration by this route for hypertension treatment.

Accidental oral overdosages of guanabenz, have not been reported to result in anesthesia; the incidents were recorded as hypotension, somnolence, lethargy, irritability, myosis and bradycardia in young children.

In U.S. Pat. No. 4,060,640, Kodama et al., described guanabenz, and its related compounds, as being central nervous system depressants that reduced hyperexcitability and induced sedation, thus overcoming psychic depression.

This alpha-adrenoceptor agonist has been shown to have a restorative effect on the central nervous system, especially in the treatment of motor and sensory functional losses due to the traumatic injury to the spinal cord (see U.S. Pat. No. 4,742,054).

GENERAL DESCRIPTION OF THE INVENTION

I. Sensory-Motor Function Restoration

It is an object of the present invention to provide novel compounds which have the capability of restoring to a mammal maximal sensory-motor function following damage to the central nervous system caused by trauma or disease. It is a further object of the present invention to provide novel compounds having such capability but without undesirable side effects which would interfere with the treatment of any mammal having suffered traumatic central nervous system injury.

A further objective of the invention, the novel compounds are efficacious anti-spastic, or spasmolytic, agents that control spasticity caused as a result of neurological damage. These drugs would also produce little or no sedation or somnolence and would not drastically lower blood pressure.

II. Anesthesia and Hypothermia

Guanidino compounds, among the alpha-adrenergic receptor agonists, are capable of inducing profound anaesthesia and/or hypothermia in mammals, when administered in a sufficient unit dosage, i.e., at least about 3 mg/kg in rats and 0.05 mg/kg in primates. In order to expedite and render more efficient the onset of anesthesia, guanabenz is preferably administered intraperitoneally (I.P.), or intravenously (I.V.), in the usual liquid vehicles, e.g., preferably a 5% aqueous dextrose solution. The guanidino compound can be provided in any of the usual pharmaceutical forms, e.g., as a physiologically acceptable salt, such as guanabenz acetate, guanabenz HCl, guanabenz maleate, or guanabenz sodium succinate, dissolved in, e.g. a 5% aqueous dextrose solution. As guanabenz and others of these guanidino compounds are capable of passing through the blood-brain barrier, unlike many non-volatile anesthetics, they need not be administered intrathecally.

The term "guanidino compounds" for both groups of activities includes any compound which has adrenergic receptor activity and which is sufficiently lipophilic to pass the blood-brain barrier in the central nervous system; and which include the moiety:

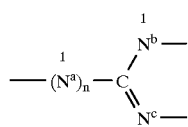

I.

in which "n" can be an integer from 1 to 3. The above moiety can be a branched acyclic group as shown above, or the atoms "C", $N^a$, "$N^b$" or "$N^c$" can be part of a cyclic group, for example, an imidazolino, a benzimidazolino, a melamine (or triazine) group, an amino-1,3-diazacyclopentene-(2), aminocaffeine, an amino-1,3-diazacyclohexene-(2), or 3,5-Diamino-1,2,4-triazole.

This guanidino moiety can be part of a xanthine group, such as in 8-aminocaffeine, or a separate group linked with a xanthine group, such as by reacting a guanidino compound with theophylline-7-acetic acid, which product possesses alpha and beta adrenergic activity. When the moiety is combined with, i.e., 5-OH-tryptamine-3,4-dihydroxyacetaldhyde, gamma-aminobutyric acid, or choline, the resulting compound, in addition to alpha adrenoceptor activity, possesses serotonergic, dopaminergic, GABA-ergic, or cholinergic activities, respectively.

In the guanidino group of Formula I, above one of $N^a$, $N^b$ or $N^c$ can be replaced with a sulfur or oxygen atom, i.e., —S—, or —O—, and also obtain the desired agonist activity. When one of $N^a$, $N^b$ or $N^c$ is replaced by a carbon atom (—C—), the resulting compound containing the group has an alpha-adrenergic antagonist activity, e.g., will reverse hypothermia or anesthesia induced by guanabenz, such as exemplified by compounds Nos. 96–101, 162, 163, 192, in Table I, below. These adrenergic antagonist compounds are also neuroprotective and, similar to guanidino compounds, possess glutamate (NMDA) receptor antagonistic activities.

DETAILED DESCRIPTION OF THE INVENTION

In accordance with the first aspect of the present invention, there are provided pharmacologically active compounds having the capability of reestablishing previously nonfunctioning or dysfunctioning, or destroyed neurological functions in a traumatized or diseased mammal. These compounds comprise the reaction products of a guanidino, aminoguanidino, 2-imidazolino, 2-hydrazinoimidazolino, 2-guanidinobenzimidazolino, 3,5-diamino-1,2,4-triazole and the like groups with a methylated xanthine group, which provide a combination of receptor activity designed to stimulate appropriate receptors in the brain and spinal cord and thereby reestablish the lost negative feedback and thereby tonically stimulate sensory and motor neurons, in spite of a severely damaged central nervous system. These compounds are highly lipophilic and thus capable of crossing the blood/CNS barrier and they preferably have the following general formula:

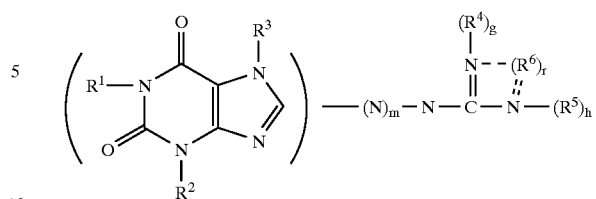

A.1

Wherein g and r can have a value of 0 or 1, to a total of one, h can be 0, 1 or 2, and n is 0 or an integer of at least 1 and preferably not greater than 2; the R groups can be hydrogen or non-interfering organic groups. $R_1$ and $R_2$ and $R_3$ preferably include alkyl groups or hydrogen atoms, at least one of $R_1$ and $R_2$ and/or $R_3$ most preferably comprising an alkyl group. $R_1$ and/or $R_3$ can be the bridging group to the guanidino moiety outside of the brackets, and can be an aliphatic group, saturated or unsaturated, preferably including a carboxyl group or a carbonyl group, oxygen, nitrogen, sulfur, connected to a nitrogen atom of the guanidino group by a double bond. Thus $R_1$ and $R_3$ can preferably include acetyl, acetaldehyde, propionyl, hydroxyalkyl. $R_4$ and $R_5$ can each be hydrogen, or any non-interfering organic group, preferably including lower alkyl, alkoxy, thioalkyl, alkenyl, aryl, aralkyl, or alkaryl or a nucleoside group, or any such group substituted with $NH_2$, OH, $OCH_3$, or halogen, sulfur, oxygen, or $NO_2$, $R_6$, if present, is a bridging group forming a closed heterocyclic ring compound with the two nitrogen atoms on the guanidino group, and can be any non-interfering organic group, which can include additional nitrogen atoms, halogen atoms, oxygen atoms, and can be aliphatic, cycloaliphatic, or aromatic, so as to form groups such as, e.g., imidazole, benzimidazole, triazine, thiopyrimidine, triazolethiol, diphenyl-2-imidazole-thiol.

The novel compounds of the present invention have an alpha$_2$-adrenergic receptor agonist moiety and a beta-adrenoceptor agonist moiety. Preferably, the beta-receptor agonist moiety (within the brackets) is derived from a compound that has an indirect beta-adrenergic effect, such as the substituted xanthines, which enhance the metabolic effect of cyclic adenosine 3',5'-monophosphate (c-AMP), by blocking c-AMP phosphodiesterase. These xanthines further enhance microcirculation within the muscle mass by increasing local vasodilation.

The present invention builds upon the effects noted in the earliest parent application hereto by combining in a single compound or complex the effects of the alpha$_2$ and beta agonists.

As was noted during the earlier work, the previously known alpha$_2$-adrenergic receptor agonists ("alpha$_2$-agonists"), have other direct physiological effects on the mammal being treated, which often are contraindicated following trauma, such as spinal injury, e.g., the hypotensive effect of clonidine and guanabenz. It was recognized that such undesirable side effects can be counteracted by the simultaneous or sequential administration of an antagonist or a pressor agent, such as angiotensin II which could be titrated against the alpha$_2$-agonist. Usually, it was extremely difficult to avoid any such hypotensive effect, or some time serious hypertensive effects. The compounds of the present invention, which include the guanidino, 2-amino-imidazolino, 2-hydrazino-imidazolino, 2-guanidinobenz-imidazolino, 3,5-Diamino-1,2,4-triazolino, or 2,3,5-s-triazine moiety, as the alpha$_2$ agonist, plus a beta-agonist moiety, avoid severe hypotensive effect, and result in an improved reactivation and reestablishment of the descending monoaminergic pathways and ascending nociceptive pathways while also improving upon and speeding up the affirmative process of restoring motor and sensory functions to almost one/third of the time required by the alpha$_2$ agonists.

The indirect beta-agonists, such as substituted xanthines, act by inhibiting the enzyme c-AMP phosphodiesterase, with the effect of increasing the ratio of c-AMP to c-GMP (cyclic guanosine-3',5'-monophosphate). In addition, moieties derived from direct acting beta-agonist, such as 4-hydroxy-3-methoxymandelic acid, 3,4-dihydroxymandelic aldehyde, 3,4-dihydroxyphenyl(beta-hydroxy)-acetaldehyde may be combined through their aldehyde or carboxyl groups with guanidine, aminoguanidine, etc. to yield internally neutralized compounds which have similar effect.

Referring to Formula 1, the xanthine group is connected to the guanidino group through one of the guanidino-nitrogen atoms.

In addition, it has been found that similar effects can be obtained when in the guanidino moiety, one of the nitrogen atoms in the guanidino group shown in Formula 1 is replaced by a sulphur or an oxygen atom.

Typical species of this class of mixed agonist compounds are set out in the working examples below, as well by the following list:
A1. Guanidino-7-Acetyltheophylline
A2. 2-Guanidinobenzimidazolyl-7-Acetyltheophylline
A3. 3,4,5-Trimethoxybenzylidene-2-Hydrazinoimidazole
A4. 2-Hydrazinoimidazolyl-7-Acetyltheophylline
A5. Theobromine-1-Acetyl Guanidine
A6. Theophylline-7-Acetylamidoguanidine
A7. Theobromine-1-Acetylamidoguanidine
A8. Theophylline-7-Acetyliminoguanidine
A9. 2,4,6-Tris(7-Acetamidotheophylline)-1,3,5-s-Triazine
A10. 2,4-Bis(2,6-Dicholorbenzylideneimino)-6-(7-Acetamidotheophylline)-1,3,5-s-Triazine
A11. 2,4-Bis(1-Naphthylacetamido)-6(7-Acetamidotheophylline)-1,3,5-s-Triazine
A12. 2,4-Bis(7-Acetamidotheophylline)-6-(2,6-Dichlorobenzylideneamino)-1,3,5-s-Triazine
A13. Theophylline-7-Ethyleneiminoguanidine Other such mixed agonist compounds are exemplified by the 8-amino caffeine compounds, such as cafaminol, or compounds numbered 191, 197, 203, 205, 209, 213–215 in Table II, below. In such compounds, the guanidino group, in part, is formed as part of the xanthine group by substituting an amino group onto the eighth position of the xanthine group. One method of preparing these compounds is shown in U.S. Pat. No. 3,094,531.

With mixed agonist or agonist-antagonist properties, the compounds of the present invention can be used as medicaments for mammals in the form of pharmaceutical preparations suitable for administration orally, parenterally, intraperitoneally, intravenously or as nasal spray. These compounds can be administered in a substantially pure form, with other active ingredients which may be desirable, or merely with a suitable pharmaceutical vehicle. The compounds are generally crystalline solids which may be at least partially soluble in commonly used organic salts. They are also generally soluble in liquid pharmaceutical vehicles, including water. Generally, the compounds can be formed as physiologically acceptable salts including the salts of inorganic acids, such as hydrochloric, hydriodic, sulfuric or phosphoric, as well as organic acids including acetic, malic, ethionic, malonic, citric, benzoic and pamoic. Generally, these acid addition salts are more soluble in water than the compounds per se. Formulation in a pharmaceutical vehicle can be carried out in accordance with techniques and in vehicles which are wholly conventional to those skilled in the art for the intended mode of administration.

For example, preparations for oral administration can be in either liquid or solid form, including for example syrups, elixirs, powders, capsules or tablets. The materials are preferably prepared for unit dosage form as powders which are preferably pressed into tablets or suitably encapsulated in, for example, conventional gelatine capsules. Any powders or compressed tablets can generally also comprise the usually suitable excipients and/or diluents, such as starch, lactose, stearic acid, magnesium stearate, dextrin or polyvinylpyrrolidone.

Other suitable solid carriers include magnesium stearate, sicaryl alcohol, talc, vegetable oils or fats, alcohols such an benzyl alcohols, gums, waxes, alkylene or polyalkylene glycols, such as propylene glycol or polypropylene glycol and any other well known carriers.

Suitable sterile solutions or suspensions can be prepared for parenteral or intraperitoneal administration, e.g., intravenous, containing for example water, physiological saline, benzyl alcohol, ethyl oleate, methylcellulose, dimethyl sulfoxide, polyethylene glycol liquid, as well as other liquid excipients well known in the pharmaceutical or veterinary art. Other auxiliary pharmaceutical materials which can be present include preservatives, stabilizers, wetting or emulsifying agents, or osmotic salts or buffering agents, as is well known to the pharmaceutical or veterinary art. As these formulations are generally well known and conventional, more specific instructions need not be presented for purposes of defining this invention.

As stated, the mixed alpha/beta receptor active compounds of the present invention are most effective in treating the undesirable after-effects of traumatic spinal injury, including even transection of spinal cord. Restoration of at least some normal sensory and motor control can be obtained as a result of treatment, especially if carried out within a relatively short time after injury to the spinal cord.

Because the compounds of the present invention do not have many of the undesirable side effects of utilizing the prior alpha$_2$-adrenoreceptor agonists of the parent application, it is not necessary to postpone treatment using these novel compounds until after stabilization of the vital signs and recovery from the initial shock. Indeed, many of these compounds are also effective in treating the initial shock conditions by way of stabilizing or even slightly elevating arterial blood pressure and improving microprofusion pressure in the area of injury. Thus, the compounds of the present invention have positive hemodynamic effect as well as positive neurological effects.

In all cases, as explained in the earlier work, it is necessary to insure, by taking active surgical steps, if necessary, to remove any mechanical obstruction and compression pressure as created by crushed bone, growth of scar tissue or connective tissue or any other mechanical cause, especially in chronic spinal cord injured mammals.

The mixed agonists of this invention also have been found to interfere with the formation of undesirable scar tissue at the trauma site. It is believed that these mixed agonists interfere with triple helix formation in the synthesis of collagen protein, thus preventing or reducing the formation of hard scar tissue at the trauma site.

During treatment using the compounds of the present invention, it is greatly preferred that the plasma level of the compound in the blood stream of the mammal being treated be maintained as constant as feasible. This is especially important with respect to spinal injuries in order to reduce or substantially eliminate autonomic dysreflexia and spasticity during treatment until permanent return of sensory and motor function has been obtained. These compounds generally should be administered in a proportion of at least about 10 mcg/kg of body weight, and preferably in an amount of at least 15 mcg and preferably not more than about 100 mcg/kg of body weight, and most preferably not more than about 70 mcg/kg of body weight. However, it has been found that the optimal proportion in the blood is not directly proportional to body weight, but rather to a combination of factors including body weight and body superficial area.

It may be preferable to administer these novel pharmacological agents using a sustained release form, for example, the conventionally available sustained release capsules or sustained release transdermal products. Alternatively, if it is not feasible to utilize the sustained release forms, these novel compounds can be administered regularly at relatively short intervals, for example, 2 to 4 times per day. Although not as desirable for chronic long-term treatment, these compounds can, at least initially after the trauma, be administered intraperitoneally or intravenously to maintain a constant, tonic effect by slow administration of medication, or as a single injection, at intervals.

An additional effect of the present novel compounds, especially important in the immediate aftermath of traumatic injury and shock, is the immediate stimulation of spinal cord motor neurons, which keeps the muscle mass from wasting, preventing loss of weight and demineralization of the skeleton, all of which are common occurrences after spinal cord trauma. In addition, by avoiding constipation, as is often caused by pure alpha$_2$ agonists, extreme hypertension and autonomic hyperreflexia are also avoided. Further, since the compounds are relatively internally neutralized with respect to c-AMP and c-GMP, receptor supersensitivity will be greatly minimized.

Most of the novel compounds of the present invention in accordance with Formula IA above, can be prepared by reacting a first compound ("A") which contains a guanidino group and which can be present as part of a heterocyclic group, e.g., an amino triazine group, an amino arylimidazole, an amino benzylimidazole, or an aminoimidazoline group, or an equivalent thio compound where one of the nitrogen atoms forming any of the above groups is replaced by a sulphur atom, with a second compound ("B") comprising a direct or indirect beta-adrenergic receptor agonist, such as a substituted xanthine or analogs of beta-hydroxyphenyl acetic acid, aldehyde or amine. Each of the above A and B compounds preferably include one of a carbonyl group (such as a carboxyl group or an aldehyde group), a hydroxyl group or an amino (—NH$_2$), which are mutually reactive. Most preferably, the "A" compound reacts through a primary or secondary amino nitrogen atom forming part of the guanidino or aminoguanidino moiety.

Suitable group A compounds include guanidine, aminoguanidine, 2-guanidinobenz imidazole, 2-aminoimidazole, 2-aminodihydrothiazine, 2-hydrazinoimidazoline, 2,4,6-triamino-1,3,5-s-triazine, 2,4-diamino-6-phenyl-1,3,5-s-triazine, 2,4-bis(diethylamino)-6-hydrazino-1,3,5-s-triazine, 4-methyl-4H-1,2,4-triazole-3-thiole, 4,5,diphenyl-2-imidazole-thiole, 2-(4-aminophenyl-6-methyl-benzothiazole), 3,5-diamino-1,2,4-triazole, 8-aminocaffeine and their acid addition salts. The 8-aminocaffeine compound can be prepared, e.g., by reacting 8-chlorocaffeine with ammonia.

Useful B group compounds which are preferably direct or indirect beta-agonists, can be, for example, theophylline, etofylline, theophylline-7-acetic acid, theophylline-7-acetaldehyde, 7-(2,3-dihydroxy)-propyltheophylline, 1-theobromine acetic acid, 1-theobromine acetaldehyde. Alternatively, 8-chlorocaffeine can be reacted with compounds having a free amino-group, to form the third leg of the guanidino group, or to form a biguanide by reacting 8-chlorocaffeine with, e.g., aminoguanidine, or 2-hydrazinoimidazole.

The following examples provide common procedures for preparing species which are preferred for their activity with respect to the treatment of damage to the central nervous system, utilizing the group of reactants to obtain final products containing both alpha- and beta-adrenergic activity, in accordance with one aspect constituting the present inventions. These procedures are similar to methods commonly used in the preparation of complex organic chemicals. These illustrative compounds within the present invention may, of course, also be prepared by other paths.

In each example, the final product is designated by a capital letter, to provide a shorthand identification for the compound in subsequent portions of this text.

EXAMPLE 1

Preparation of Guanidino-7-Acetyltheophylline(C)

Theophylline-7-acetic acid (TAA) (0.42 moles, 100 grams) is admixed with excess thionyl chloride (SOC12) and slowly heated to 45° C. and refluxed for 2 hours. When reaction is completed, the excess SOCl2 is removed under vacuum evaporation at 50° C., in the presence of benzene (80 grams). The vacuum evaporation with benzene is repeated three times to eliminate all residual SOCl2. The resultant compound, theophylline-7-acetyl chloride ("TAC") is added to a solution of guanidine hydrochloride (0.25 mols, 60 grams) and 5 equivalents of 2 normal sodium hydroxide at 0° C.

The mixture is stirred vigorously for thirty (30) minutes until a precipitate is completely formed. The resultant yellow precipitate is filtered out by Whatman No. 1 filter paper; the filtered solid is admixed with water and the pH reduced to 8 by the addition of HCl. The aqueous solution is again vacuum evaporated at 25° C., and the resultant dry yellow solid is dissolved in an alcohol solution of 80% ethanol and water and recrystalized.

The resultant product has a molecular weight of 280.26 and has the formula shown in Table IIA.

TABLE IA

| | COMPOUND ABBREV. | A | B | MOLAR RATIO A:B | PRODUCT |
|---|---|---|---|---|---|
| 1. | C | GUANIDINE, HCl | THEOPHYLLINE-7-ACETIC ACID | 1:1 | GUANIDINO-7-ACETYLTHEOPHYLLINE |
| 2. | D | 2-GUANIDINOBENZ IMIDAZOLE | THEOPHYLLINE-7-ACETIC ACID | 1:1 | 2-GUANIDINOBENZIMIDAZOLYL-7-ACETYLTHEOPHYLLINE |
| 3. | E | 2-HYDRAZINOIMIDAZOLINE,HBR | THEOPHYLLINE-7-ACETIC ACID | 1:1 | 2-HYDRAZINOIMIDAZOYL-7-ACETYLTHEOPHYLLINE |
| 4. | F | GUANIDINE | 1-THEOBROMINEACETIC ACID | 1:1 | THEOBROMINE-1-ACETYL GUANIDINE |
| 5. | $C_2$ | AMINOGUANIDINE | THEOPHYLLINE-7-ACETIC ACID | 1:1 | THEOPHYLLINE-7-ACETYLAMIDO-GUANIDINE |
| 6. | G | AMINOGUANIDINE | 1-THEOBROMINEACETIC ACID | 1:1 | THEOBROMINE-1-ACETYLAMIDO-GUANIDINE |
| 7. | N | AMINOGUANIDINE | THEOPHYLLINE-7-ACETALDEHYDE | 1:1 | THEOPHYLLINE-7-ETHYLENEIMINO-GUANIDINE |
| 8. | $C_4$ | GUANIDINE | THEOBROMINE-7-ACETALDEHYDE | 1:1 | THEOBROMINE-7-ETHYLENE-GUANIDINE |
| 9. | | GUANIDINO-ACETIC ACID | 7-(2,3-DIHYDROXY) PROPYL THEOPHYLLINE | 2:1 | 7-(2,3-DIGUANIDINOACETATE) PROPYLTHEOPHYLLINE |
| 10. | H | 2,4,6-TRIAMINO-s-TRIAZINE | THEOPHYLLINE-7-ACETIC ACID | 1:3 | 2,4,6-TRIS(7-ACETAMIDOTHEOPHYLLINE)-1,3,4-s-TRIAZINE |
| 11. | J | 2,4,6-TRIAMINO-s-TRIAZINE | 2,6-DICHLOROBENZALDEHYDE + THEOPHYLLINE-7-ACETIC ACID | 1:2:1 | 2,4-BIS (2,6-DICHLOROBENZYLIDENEIMINO)-6-(7-ACETAMIDOTHEOPHYLLINE)-1,3,5-s-TRIAZINE |
| 12. | K | 2,4,6-TRIAMINO-s-TRIAZINE | 1-NAPHTHYLACETIC ACID + THEOPHYLLINE-7-ACETIC ACID | 1:2:1 | 2,4-BIS(1-NAPHTHYLACETAMIDO)-6-(7-ACETAMIDOTHEOPHYLLINE)-1,3,4-s-TRIAZINE |
| 13. | L | 2,4,6-TRIAMINO-s-TRIAZINE | 2,6-DICHLOROBENZALADEHYDE + THEOPHYLLINE-7-ACETIC ACID | 1:1:2 | 2,4-BIS(7-ACETAMIDOTHEOPHYLLINE)-6-(2,6-DICHLOROBENZYLIDENEAMINO)-1,3,5-s-TRIAZINE |
| 14. | | 2,4,6-TRIAMINO-s-TRIAZINE | THEOPHYLLINE-7-ACETIC ACID 1-THEOBROMINEACETIC ACID | 1:1:1 | 2-(7-ACETAMIDOTHEOPHYLLINE)-4-(1-ACETAMIDO-THEOBROMINE)-6-AMINO-1,3,4-s-TRIAZINE |
| 15. | | 4,5-DIPHENYL-2-IMIDAZOLETHIOLE | THEOPHYLLINE-7-ACETIC ACID | 1:1 | THEOPHYLLINE-7-ACETYL-2-(4,5,-DIPHENYL)-2-THIOMIDAZOLE |
| 16. | | 2-(4-AMINOPHENYL)-6-METHYL-BENZOTHIAZOLE | 1-THEOBROMINEACETIC ACID | 1:1 | 1-THEOBROMINEACETYL-2-(4-AMINOPHEHYL)-6-METHYLBENZOTHIAZOLE |

TABLE IIA
1. 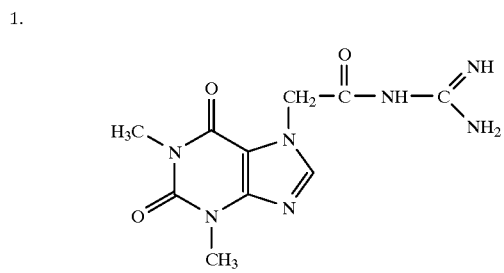
2. 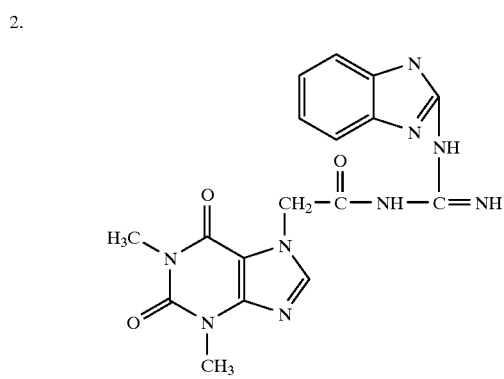
3. 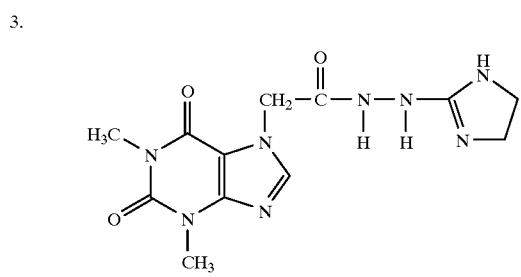
4. 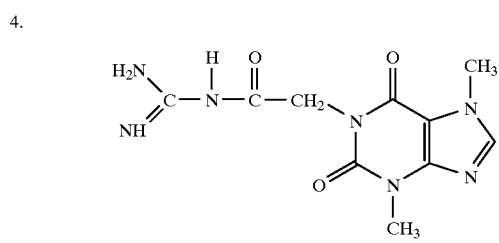
5. 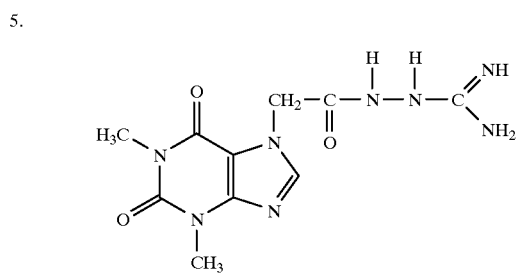
TABLE IIA-continued
6. 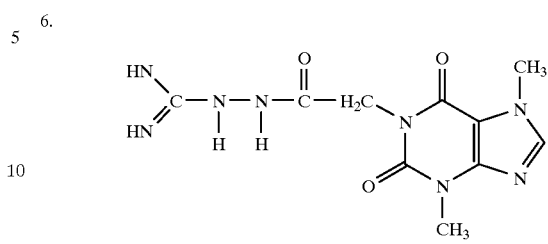
7. 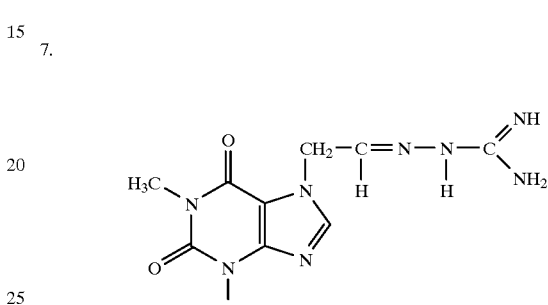
8. 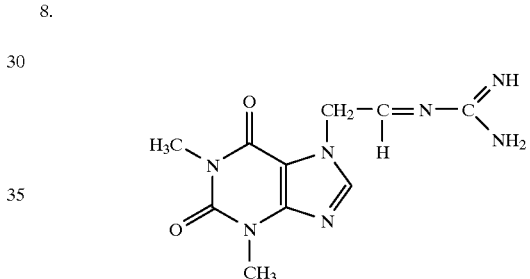
9. 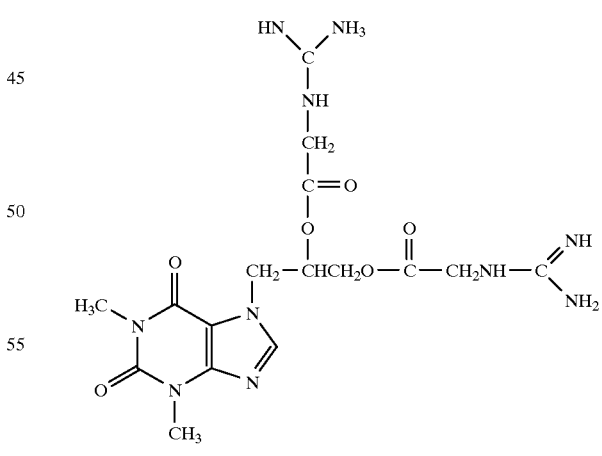

TABLE IIA-continued

10.

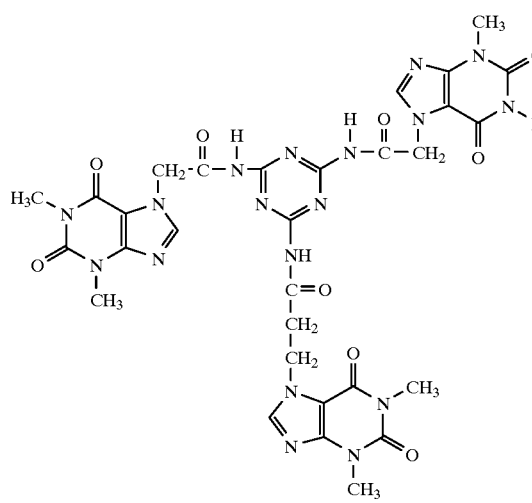

11.

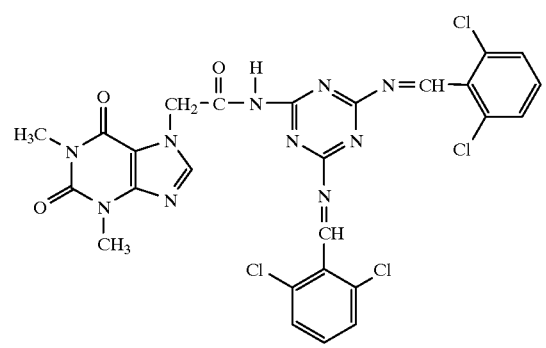

12.

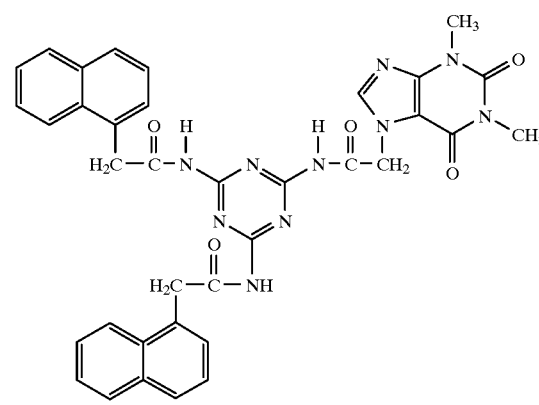

TABLE IIA-continued

13.

14.

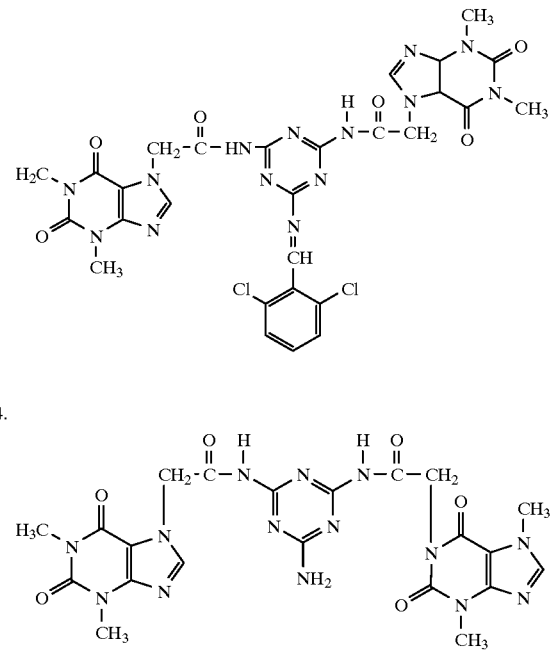

EXAMPLE 2

Preparation 2-(Theophylline-7-acetamido)-2-iminobenzimidazole(Compound D)

The acylchloride of TAA is obtained by following the same procedure in EXAMPLE 1 above. The TAC (100 g.) is then added dropwise to a solution of 2-guanidinobenzimidazole(GBI) (74 grams) in a mixture of benzene and pyridine (which is active both as a catalyst and to neutralize the by-product hydrogen chloride).

The reacting mixture is held overnight at room temperature (21° C.); the benzene layer is then separated by decanting and washed with an aqueous solution of 2 Normal HCl (to remove any excess pyridine), subsequently washed with an aqueous solution of 2 Normal sodium hydroxide, and washed again with pure deionized water, until reaching neutral pH (pH 6.8–7.2).

The benzene solution is then dried under vacuum (at 25° C.) and the resultant solid is dissolved and recrystalized from an aqueous solution of 80% ethanol. The product has a molecular weight of 394.4 and has the formula shown in Table IIA, above.

EXAMPLES 3–14

Additional Preparations

Following the same procedures as in Examples 1 and 2, additional compounds can be prepared by reacting the reagents to form the compounds as indicated in Table IA, above.

Biological Activity

The novel compounds of the present invention have been tested and found to be extremely effective in treating severe neurological disorders of the type resulting from either severe traumatic injury to the spinal cord or from systemic diseases such as multiple sclerosis. These compounds are believed to act upon receptors at several sites. The stimulating of the receptors in the spinal cord, either directly or indirectly, tonically stimulates the motor neurons, thus preserving muscle mass. These drugs generally have long-term ameliorative effects, which apparently bring about a reorganization within the nervous system, providing for regaining of central nervous system control over lost functions in those portions of the body distal to the brain and below the damaged spinal cord site. These compounds reduce spasticity and their chronic use results in control over distal body functions, for example, over the activity of the urinary tract or the legs. Also significantly, the desirable results are obtained without sedating or lowering the blood pressure of the mammal.

In the following examples, specific methods of administration are described. However, unless otherwise stated, similar response can be elicited by following other means of administration.

Comparative Example A

A cat was anesthetized using intravenous pentobarbital (30 mg/kg) after which its arterial blood pressure was continuously monitored for at least two hours. After recording stable arterial blood pressure, a dorsal laminectomy was performed in the thoracic region of the cat from T3 to T5; after restoration of blood pressure, the cat was traumatized by means of a twenty gram weight being dropped from a height of twenty-five centimeters (500 g-cm force) on the exposed dura of the spinal cord at the fourth thoracic segment.

The cat was not thereafter treated except to surgically clean the trauma region and assist in the healing of the surgery.

The cat was regularly observed over a four month period.

Somatosensory-evoked potentials (SEPs) were measured and recorded for this cat, immediately before the spinal trauma, 10, 20 and 30 minutes after the trauma, and two hours after the trauma, and then again 30 days after the trauma. The SEPs were generated by stimulating the sciatic nerve by means of needle electrodes inserted through the posterior thighs. It is known that the recording of SEPs from the somatosensory cortex by stimulating lower extremities requires the presence of intact ascending pathways. The absence of SEPs indicates a complete disruption of the spinal cord tracks. Beginning 10 minutes after impact, the SEP was substantially completely absent from the injured cat.

The cat did not regain the use of its lower extremities, nor did it ever regain bladder and bowel control. The animal progressed from acute, flaccid phase to chronic, spastic and autonomically dysreflexic phase of paralysis.

Comparative Example B

The spinal cord of a group of rats was completely transected. After surgery, the rats were treated with guanabenz. A solution of 4.0 milligrams per milliliter of 5% dextrose in water solution was prepared 72 hours after the lesion, guanabenz (0.65 mg/kg; I.P.) was given twice per day intraperitoneally.

Following each administration of the guanabenz rats became sedated for at least 2 to 4 hours. The rats presented with a condition of bloody eyes and nose for a period of 2 to 5 days after the transection. During the first two-weeks, proper plantar placement, weight bearing on the hind limbs and/or coordinated walking was not present. However, by the third week of such treatment, proper plantar placement, weight bearing on the hind limbs and walking movements of the hind limbs coordinated with those of the front limbs were observed in a majority of the rats to a satisfactory degree. The rats, however, showed some, but not significant loss of muscle mass in their hind limbs.

Working Example 1

In a further group of six rats the spinal cord was transected in accordance with the above Comparative Examples. After surgery and cleaning and mechanical treatment of the wounds in the same fashion, an intraperitoneal injection of 7-(guanidino-acetyltheophylline ("C") was administered at a dose of 5.0 mg/kg 24 hours post surgery. Within a 7 to 9 day period, the rats engaged in walking movements of the hind limbs coordinated with those of the front limbs and the hind limbs, including proper plantar placement and full weight bearing on the hind limbs.

Within 36 hours after the spinal cord transection, i.e., only 12 hours after initial administration of Compound C, the initial bloody eyes and nose condition had abated. The muscle mass was not reduced significantly and the animals regained reflex activities much faster than control rats. During the entire course of treatment, the animals did not exhibit any signs of sedation or lethargy. Further the animals were alert and continued to eat in substantially normal quantities.

Starting 24 hours post-transection, immediately after each intraperitoneal administration of Compound C, reflexes such as the tail-flick and cross-extension would return, within 12 minutes post injection. This short-term strong response was observed for at least 1½ hours after each injection and gradually diminished until subsequent readministration of Compound C, guanphylline. Within 8 to 11 days the response became sustained, and was accompanied by long-term therapeutic restoration of coordinated movements, plantar placements and weight-bearing by the hind limbs.

Three weeks after discontinuance of the treatment with Compound C, the condition of the animal remained extremely stable and the animal clearly had greater control over his movements than those treated with guanabenz, whereas the control rats of Comparative Example A were substantially incapacitated.

None of these rats treated with Compound C developed any spasticity within six months of trial after the spinal cord transection.

Measurement of blood pressure in the cat and sheep showed a slight increase immediately after administration of Compound C, which returned to basal level within 10 minutes.

Working Example 2

It was noted that some of the untreated rats in Comparative Example A developed severe spasticity three weeks after transection. Treatment of three of these control rats with guanphylline (Compound C), intra-peritoneally for 7 days, (4.0 mg/kg BID), resulted in a marked decrease in spasticity within 4 days and a complete elimination after 7 days. None of the rats initially treated with the Compound C developed spasticity at any time.

Working Example 3

Ten cats were spinally traumatized in accordance with the procedure set forth above in Comparative Example A. Five of these spinal cats were treated with Compound C commencing three hours after trauma and five of the cats were treated with guanabenz beginning at the same time. The cats treated with guanabenz (0.65 mg/kg bid) exhibited tight urinary sphincter and dyssinergia during urodynamic examination four to five weeks after treatment began. Those cats treated with the same quantity of Compound C during the same period had substantially completely recovered urinary bladder function and exhibited little or no dyssinergia after only seven to twenty-one days of treatment.

Spinalized cats required eight weeks of treatment with guanabenz before regaining controlled micturition. Cats treated with Compound C, required only three to five weeks of treatment to achieve the same results.

It is clear that the novel compounds of this invention are effective not only for the smaller mammals, but also for larger mammals including primates.

When testing the other compounds listed in Table I above, in accordance with the above procedures, substantially the same results are achieved.

Anesthetics and Hypothermics and Other Neuroprotective Compounds

The second group of guanidino compounds are compounds which have neuroprotective efficacy, and in some cases are also effective as anesthetics and/or hypothermic agents, which have other desirable properties, and which preferably have the following formulae: IIA.

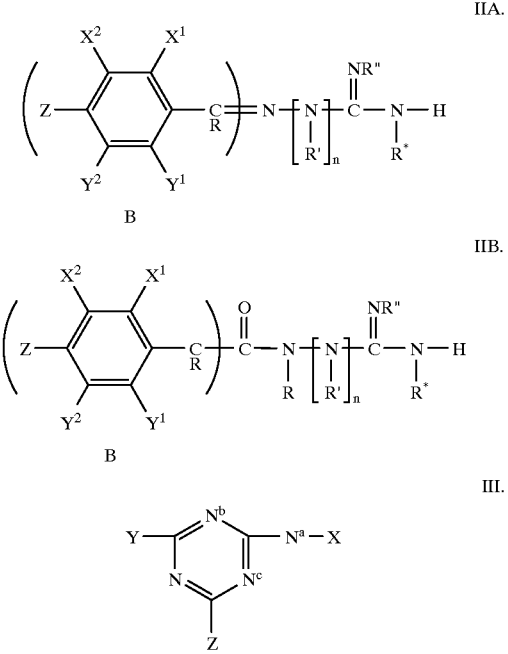

Referring to Formulae II, n can be zero or an integer up to 2; Z, X1, X2, Y1 and Y2 can be the same or different and can include, as examples, hydrogen, halogen, trifluoromethyl or C1–C4 alkyl oxyalkyl, hydroxyl, phenyl or condensed phenyl, phenoxy, naphthoxy, or substituted such aryl or aryloxy groups; preferably, one substituent is halogen or trifluoromethyl, at least one of X1 and Y1 is not hydrogen and not more than three of the X1, Y1, X2, Y2 and Z groups are other than hydrogen; each of R, R', R" and R* can be, for example, hydrogen, C1–C4 alkyl, C2–C4 alkenyl, or C2–C4 alkynyl, with the proviso, among other alternatives, that any two of R*,R" and R' can together form a hydrocarbyl bridge of preferably from 2 to 4 carbon atoms, such as alkylene or alkenylene groups, and with the further proviso that one of Y1 and R is preferably hydrogen. The term "hydrocarbyl bridge of 2 to 4 carbon atoms" is exemplified and illustrated by the following examples, the bracketed portions being the bridging groups:

alkylene bridge

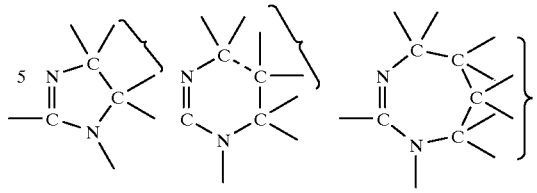

alkenylene bridge

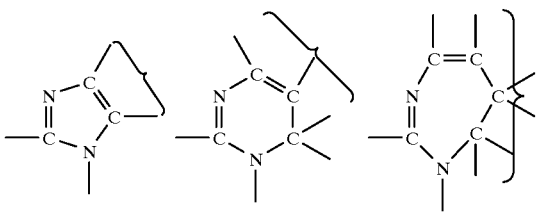

In the guanidino compounds of Formulae II and III, X1 preferably is middle halogen—that is, chlorine or bromine, Y1 is also preferably middle halogen, Z preferably is hydrogen or middle halogen, and R, R', R" and R* are preferably all hydrogen.

When N,

in Formula II, is replaced by a carbon atom, i.e.,

in Formula II, the guanidino moiety is changed to an amidino group and the compound becomes an alpha adrenoceptor antagonist, as in Compounds 96–101, 162, 163, and 192 in Tables I and II below. They will thus antagonize hypothermia and anesthesia, and also have neuroprotective activity, i.e., after trauma or disease caused by injury, to reduce damage to the central nervous system.

Referring to Formula III, X, Y and Z can be the same or different groups, which cumulatively confer sufficient lipophilicity to the overall compound to permit passage through the blood-brain barrier, and do not interfere with the alpha-adrenergic activity of the guanidino moiety, shown set off by phantom lines.

Groups Y and Z can each be connected to the triazine group ring structure by a nitrogen atom, and in such cases each group is thus the same, or different, from the ($N^a$-X) group. It has thus been found that being part of the triazine group of Formula No. III, or of another cyclic structure (including a xanthine group), does not eliminate the adrenoceptor activity of the guanidino moiety. The groups Y, Z and X, must be sufficiently lipophilic to allow the compound to pass through the blood-brain barrier, without hindering the adrenergic, dopaminergic, serotonergic, GABA-ergic or cholinergic agonist activity of the neighboring groups. The groups X, Y, and Z, can thus have some other pharmacologic activity in addition to the alpha adrenergic agonist activity.

These lipophilic groups can be aromatic, cyclic or acyclic, although aromatic groups are generally preferred. Such lipophilic groups include, as examples, any "B group" shown above for the Formula II, guanidino compounds, and can also include any of the receptor active groups of sufficient cumulative lipophilicity, in any combination, shown in the compounds of Tables I and II below.

The aromatic groups useful as substituents for these guanidino compounds preferably include phenyl rings, either a single phenyl ring or two or more phenyl rings, condensed or linked and preferably further substituted with, e.g., one or more halogen atoms, especially chlorine or bromine, oxyalkyl groups, such as oxymethyl, hydroxy groups, hydroxyalkyl groups, and alkyl groups; the alkyl groups substituted on to the phenyl rings preferably have not more than about five carbon atoms, each.

Table I presents the structural formulae for an exemplary list of novel compounds which are useful in the present invention. It should be understood that the listing set forth in Table I is purely exemplary and is in no way intended to be exhaustive.

TABLE I (1) 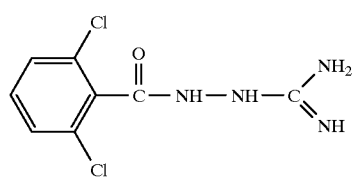

(2) 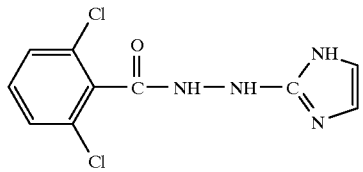

(3) 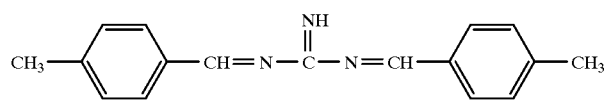

(4) 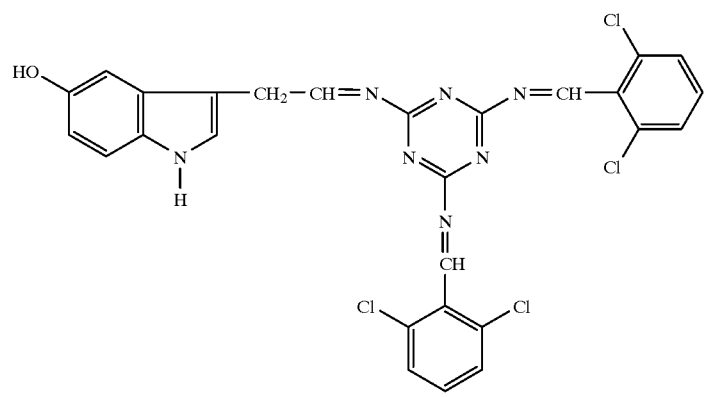

(5) 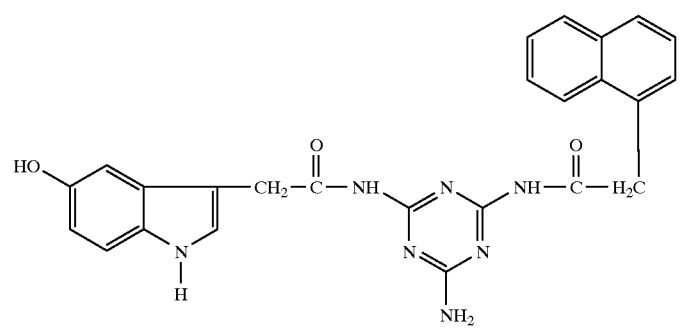

TABLE I-continued
(6) 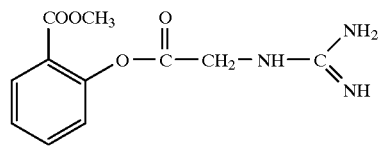
(7) 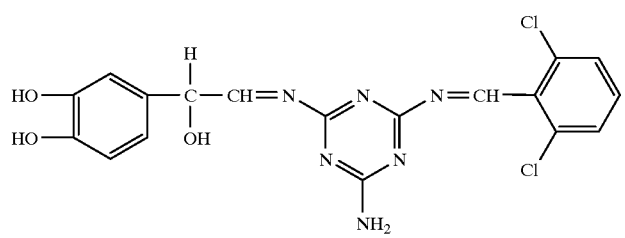
(8) 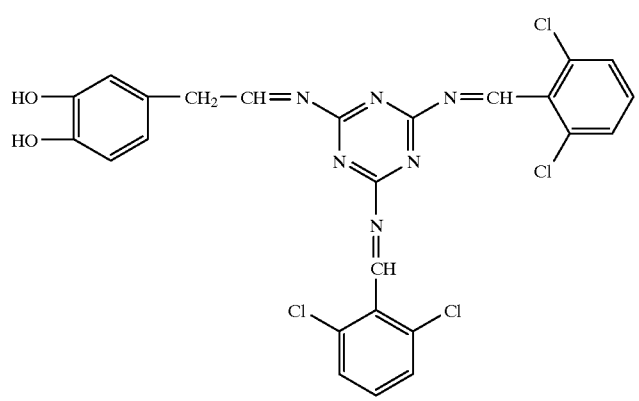
(9) 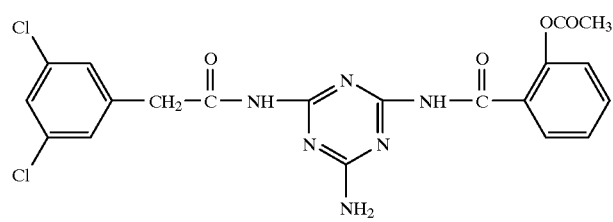
(10) 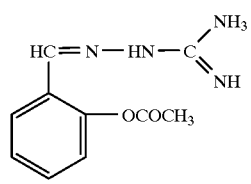
(11) 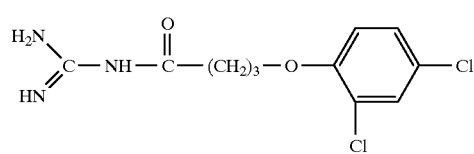
(12) 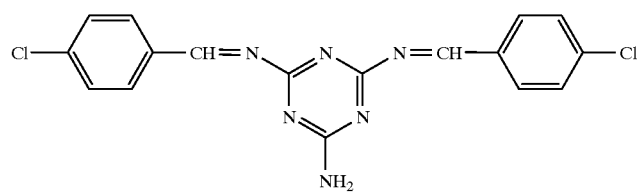

TABLE I-continued
(13) 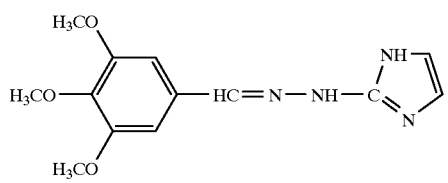
(14) 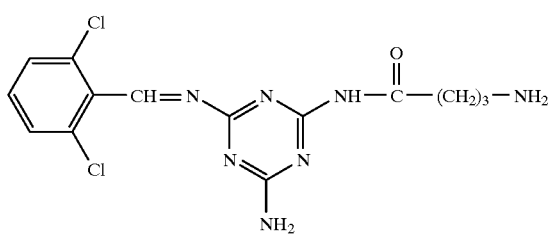
(15) 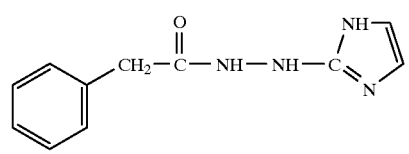
(16) 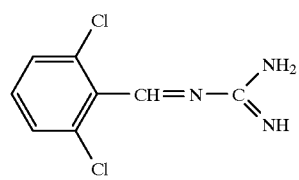
(17) 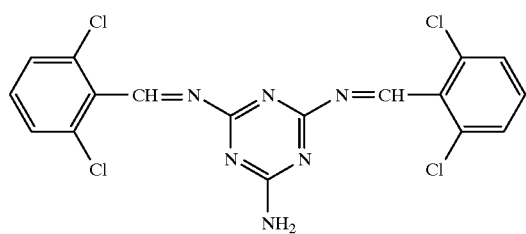
(18) 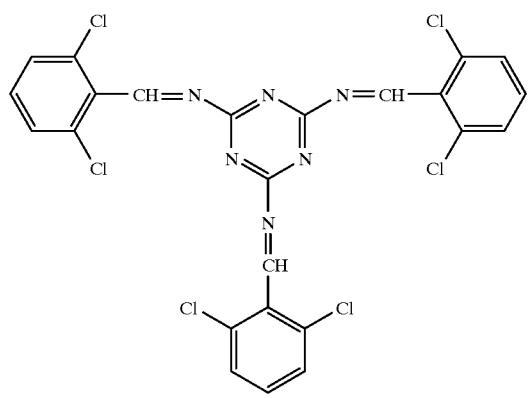

TABLE I-continued
(19) 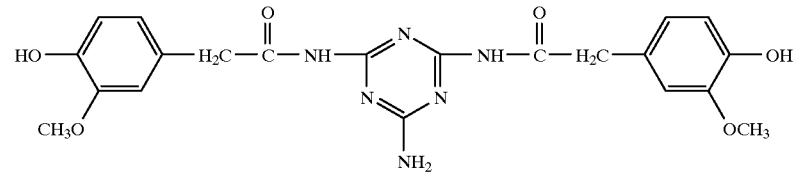
(20) 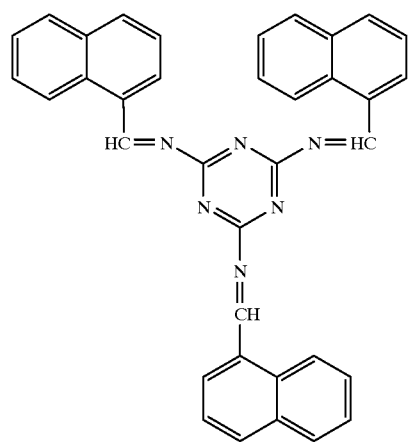
(21) 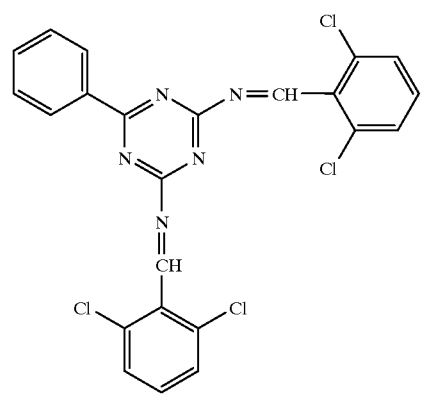
(22) 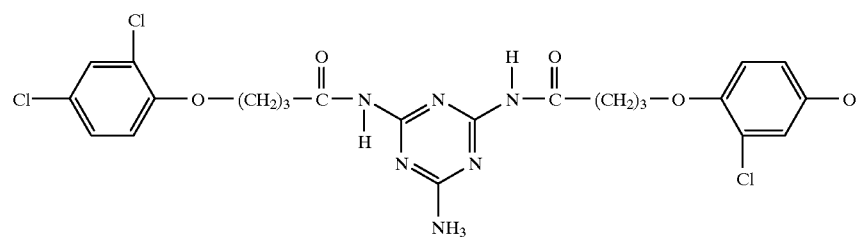

TABLE I-continued
(23) 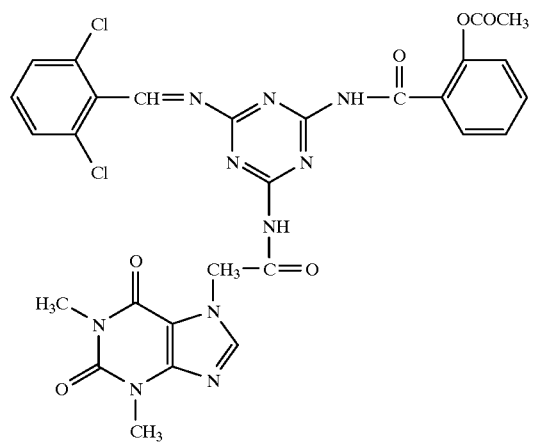
(24) 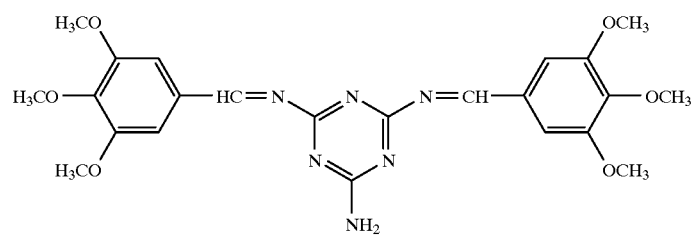
(25) 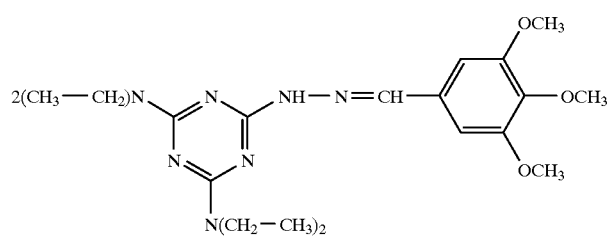
(26) 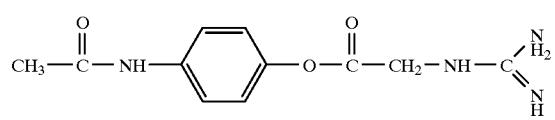
(27) 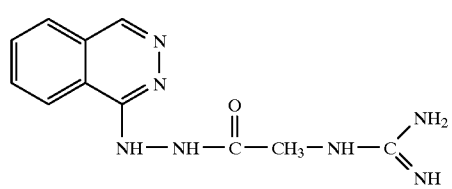
(28) 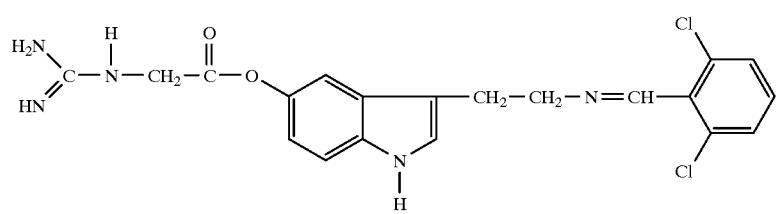

TABLE I-continued
(29) 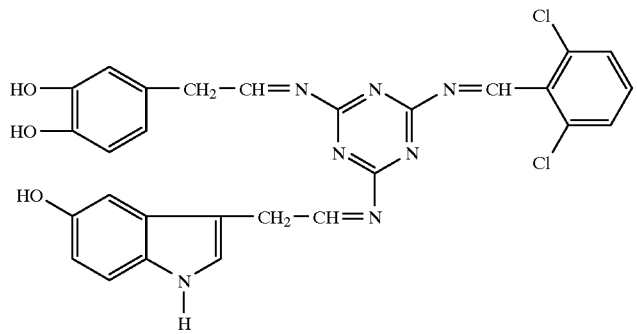
(30) 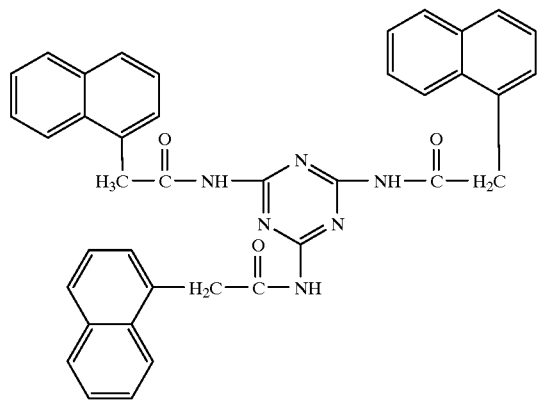
(31) 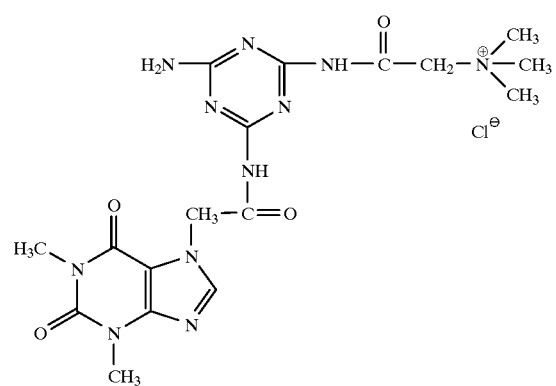
(32) 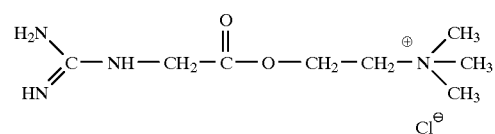
(33) 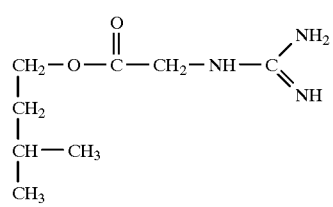

TABLE I-continued
(34) 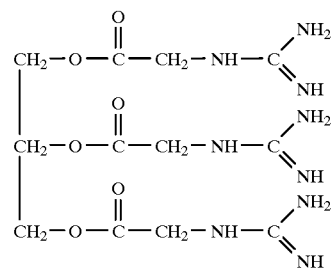
(35) 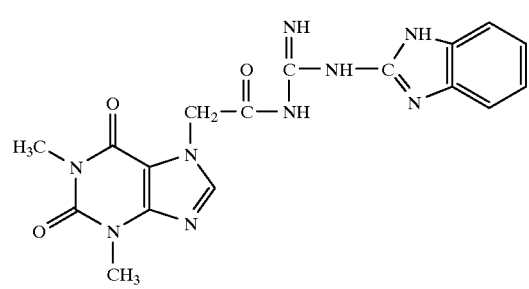
(36) 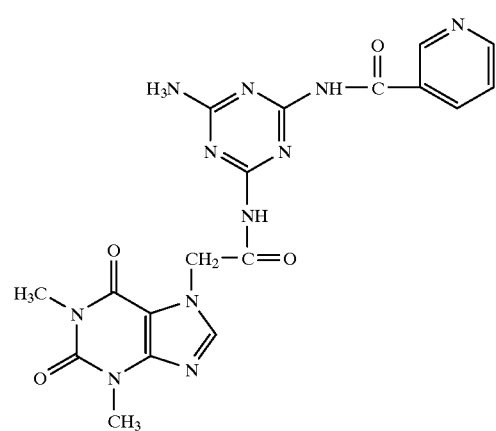
(37) 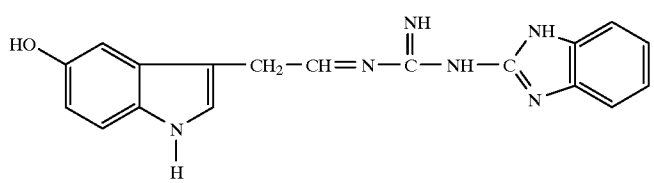
(38) 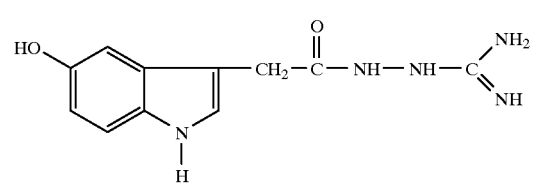

TABLE I-continued
(39) 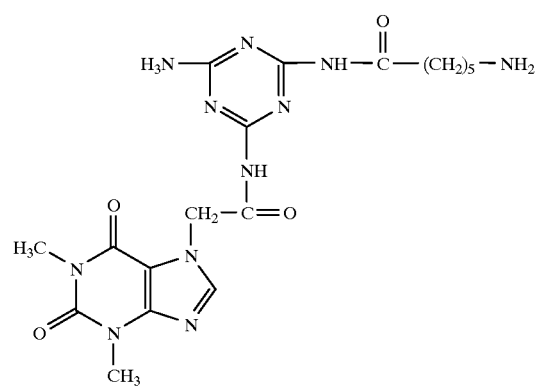
(40) 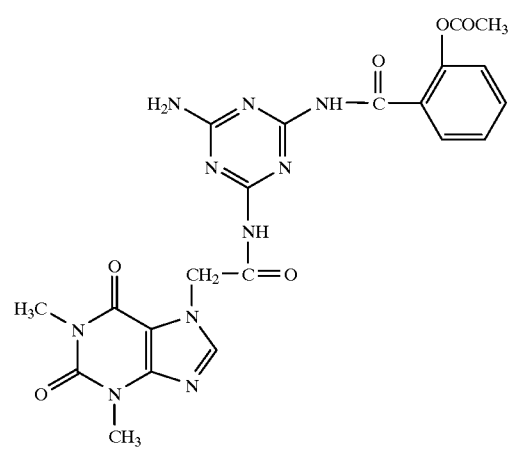
(41) 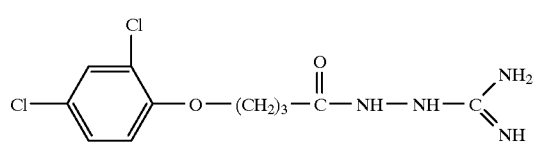
(42) 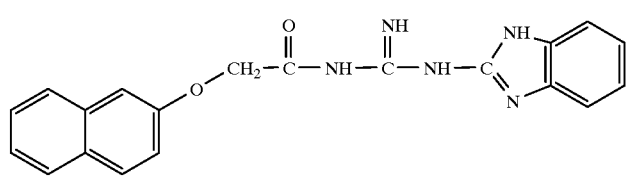
(43) 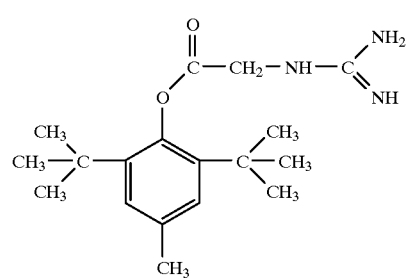

TABLE I-continued
(44) 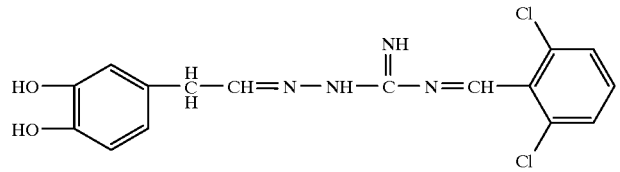
(45) 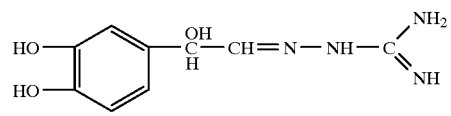
(46) 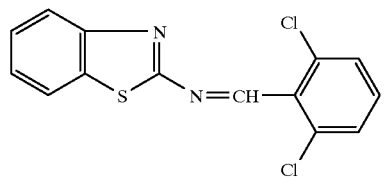
(47) 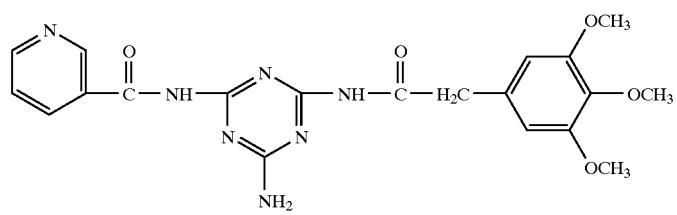
(48) 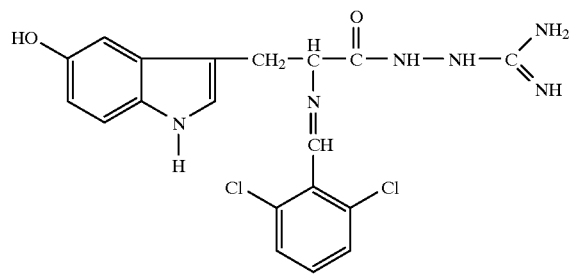
(49) 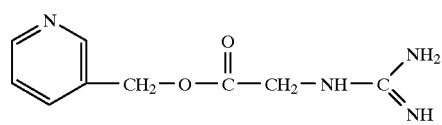
(50) 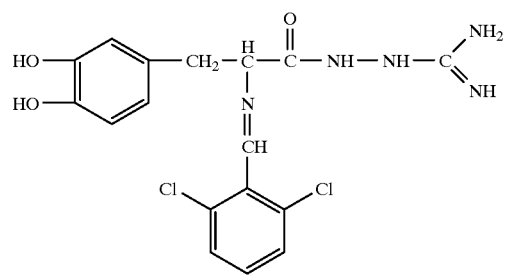

TABLE I-continued
(51) 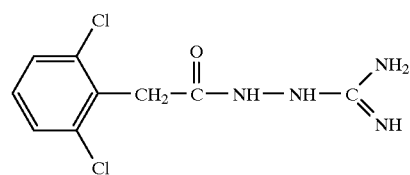
(52) 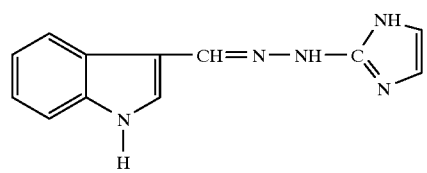
(53) 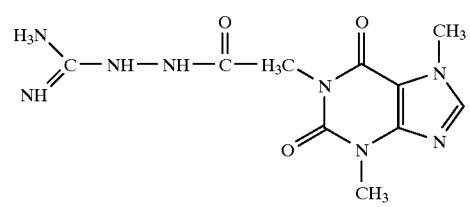
(54) 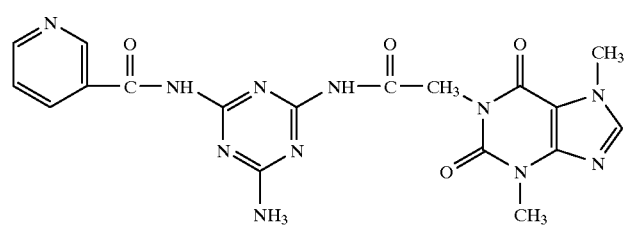
(55) 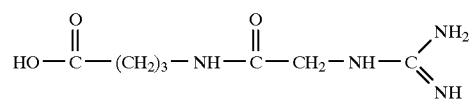
(56) 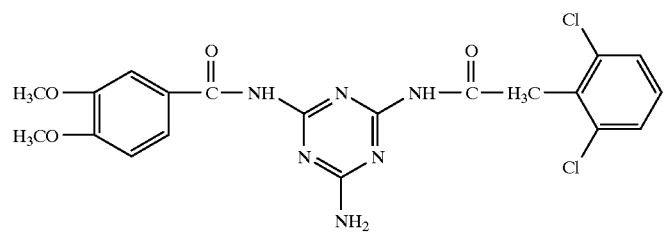
(57) 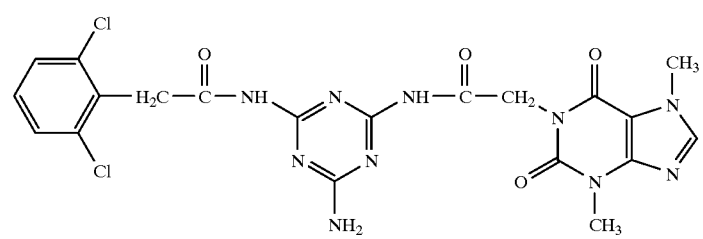

TABLE I-continued
(58) 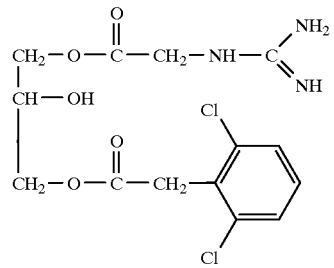
(59) 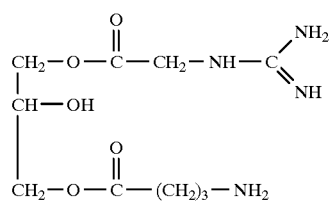
(60) 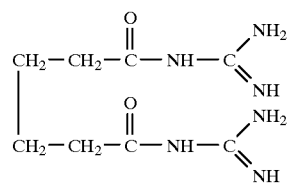
(61) 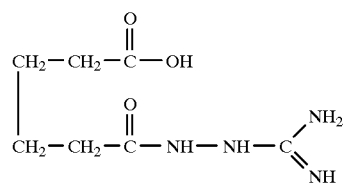
(62) 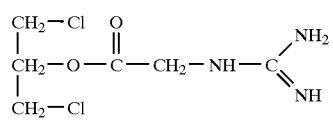
(63) 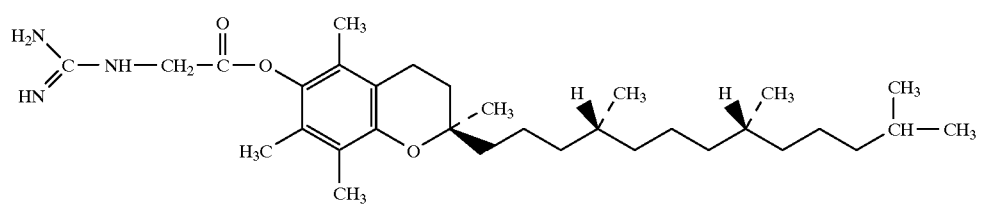
(64) 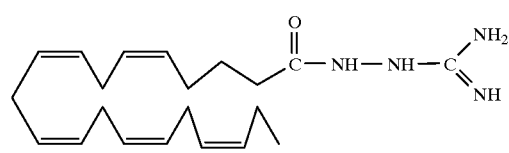

TABLE I-continued
(65) 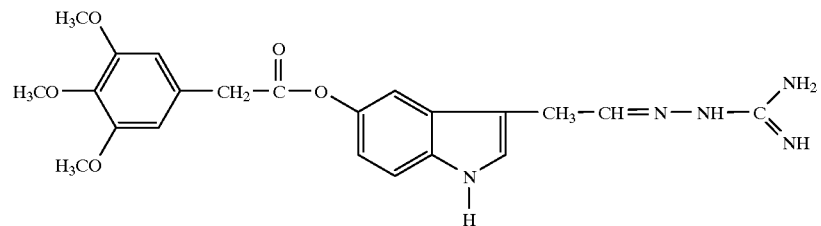
(66) 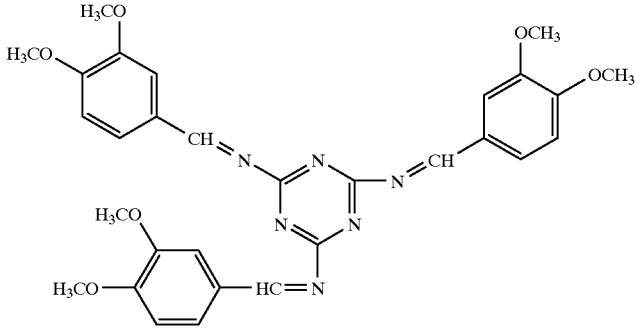
(67) 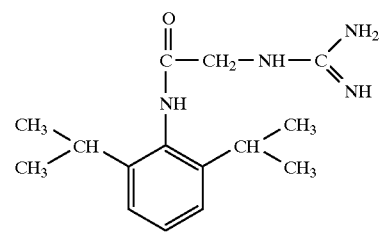
(68) 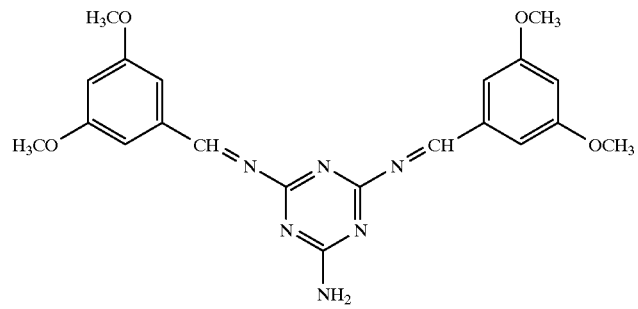
(69) 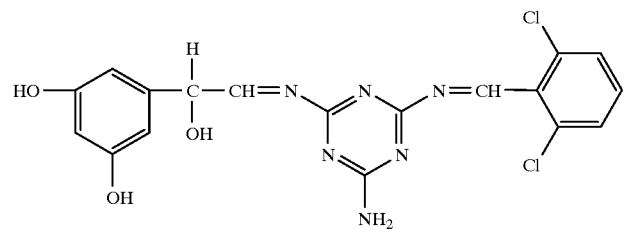

TABLE I-continued
(70) 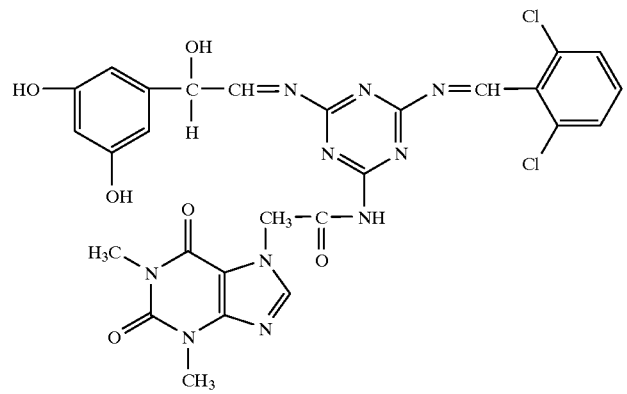
(71) 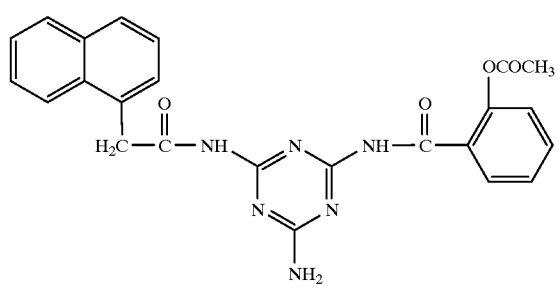
(72) 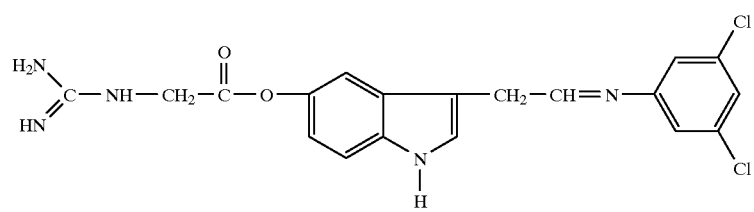
(73) 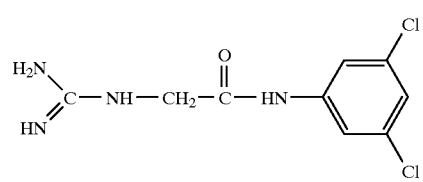
(74) 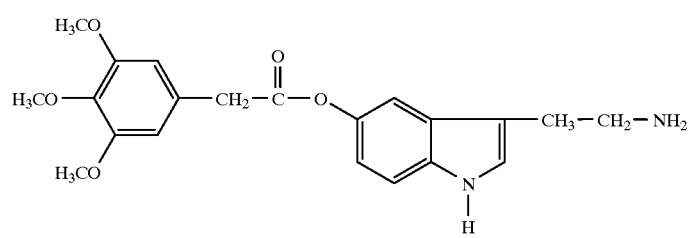
(75) 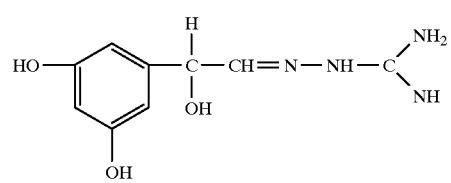

TABLE I-continued
(76) 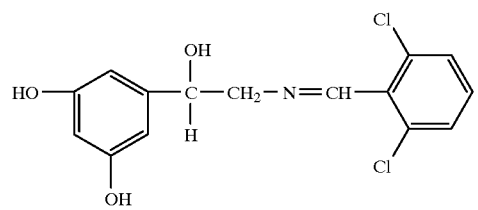
(77) 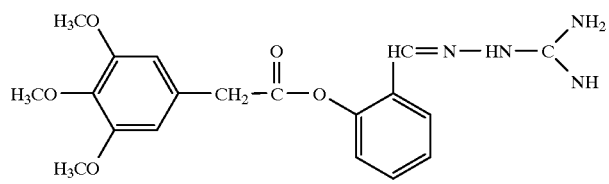
(78) 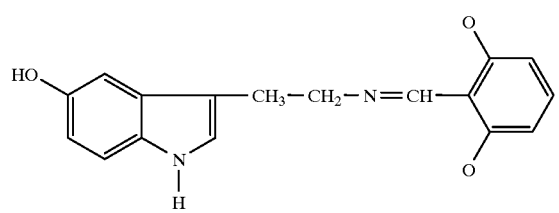
(79) 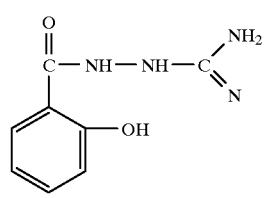
(80) 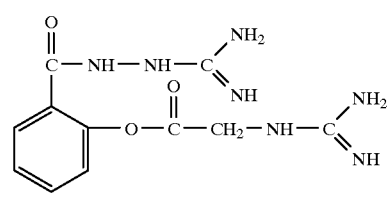
(81) 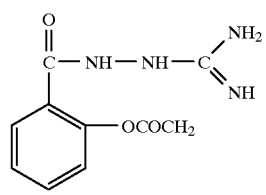
(82) 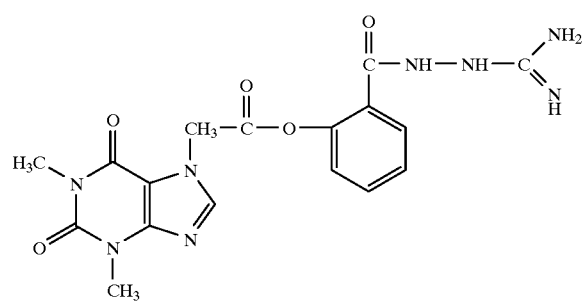

TABLE I-continued
(83) 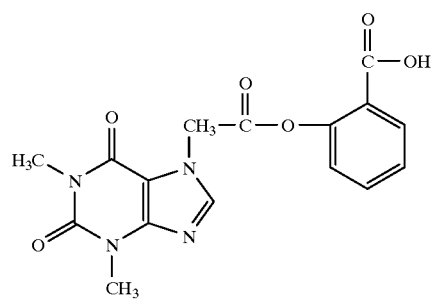
(84) 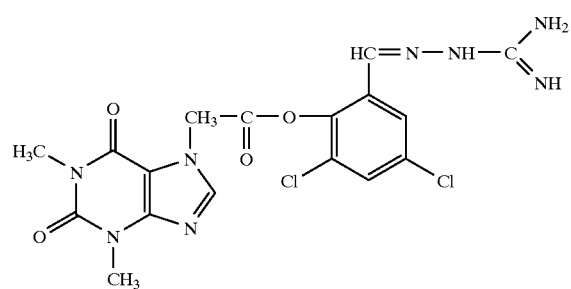
(85) 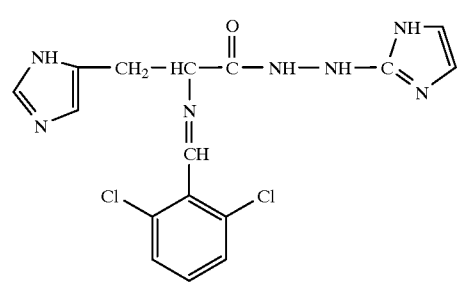
(86) 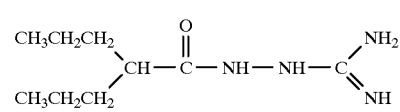
(87) 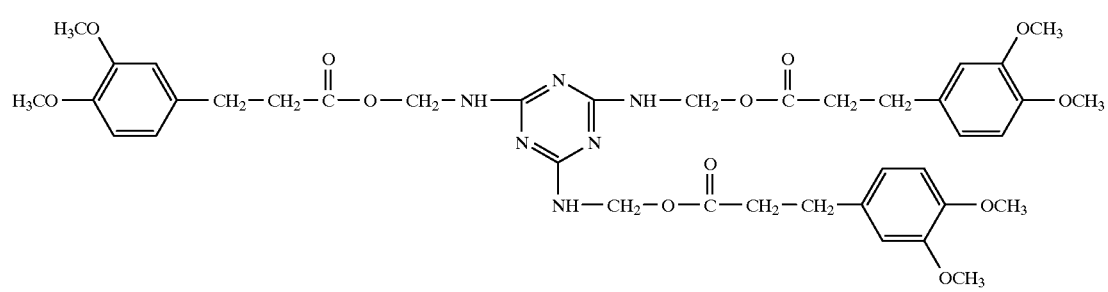
(88) 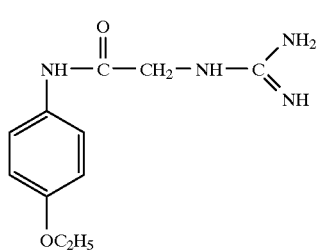

TABLE I-continued
(89) 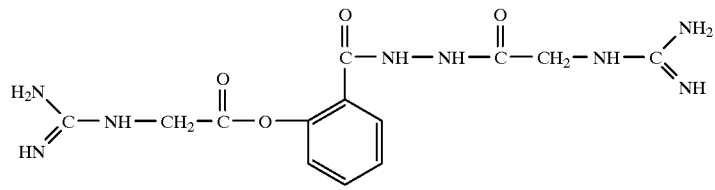
(90) 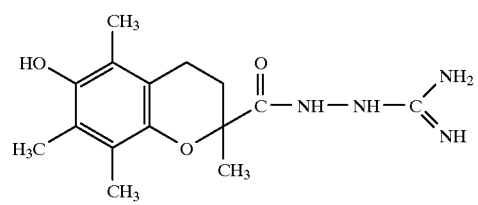
(91) 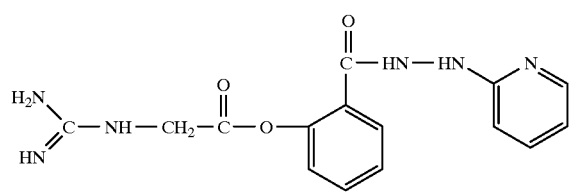
(92) 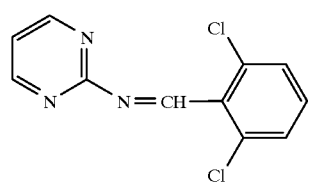
(93) 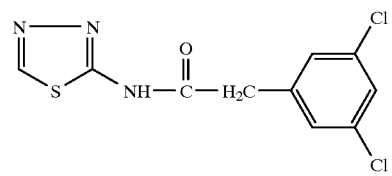
(94) 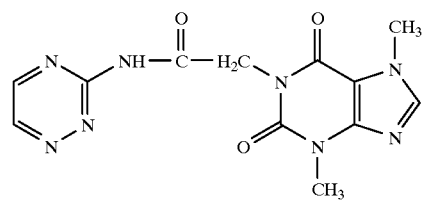
(95) 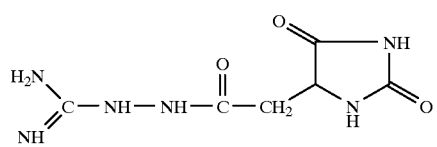
(96) 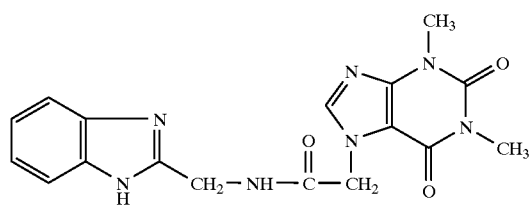

TABLE I-continued
(97) 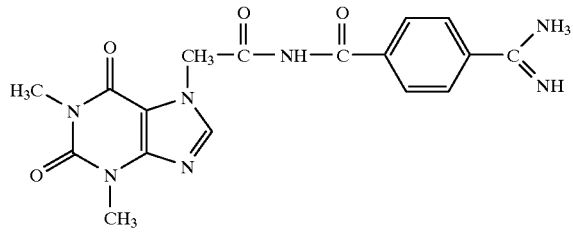
(98) 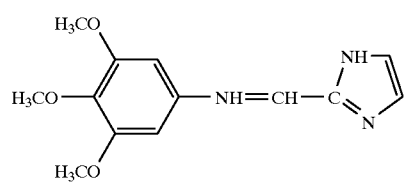
(99) 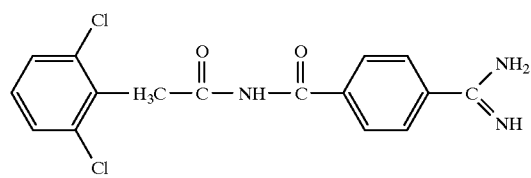
(100) 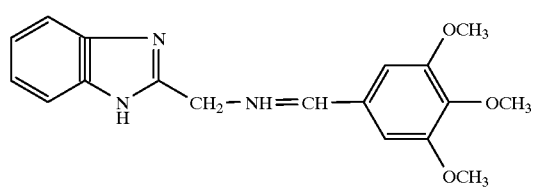
(101) 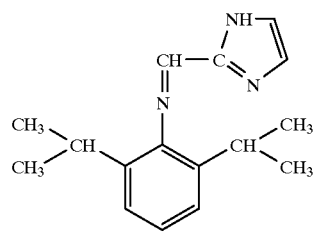
(102) 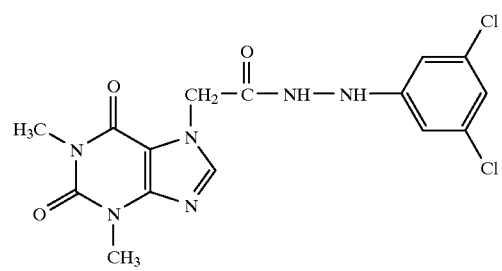
(103) 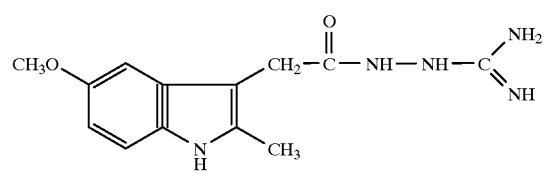

TABLE I-continued
(104) 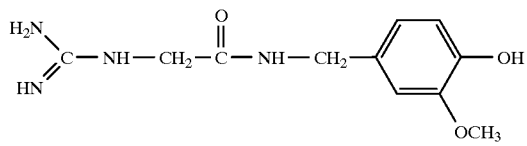
(105) 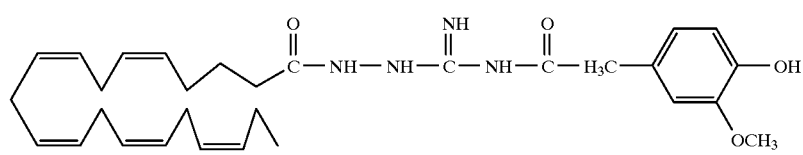
(106) 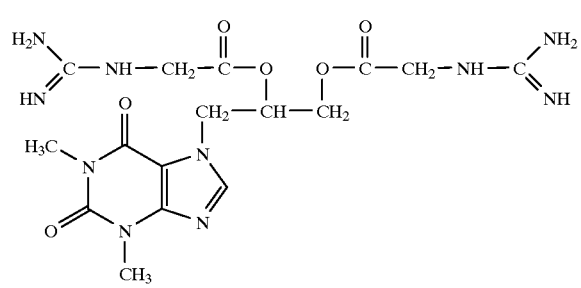
(107) 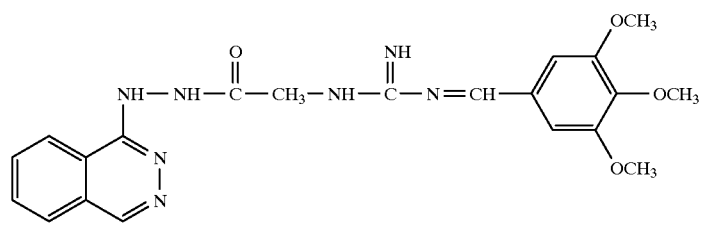
(108) 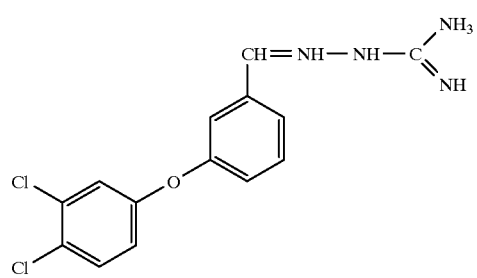
(109) 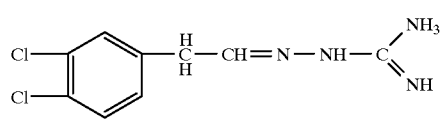

TABLE I-continued
(110) 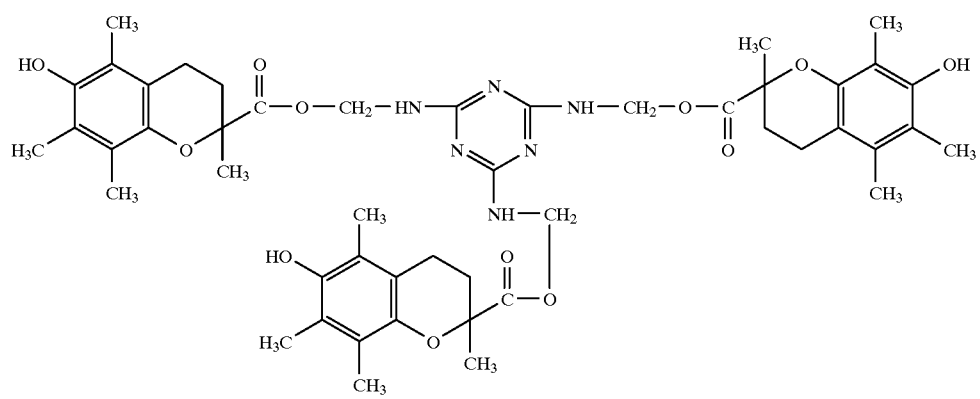
(111) 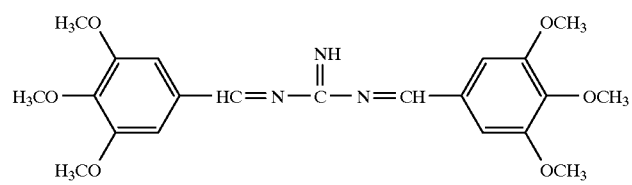
(112) 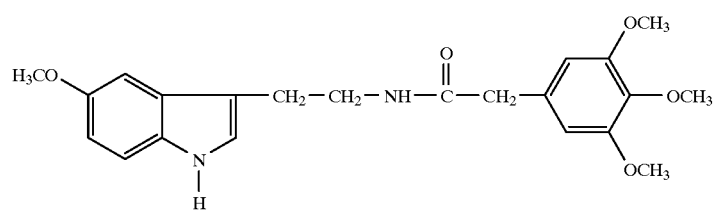
(113) 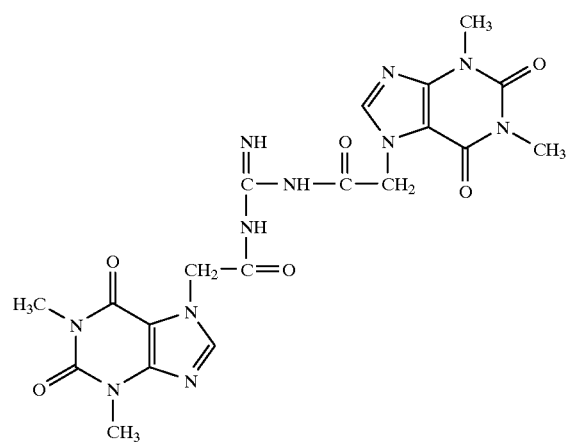
(114) 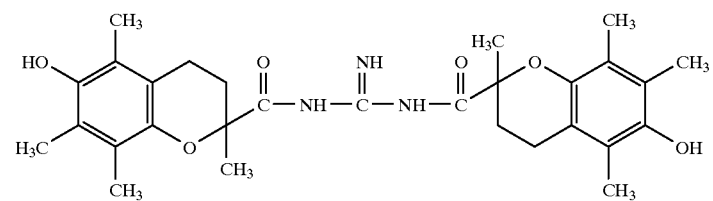

TABLE I-continued
(115)
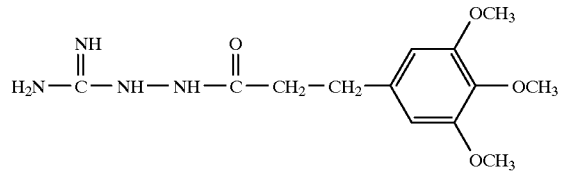
(116)
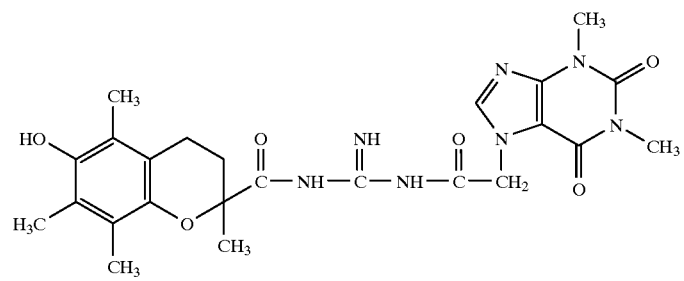
(117)
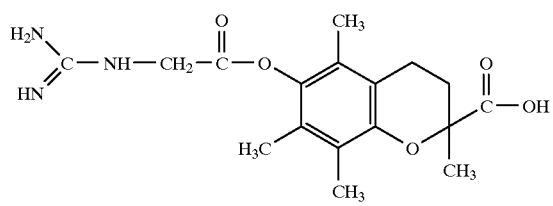
(118)
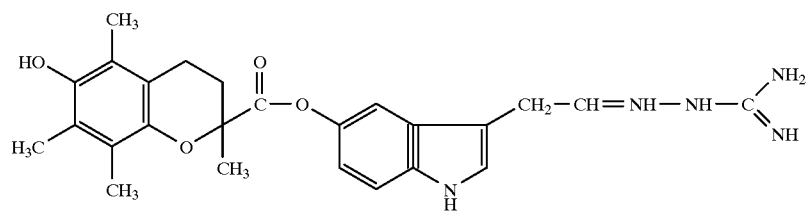
(119)
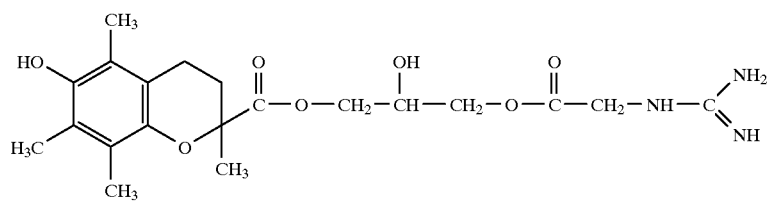
(120)
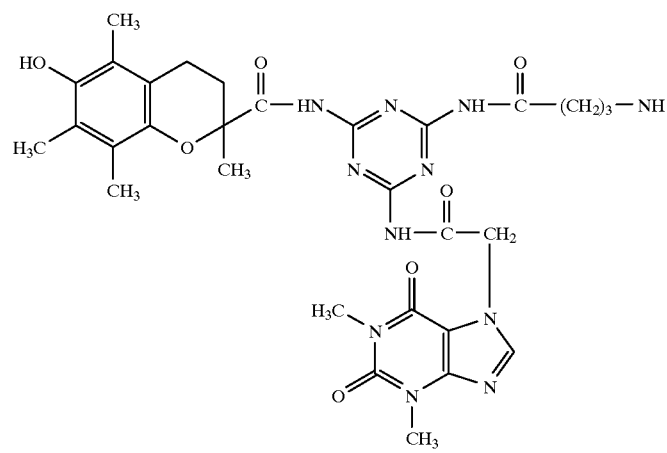

TABLE I-continued
(121) 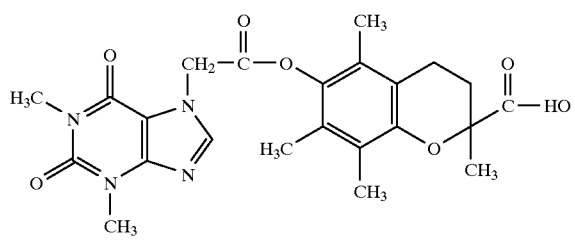
(122) 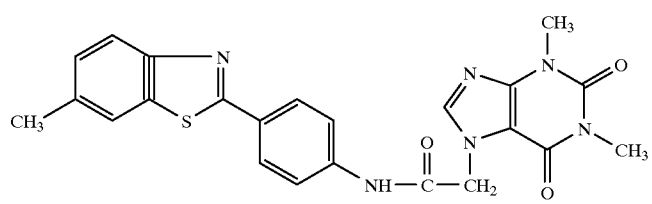
(123) 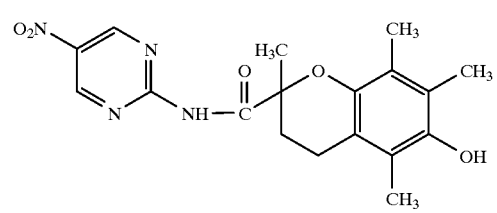
(124) 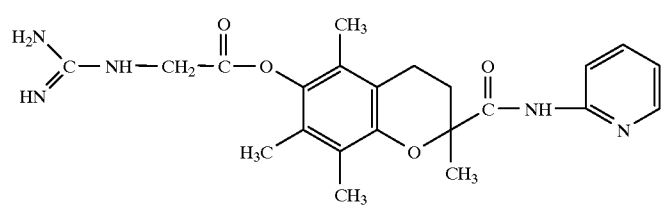
(125) 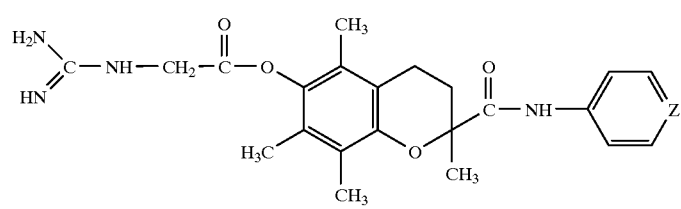
(126) 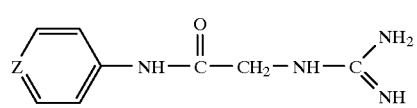
(127) 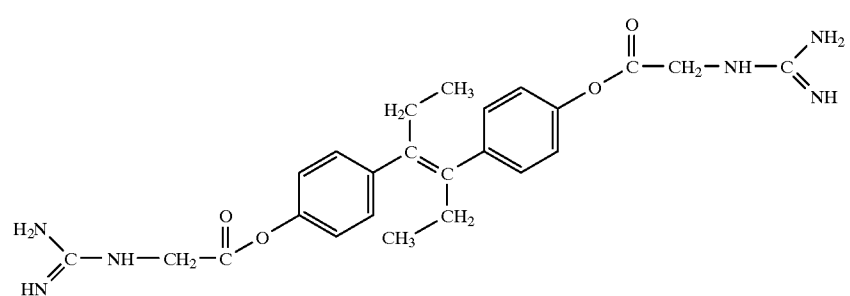

TABLE I-continued
(128)
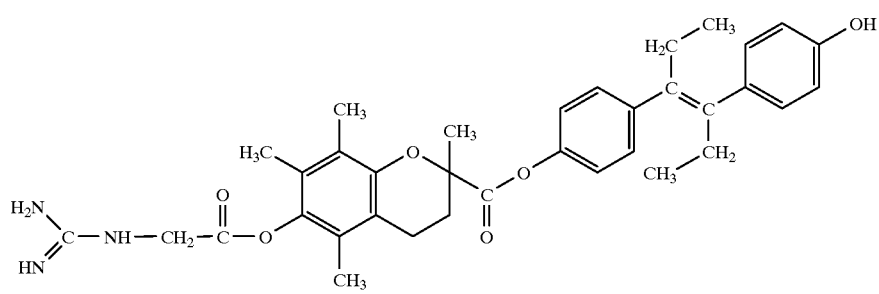
(129)
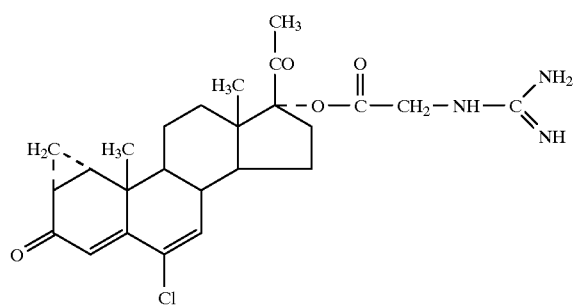
(130)
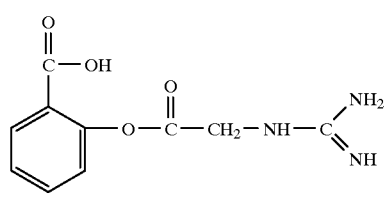
(131)
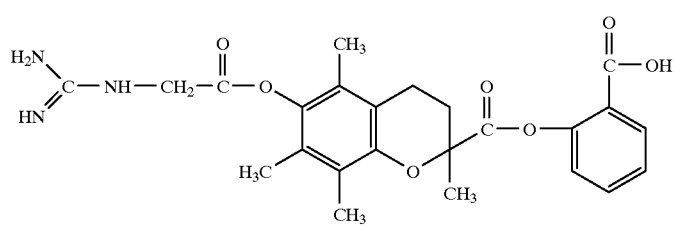
(132)
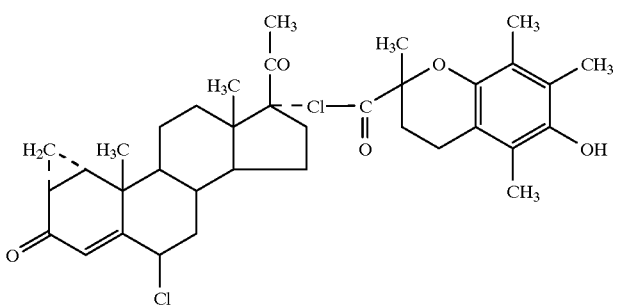
(133)
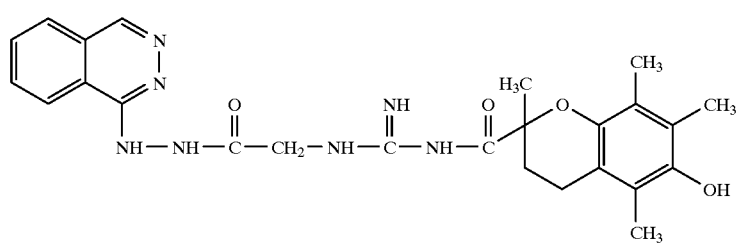

TABLE I-continued
(134)
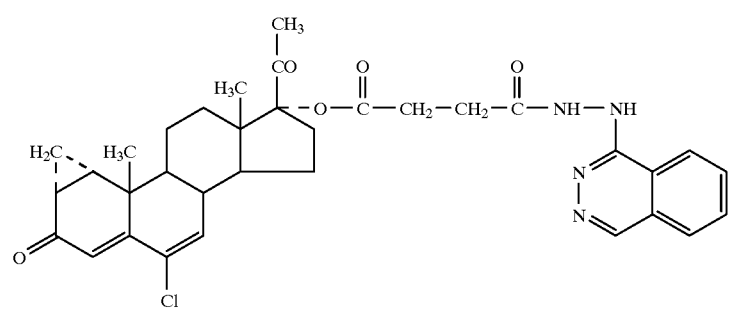
(135)
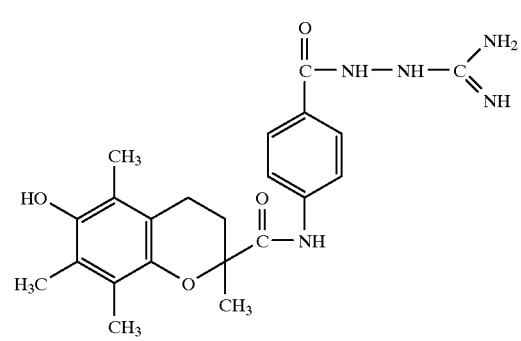
(136)
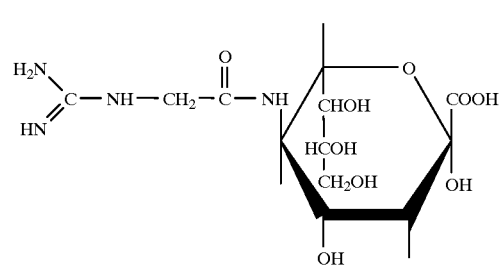
(137)
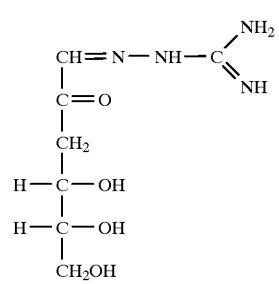
(138)
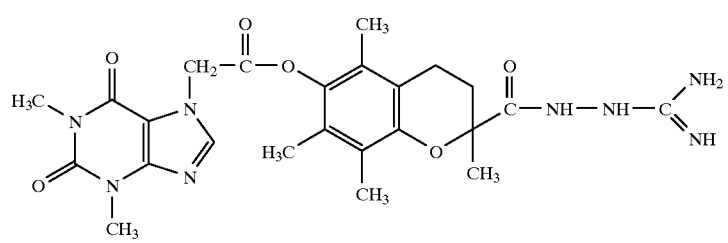

TABLE I-continued
(139) 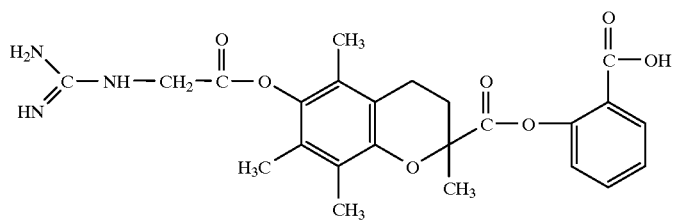
(140) 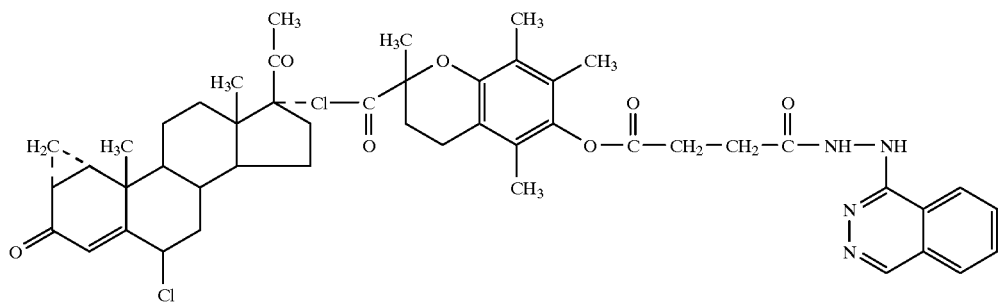
(141) 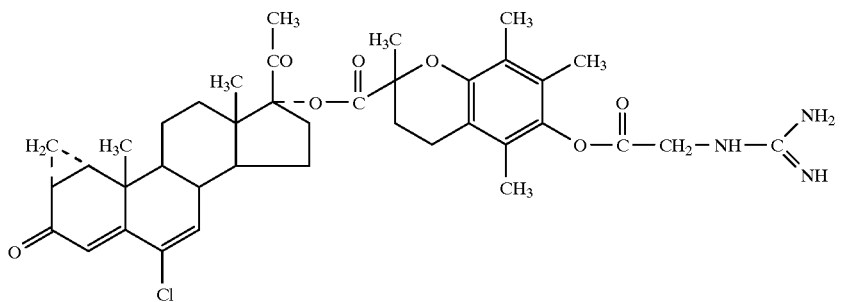
(142) 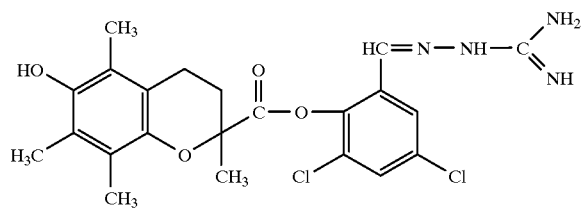
(143) 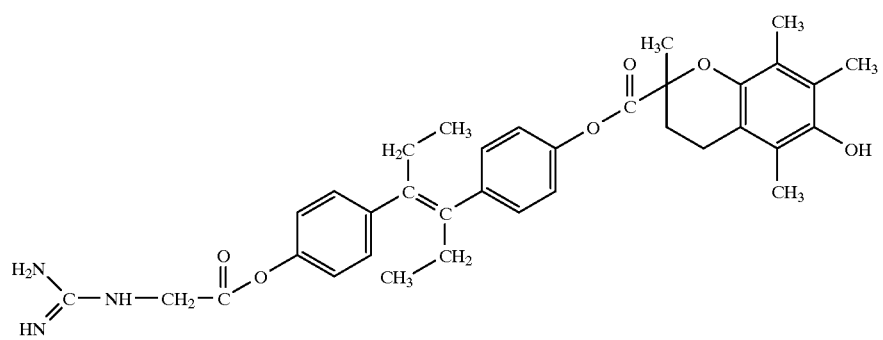

TABLE I-continued
(144)
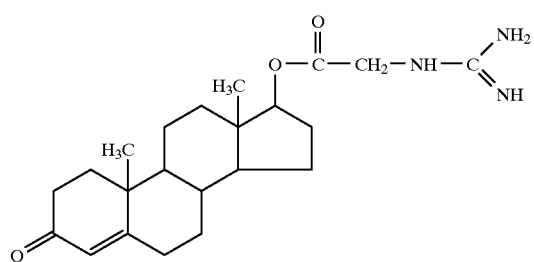
(145)
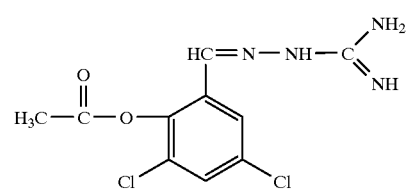
(146)
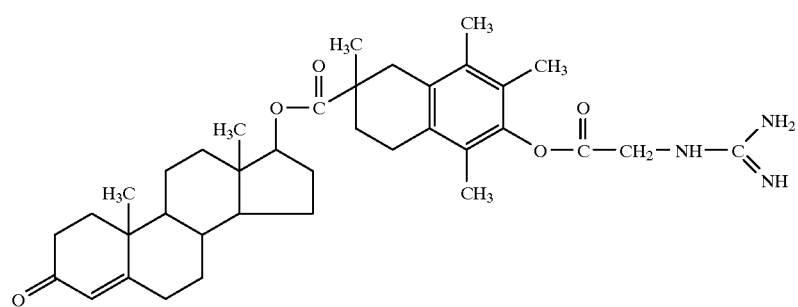
(147)
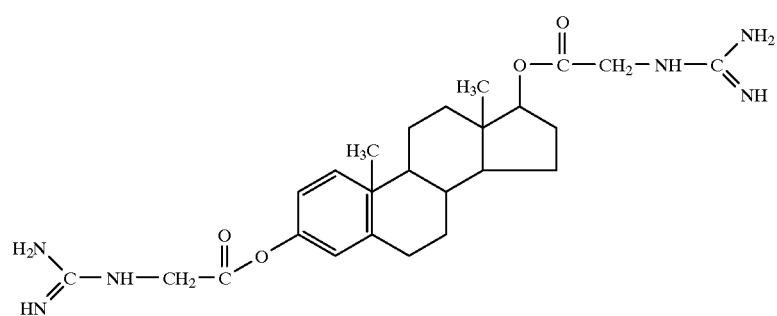
(148)
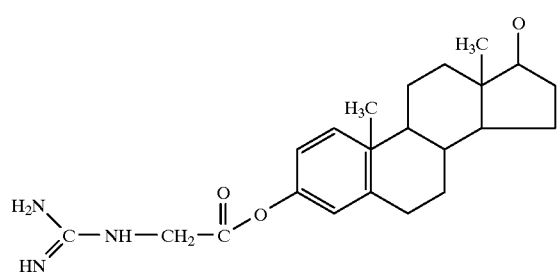

TABLE I-continued
(149) 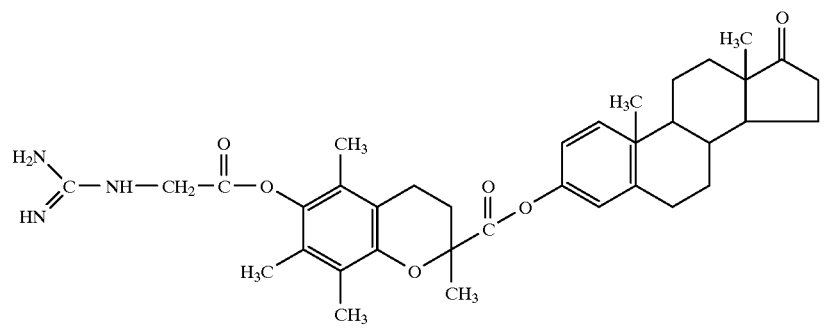
(150) 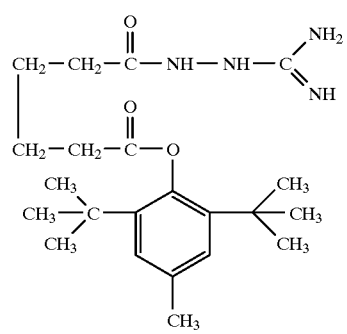
(151) 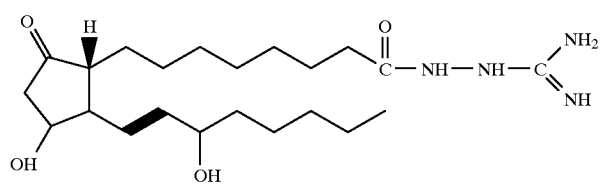
(152) 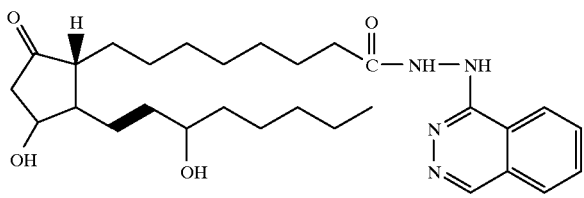
(153) 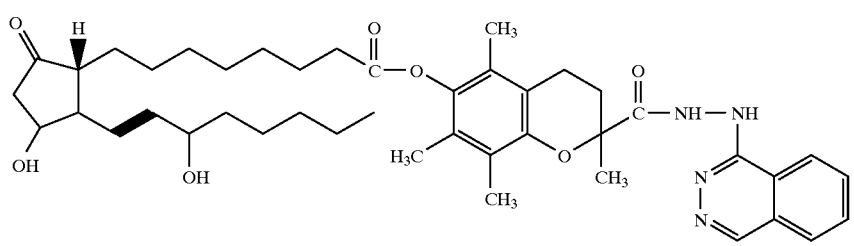

TABLE I-continued
(154)
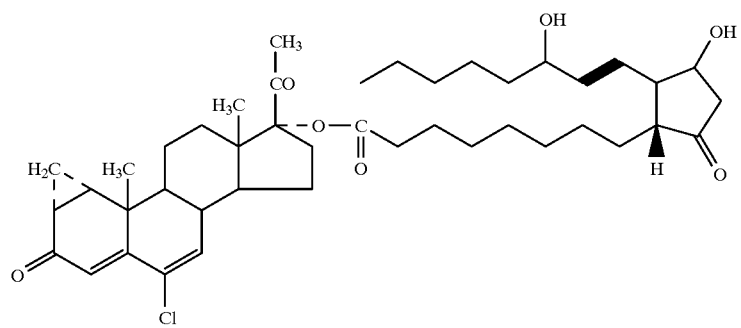
(155)
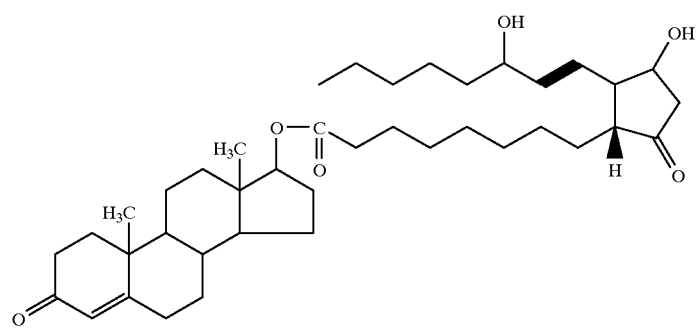
(156)
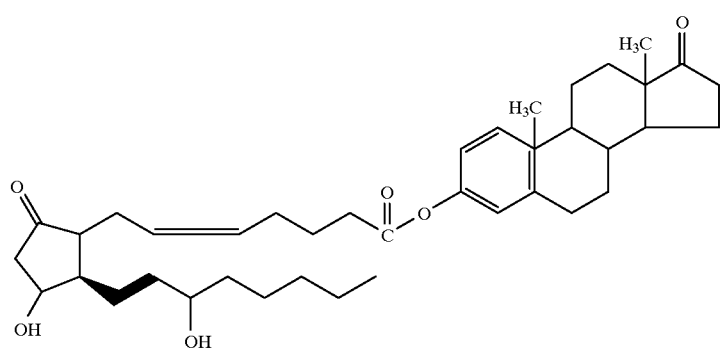
(157)
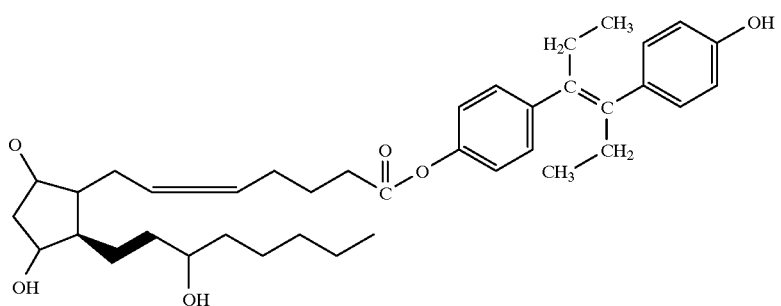

TABLE I-continued
(158) 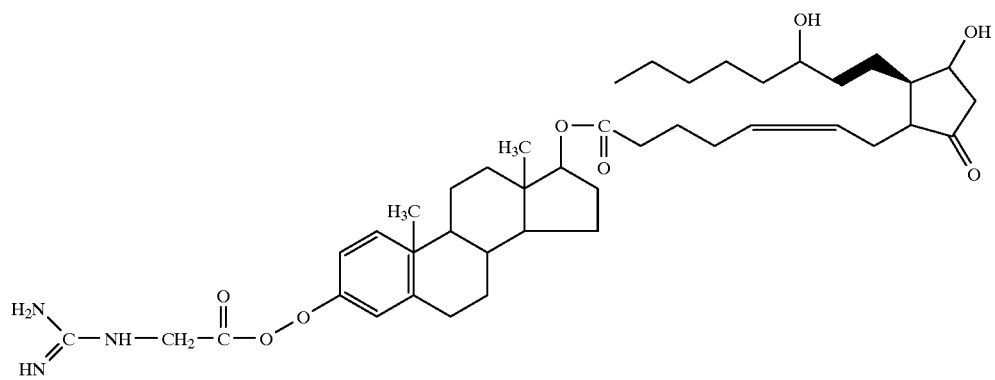
(159) 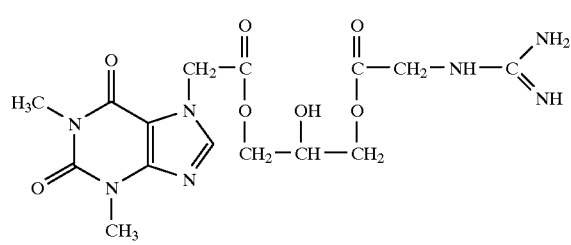
(160) 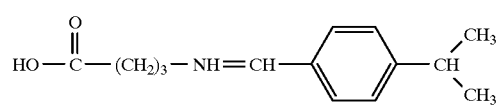
(161) 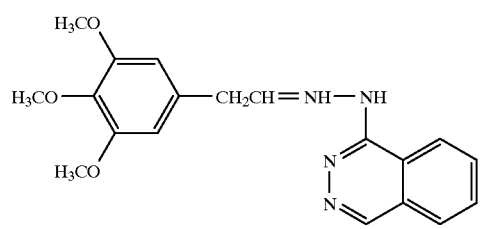
(162) 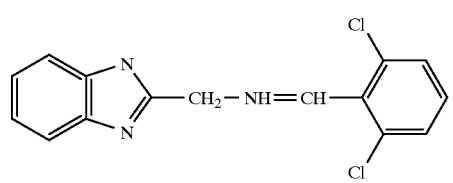
(163) 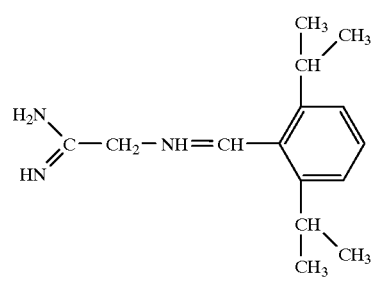

TABLE I-continued
(164) 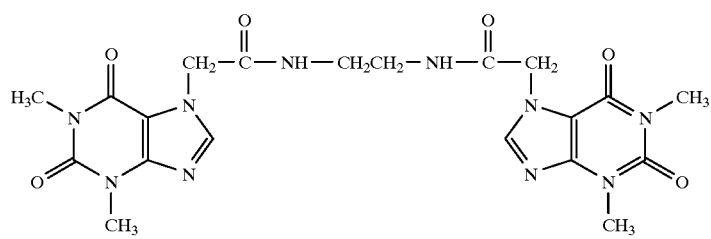
(165) 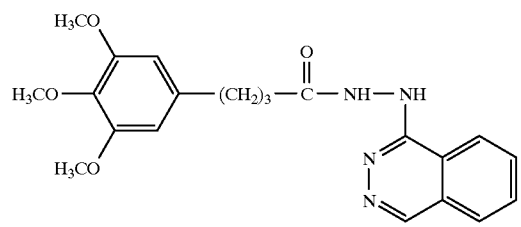
(166) 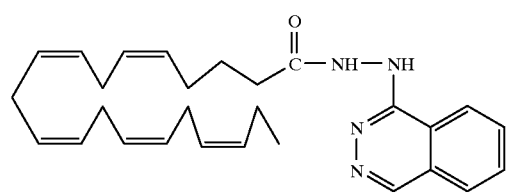
(167) 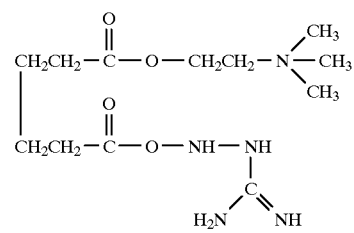
(168) 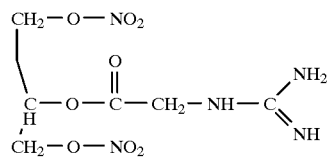
(169) 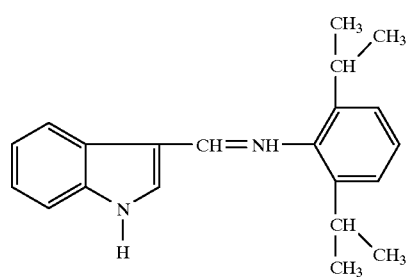

TABLE I-continued
(170)
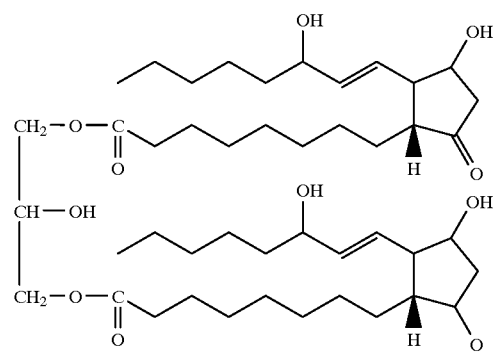
(171)
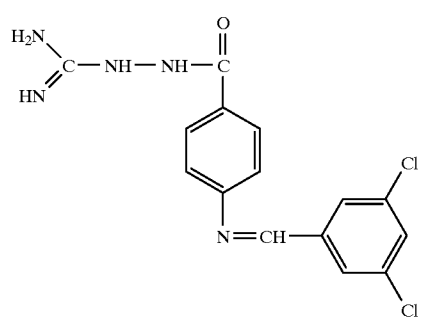
(172)
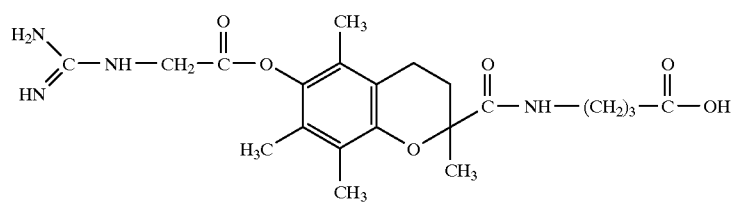
(173)
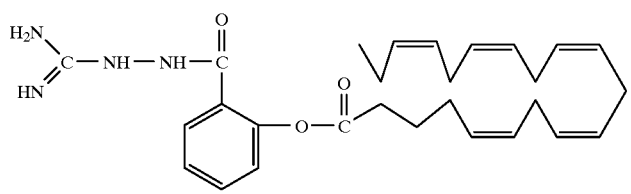
(174)
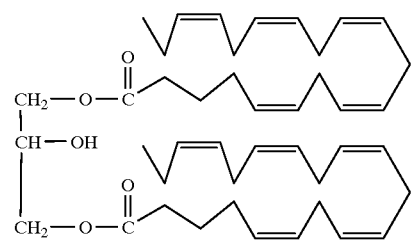

TABLE I-continued
(175) 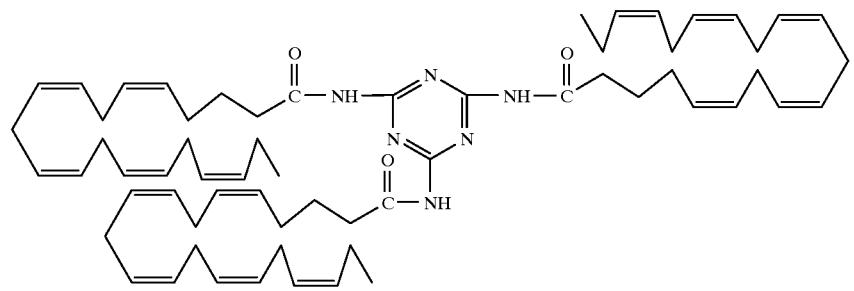
(176) 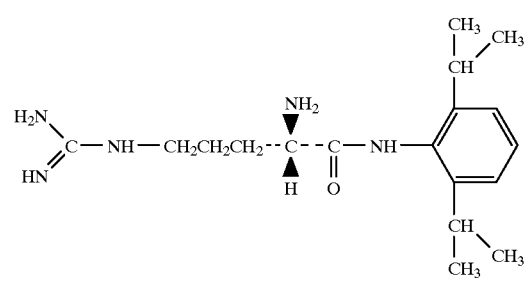
(177) 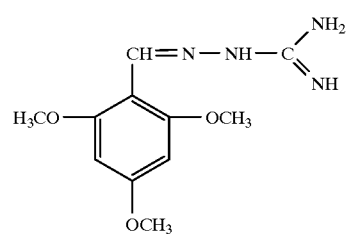
(178) 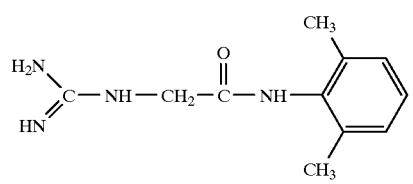
(179) 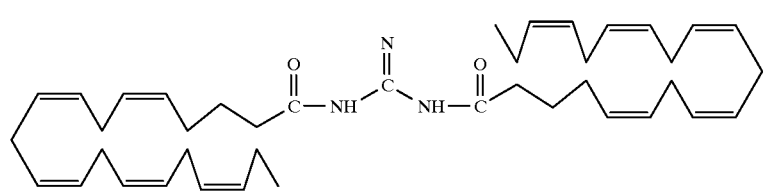
(180) 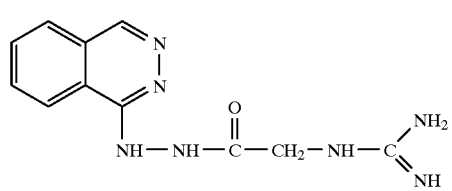
(181) 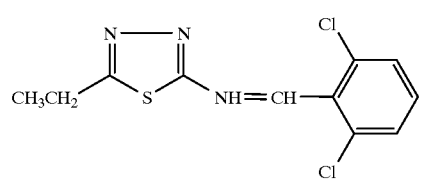

TABLE I-continued
(182) 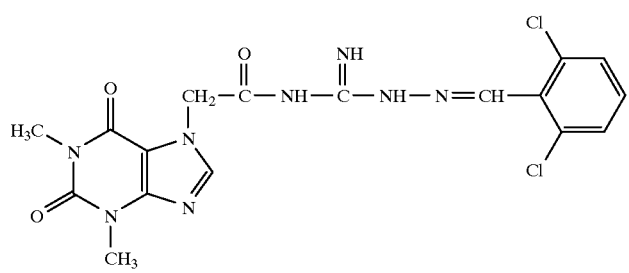
(183) 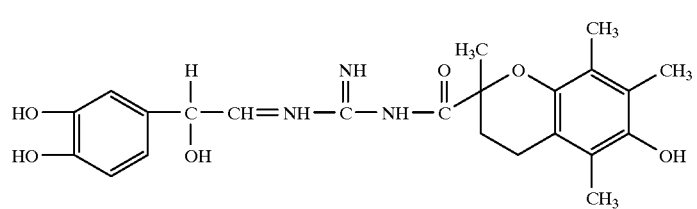
(184) 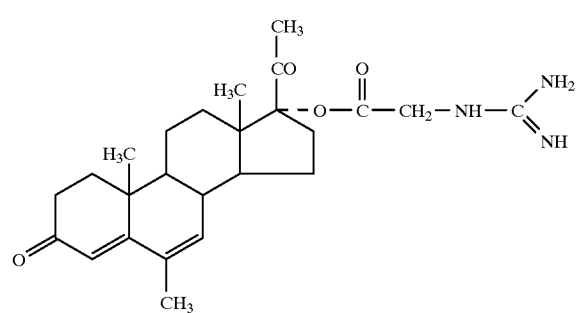
(185) 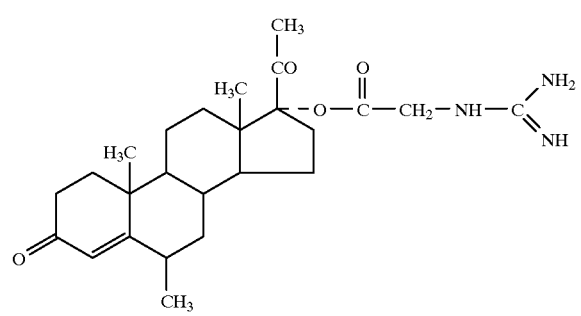
(186) 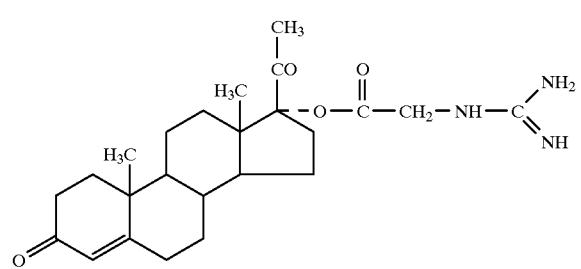

TABLE I-continued
(187) 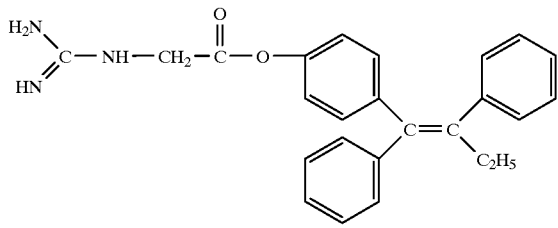
(188) 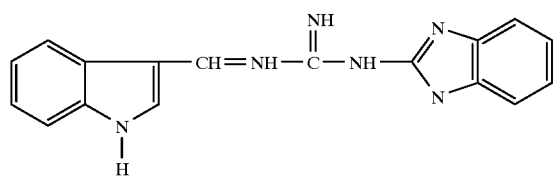
(189) 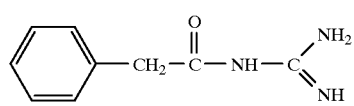
(190) 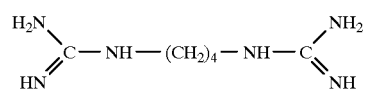
(191) 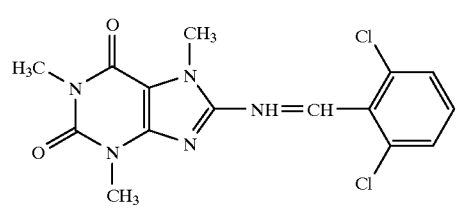
(192) 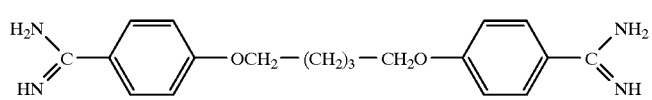
(193) 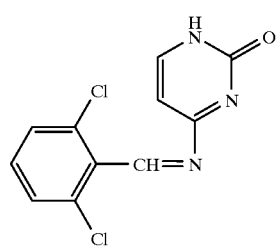
(194) 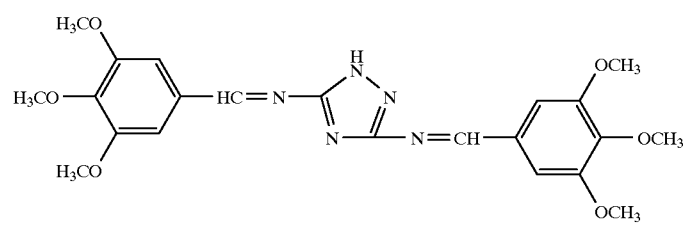

TABLE I-continued
(195)
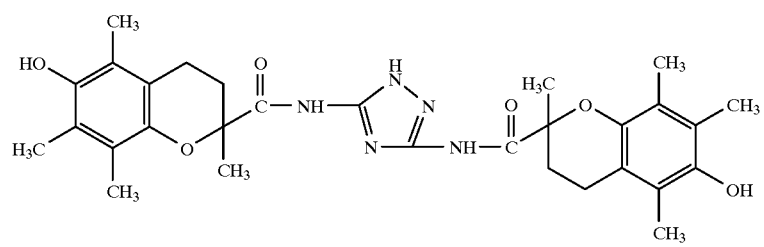
(196)
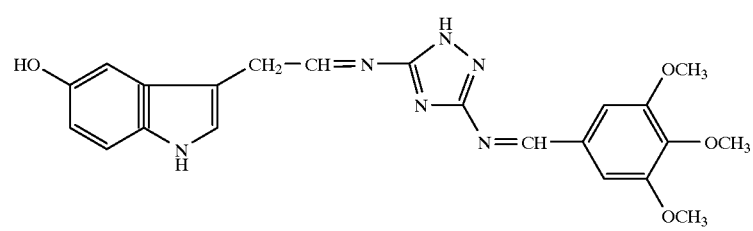
(197)
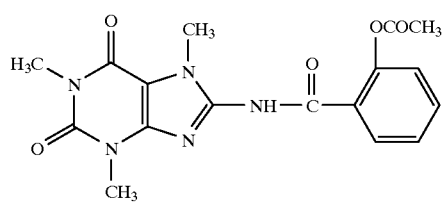
(198)
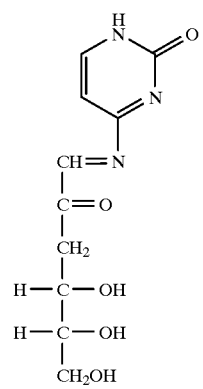
(199)
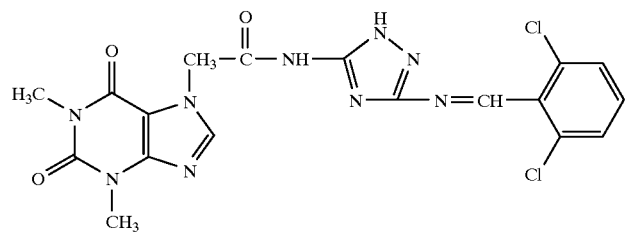
(200)
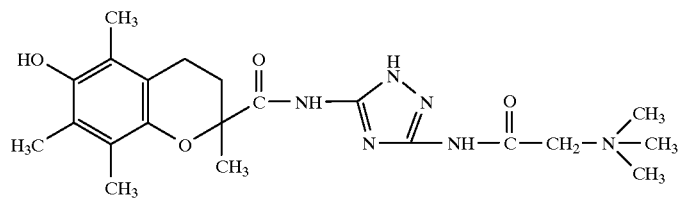

TABLE I-continued
(201)
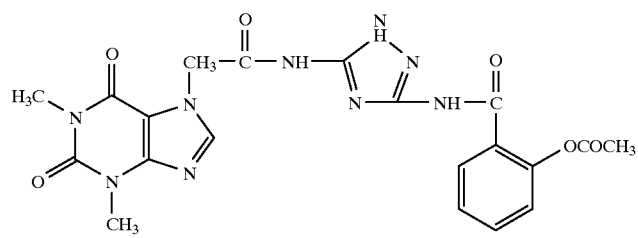
(202)
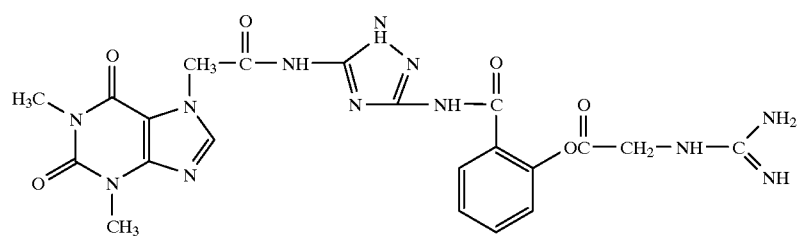
(203)
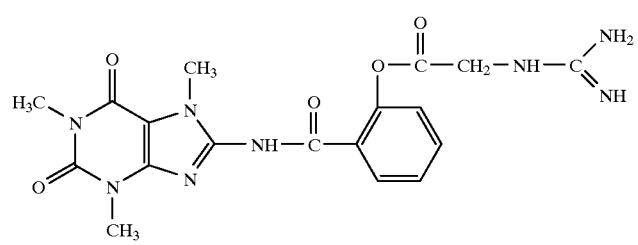
(204)
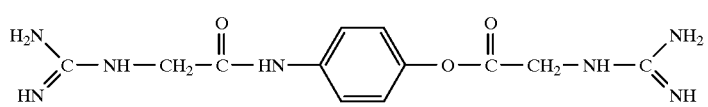
(205)
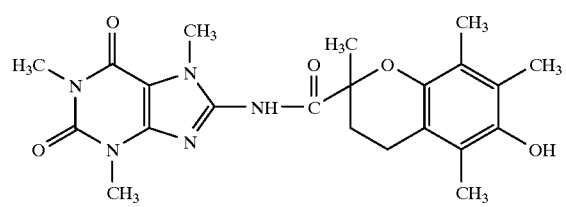
(206)
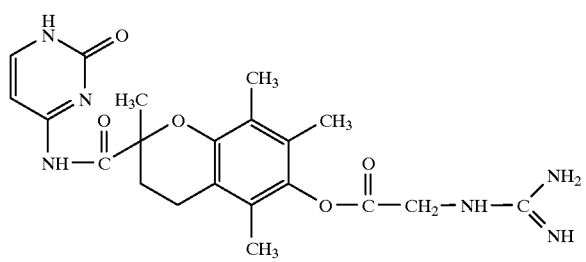
(207)
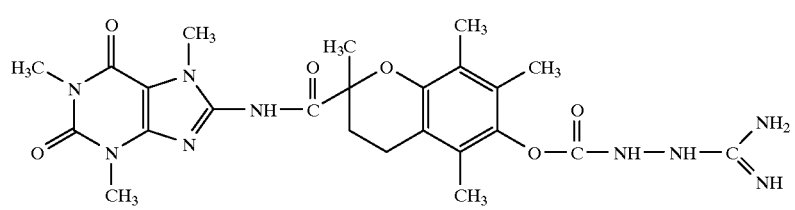

TABLE I-continued
(208) 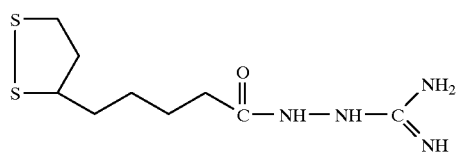
(209) 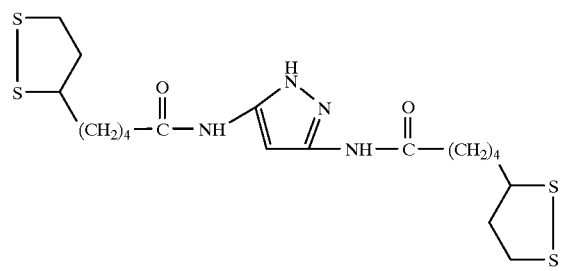
(210) 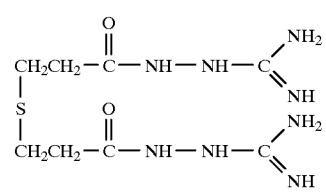
(211) 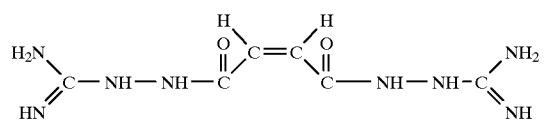
(212) 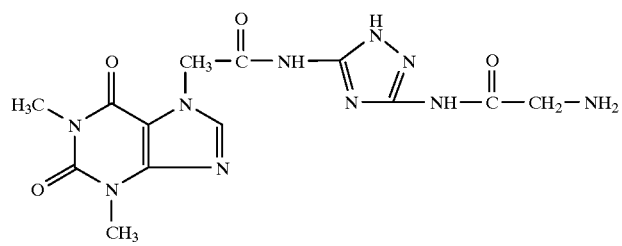
(213) 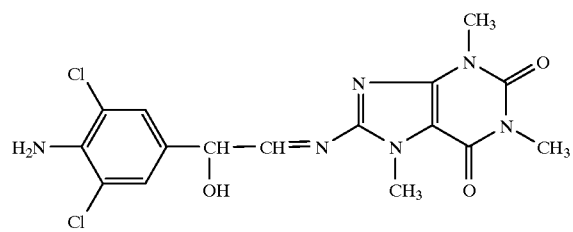
(214) 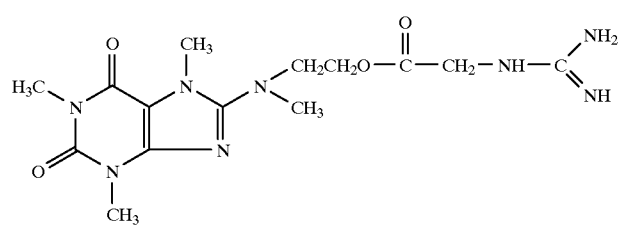

TABLE I-continued
(215) 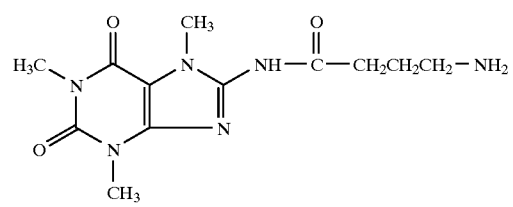
(216) 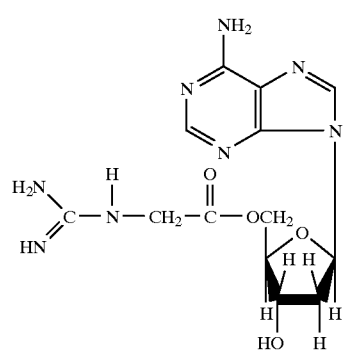
(217) Chlorguanide Merck (111th Ed.) p. 2084
(218) 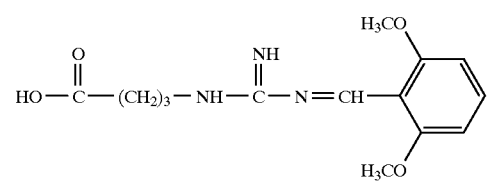
(219) 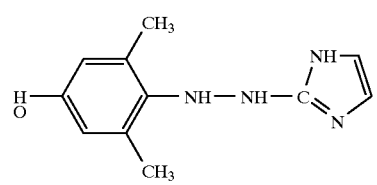
(220) 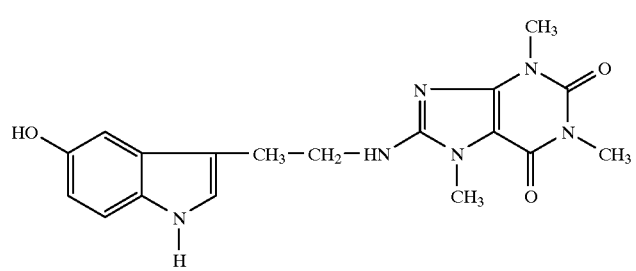
(221) 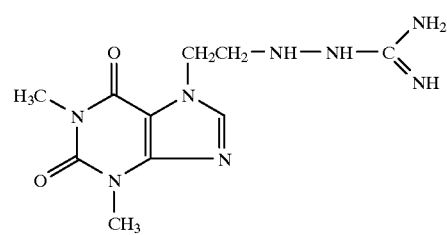

TABLE I-continued
(222)
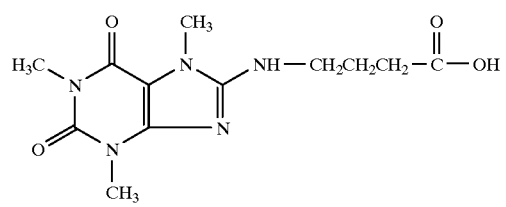
(223)
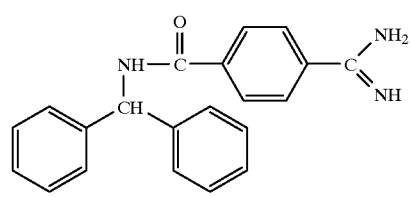
(224)
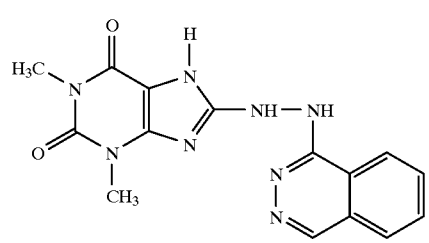
(225)
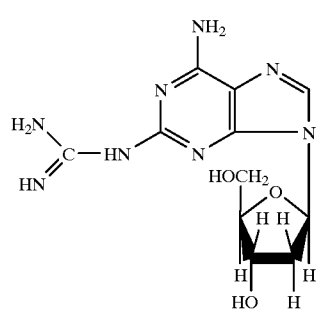
(226)
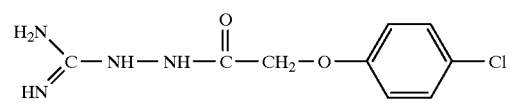
(227)
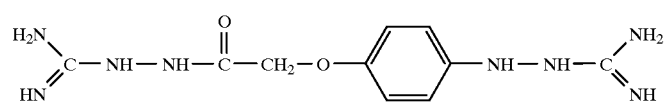
(228)
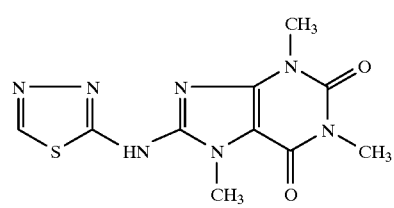

TABLE I-continued
(229)
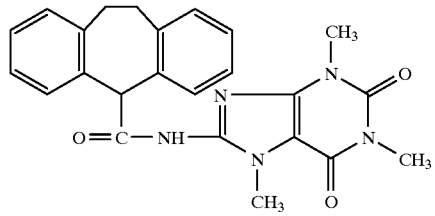
(230)
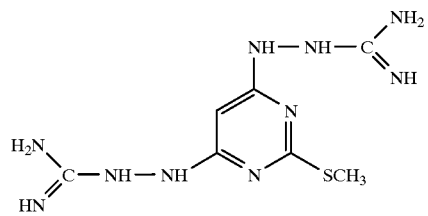
(231)
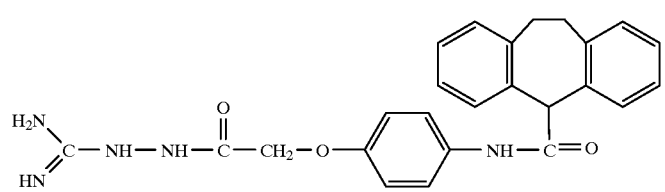
(232)
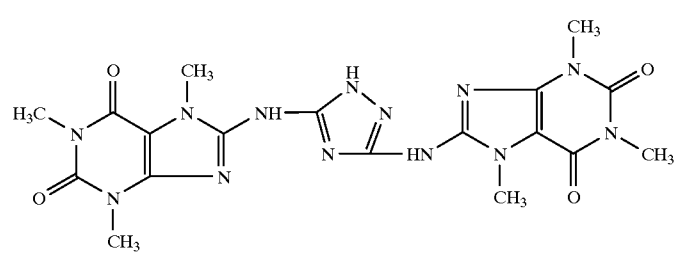
(233)
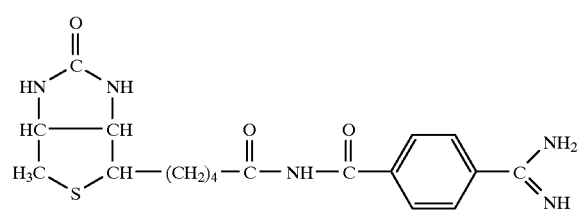
(234)
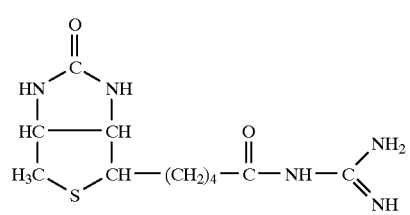
Table II presents the chemical reactants for the preparation of the exemplary novel compounds of this invention listed in Table I, being numbered in parallel to the numbering of Table I. The products in Tables I and II are prepared according to the method described for preparing such compounds in accordance with this invention.

TABLE II

| Reactants | Product |
|---|---|
| (1) 2,6-Dichlorobenzoic acid + Aminoguanidine | 2,6-Dichlorobenzamidoguanidine |
| (2) 2,6-Dichlorobenzoic acid + 2-Hydrazinoimidazole | 2-(2,6-Dichlorobenzamido)-2-amino-imidazole |
| (3) 4-Methylbenzaldehyde(2 mols) + Guanidine | Bis-(4-methylbenzylidene)-guanidine |
| (4) 2,6-Dichlorobenzaldehyde(2 mols) + 5-Hydroxyindole-3-acetaldehyde + Melamine | 2,4-Bis-(2,6-dichlorobenzylideneamino)-6-(5-hydroxyindole-3-ethylamino)-1,3,5-s-triazine |
| (5) 5-Hydroxy-3-indole acetic acid + 1-Naphthylacetic acid + Melamine | 2-(Amino)-4-(5-hydroxyindole-3-acetamido)-6-(1-naphthylacetamido)-1,3,5-s-triazine |
| (6) 2-Hydroxybenzoic acid methyl ester + Guanidinoacetic acid | 2-(Guanidinoacetoxy)-1-methylbenzoic acid ester |
| (7) 2,6-Dichlorobenzaldehyde + 3,4-Dihydroxymandelic aldehyde + Melamine | 2-(Amino)-4-(2,6-dichlorobenzylideneamino)-6- (3,4-dihydroxyphenyl-7-(R) or 7-(S)-hydroxyethyleneamino)-1,3,5-s-Triazine |
| (8) 2,6-Dichlorobenzaldehyde(2 mols) + 3,4-Dihydroxyphenylacet-aldehyde + Melamine | 2,4-Bis-(2,6-dichlorobenzylideneamino)-6-(3,4-dihydroxyphenylethylamino)-1,3,5-s-triazine |
| (9) 2-Acetoxybenzoic acid + 3,5-Dichlorophenylacetic acid + Melamine | 2-(Amino)-4-(2-acetoxybenzamido)-6-(3,5-dichlorophenylacetamido)-1,3,5-s-triazine |
| (10) Aminoguanidine + 2-Acetoxybenzaldehyde | 2-Acetoxybenzylideneaminoguanidine |
| (11) 2,4-Dichlorophenoxybutyric acid | |

TABLE II-continued

| Reactants | Product |
|---|---|
| +<br>Guanidine | 2,4-Dichlorophenoxybutyramidoamidine |
| (12)<br>4-Chlorobenzaldehyde(2 mols)<br>+<br>Melamine | 2-(Amino)-4,6-bis-(4-chlorobenzyl-ideneamino)-1,3,5-s-triazine |
| (13)<br>3,4,5-Trimethoxybenz-aldehyde<br>+<br>2-Hydrazinoimidazole | 2-(3,4,5-Trimethoxybenzylideneamino)-2-aminoimidazole |
| (14)<br>2,6-Dichlorobenzaldehyde<br>+<br>4-Aminobutyric acid<br>+<br>Melamine | 2-(Amino)-4-(4-aminobutyramido)-6-(2,6-dichlorobenzylideneamino)-1,3,5-s-triazine |
| (15)<br>Phenylactic acid<br>+<br>2-Hydrazinoimidazole | 2-(Phenylacetamido)-2-aminoimidazole |
| (16)<br>2,6-Dichlorobenzaldehyde<br>+<br>Guanidine | 2,6-(Dichlorobenzylideneamino)-amidine |
| (17)<br>2,6-Dichlorobenzaldehyde(2 mols)<br>+<br>Melamine | 2-(Amino)-4-6-bis-(2,6-dichlorobenzyl-ideneamino)-1,3,5-s-triazine |
| (18)<br>2,6-Dichlorobenzylaldehyde(3 mols)<br>+<br>Melamine | 2,4,6-tris-(2,6-Dichlorobenzyl ideneamino)-1,3,5-s-triazine |
| (19)<br>4-Hydroxy-3-methoxy-phenylacetic acid(2 mols)<br>+<br>Melamine | 2-(Amino)-4,6-bis-(4-hydroxy-3-methoxyphenylacetamido)-1,3,5-s-triazine |
| (20)<br>1-Naphthaldehyde(3 mols)<br>+<br>Melamine | 2,4,6-Tris-(1-naphthylmethyleneimino)-1,3,5-s-triazine |
| (21)<br>2,4-Diamino-6-phenyl-1,3,5-s-triazine(2 mols)<br>+<br>2,6-Dichlorobenzaldehyde(2 mols) | 2,4-Bis-(2,6-dichlorobenzylideneamino)-6(phenyl)-1,3,5-s-triazine |
| (22)<br>2,4-Dichlorophenoxy-butyric Acid(2 mols)<br>+<br>Melamine | 2-(Amino)-4,6-bis-(2,4-dichlorophenoxy-butyramido)-1,3,5-s-triazine |
| (23)<br>2,6-Dichlorobenzaldehyde<br>+ | |

TABLE II-continued

| Reactants | Product |
|---|---|
| Theophylline-7-acetic acid<br>+<br>2-Acetoxybenzoic acid<br>+<br>Melamine | 2-(Acetoxybenzamido)-4-(2,6-dichloro-benzylideneamino)-6-(theophylline-7-acetamido)-1,3,5-s-triazine |
| (24)<br>3,4,5-Trimethoxybenz-aldehyde (2 mols)<br>+<br>Melamine | 2-(Amino)-4,6-bis-(3,4,5-trimethoxy-benzylideneamino)-1,3,5-s-triazine |
| (25)<br>2-(Hydrazino)-4,6-bis(diethylamino)-1,3,5-s-triazine<br>+<br>3,4,5-Trimethoxy-benzaldehyde | 2,4-Bis-(diethylamino)-6-(3,4,5-trimethoxybenzylidenehydrazino)-1,3,5-s-triazine |
| (26)<br>N-(4-Hydroxyphenyl)-acetamide<br>+<br>Guanidinoacetic acid | N-(4-Guanidinoacetoxy)-acetanilide |
| (27)<br>Hydralazine<br>+<br>Guanidinoacetic acid | N-(Guanidinoacetamido)-1-amino-phthalazine |
| (28)<br>5-Hydroxytryptamine<br>+<br>2,6-Dichlorobenzaldehyde<br>+<br>Guanidinoacetic acid | N-(2,6-Dichlorobenzylidene)-5-guanidinoacetoxy)-indole-3-ethylamine |
| (29)<br>3,4-Dihydroxyphenyl acetaldehyde<br>+<br>5-Hydroxyindole-3-acetaldehyde<br>+<br>2,6-Dichlorobenzaldehyde<br>+<br>Melamine | 2-(2,6-Dichlorobenzylideneamino)-4-(3,4-dihydroxyphenylethylamino)-6-(5-hydroxyindole-3-ethylamino)-1,3,5-s-triazine |
| (30)<br>1-Naphthylacetic acid (3 mols)<br>+<br>Melamine | 2,4,6-Tris(1-naphthylacetamido)-1,3,5-s-triazine |
| (31)<br>Betaine<br>+<br>Theophylline-7-acetic acid<br>+<br>Melamine | 2-(Amino)-4-(1-carboxamido-N,N,N-trimethylmethaniminium)-6-(theophylline-7-acetamido)-1,3,5-s-triazine |
| (32)<br>Guanidinoacetic acid<br>+ | |

TABLE II-continued

| Reactants | Product |
| --- | --- |
| Choline | Guanidinoacetylcholine HcL;1-(2-hydroxy-N,N,N-trimethylethanaminium-1-guanidinoacetate ester |
| (33) Guanidinoacetic acid + 3-Methyl-1-butanol | 1-Guanidinoacetoxy-3-methyl-1-butanol |
| (34) Glycerol + Guanidinoacetic acid (3 mols) | 1,2,3-Propanetrioltriguanidino acetate ester; 1,2,3-tris-(guanidinoacetoxy) propane |
| (35) 2-Guanidinobenzimadazole + Theophylline-7-acetic acid | 2-(Theophylline-7-acetamido)-2-amino-benzimidazole |
| (36) Nicotinic acid + Theophylline-7-acetic acid + Melamine | 2-Amino-4-(nicotinamido)-6-(theophylline-7-acetamido)-1,3,5-s-triazine |
| (37) 5-Hydroxyindole-3-acetaldehyde + 2-Guanidinobenzimidazole | 2-(5-Hydroxyindole-3-ethylamino)-2-amidinobenzimidazole |
| (38) Aminoguanidine + 5-Hydroxyindole-3-acetic acid | 5-Hydroxyindole-3-acetamidoguanidine |
| (39) 6-Aminohexanoic acid + Theophylline-7-acetic acid + Melamine | 2-(Amino)-4-(6-aminohexanamido)-6-theophylline-7-acetamido)-1,3,5-s-triazine |
| (40) 2-Acetoxybenzoic acid + Theophylline-7-acetic acid + Melamine | 2-(Amino)-4-(2-acetoxybenzamido)-6-(theophylline-7-acetamido)-1,3,5-s-triazine |
| (41) Aminoguanidine + 2,4-Dichlorophenoxy-butyric acid | 2,4-(Dichlorophenoxybutyramido)-guanidine |
| (42) 2-Guanidinobenzimidazole + 2-Naphthoxyacetic acid | 2-(2-Naphthoxyacetamido)-2-amidino-benzimidazole |
| (43) 2,6-Di-tert-butyl-4- | |

TABLE II-continued

| Reactants | Product |
|---|---|
| methylphenol<br>+<br>Guanidinoacetic acid | 1-Guanidinoacetoxy-2,6-di-tert-butyl-4-methylphenol |
| (44)<br>3,4-Dihydroxymandelic aldehyde<br>+<br>2,6-Dichlorobenzaldhyde<br>+<br>Aminoguanidine | N-(2,6-Dichlorobenzylideneguanidino)-2-(3,4-dihydroxyphenyl)-2-(R) or-2-(S)-hydroxyethylimine |
| (45)<br>3,4-Dihydroxyphenyl-acetaldehyde<br>+<br>Aminoguanidine | 3,4-Dihydroxyphenylethylene aminoguanidine |
| (46)<br>2-Aminobenzothiazole<br>+<br>2,6-Dichlorobenzaldehyde | 2-(2,6-Dichlorobenzylideneamino)-benzothiazole |
| (47)<br>Melamine<br>+<br>Nicotinic acid<br>+<br>3,4,5-Trimethoxyphenyl-acetic acid | 2-(Amino)-4-(nicotinamido)-6-(3,4,5-trimethoxyacetamido)-1,3,5-s-triazine |
| (48)<br>L-5-Hydroxytryptophan<br>+<br>2,6-Dichlorobenzaldehyde<br>+<br>Aminoguanidine | 3-(5-Hydroxyindole)-2-(R)-or-2-(S)-(2,6-dichlorbenzylideneamino)-N-guanidinopropionamide |
| (49)<br>Guanidinoacetic acid<br>+<br>Nicotinyl alcohol | 3-(guanidinoacetoxy)-3-methylpyridine |
| (50)<br>L-3,4-Dihydroxyphenylalanine<br>+<br>2,6-Dichlorobenzaldehyde<br>+<br>Aminoguanidine | 3-(3,4-Dihydroxyphenyl)-2-(R)-or-2-(S)-(2,6-dichlorbenzylideneamino)-N-guanidinopropionamide |
| (51)<br>Aminoguanidine<br>+<br>2,6-Dichlorophenylacetic acid | 2,6-Dichlorophenylacetamidoguanidine |
| (52)<br>2-Hydrazinoimidazole<br>+<br>Indole-3-carboxaldehyde | 2-(Indole-3-methylene)-2-hydrazinoimidazole |
| (53)<br>Theobromine-1-acetic acid<br>+<br>Aminoguanidine | Theobromine-1-acetamido-guanidine |

TABLE II-continued

| Reactants | Product |
|---|---|
| (54)<br>1-Theobromineacetic acid<br>+<br>Nicotinic acid<br>+<br>Melamine | 2-(Amino)-4-(nicotinamido)-6-<br>(theobromine-1-acetamido)-1,3,5-s-<br>triazine |
| (55)<br>4-Aminobutyric acid<br>+<br>Guanidinoacetic acid | 4-(Guanidinoacetamido)butyric acid |
| (56)<br>3,4-Dimethoxybenzoic acid<br>+<br>2,6-Dichloroacetic acid<br>+<br>Melamine | 2-(Amino)-4-(2,6-dichloroacetamido)-6-<br>(3,4-dimethoxybenzamido)-1,3,5-s-<br>triazine |
| (57)<br>1-Theobromineacetic acid<br>+<br>2,6-Dichlorophenylacetic acid<br>+<br>Melamine | 2-(Amino)-4-(2,6-dichlorophenyl-<br>acetamido)-6-(theobromine-1-acetamido)-<br>1,3,5-s-triazine |
| (58)<br>Glycerol<br>+<br>Guanidinoacetic acid<br>+<br>2,6-Dichlorophenylacetic acid | 1-(2,6-Dichlorophenylacetoxy)-3-<br>(guanidinoacetoxy)-2-propanol |
| (59)<br>Glycerol<br>+<br>Guanidinoacetic acid<br>+<br>4-Aminobutyric acid | 1-(4-Aminobutoxy)-3-(guanidinoacetoxy)-<br>2-propanol |
| (60)<br>Adipic (hexanedioic) acid<br>+<br>Guanidine | 1,4-Bis-(amidineamido)-butane |
| (61)<br>Adipic acid<br>+<br>Aminoguanidine | 5-Guanidinamidopentanoic acid |
| (62)<br>Guanidineacetic acid<br>+<br>1,3-Dichloro-2-propanol | 1,3-Dichloro-2-guanidinoacetoxypropane |
| (63)<br>Alpha tocopherol<br>+<br>Guanidineacetic acid | 2,5,7,8-Tetramethyl-2-(4,8,12-<br>trimethyltridecyl)-6-guanidinoacetoxy<br>chromanol |
| (64)<br>All-cis-5,8,11,14,17-<br>eicosapentaenic acid<br>(20:5, omega-3;EPA)<br>+<br>Aminoguanidine | |

TABLE II-continued

| Reactants | Product |
|---|---|
| | All-cis-5,8,11,14,17-eicosapentaenamidoguanidine |
| (65) 3,4,5-Trimethoxyphenyl-acetic acid + 5-Hydroxyindole-3-acetaldehyde + Aminoguanidine | |
| | 5-(3,4,5-Trimethoxyphenylacetoxy)-indole-3-ethyliminoguanidine |
| (66) Melamine + 3,4-Dimethoxycarbox-aldehyde (3mols) | |
| | 2,4,6-Tris-(3,4-dimethoxybenzylidene-amino)-1,3,5-s-triazine |
| (67) 2,6-Diisopropylaniline + Guanidinoacetic acid | |
| | N-(2,6-Diisopropylphenyl)-guanidinoacetamide |
| (68) 3,5-Dimethoxybenz-aldehyde (2 mols) + Melamine | |
| | 2-(Amino)-4,6-bis(3,5-dimethoxybenzyl-ideneamino)-1,3,5-s-triazine |
| (69) 2-(3,5-Dihydroxyphenyl)-2-hydroxyacetaldehyde + 2,6-Dichlorobenzaldehyde + Melamine | |
| | 2-(Amino)-4-(2,6-dichlorobenzylidene amino)-6-(3,5-dihydroxy-2-(R)-or-2-(S)-hydroxyethylamino)1,3,5-s-triazine |
| (70) Theophylline-7-acetic acid + 2,6-Dichlorbenzaldehyde + 3,5-Dihydroxymandelic-aldehyde + Melamine | |
| | 2-(2,6-Dichlorbenzylideneamino)-4-(3,5-dihydroxy-2-(R)-or-(S)-ethylimino)-6-(theophylline-7-acetamido)-1,3,5-s-triazine |
| (71) 1-Naphthylacetic acid + 2-Acetoxybenzoic acid + Melamine | |
| | 2-(Acetoxybenzamido)-4-(amino)-6-(1-naphthylacetamido)-1,3,5-s-triazine |
| (72) 3,5-Dichloroaniline + Guanidinoacetic acid + 5-Hydroxyindole-3-acetic acid | |
| | N-(3,5-Dichlorphenyl)-5-(guanidino-acetoxy)-indole-3-ethylamine |
| (73) 3,5-Dichloroaniline + Guanidinoacetic acid | |
| | N-(3,5-Dichlorphenyl)-N-guanidino-acetamide |

TABLE II-continued

| Reactants | Product |
|---|---|
| (74)<br>3,4,5-Trimethoxyphenyl-acetic acid<br>+<br>5-Hydroxytryptamine | 5-(3,4,5-Trimethoxyphenylacetoxy)-tryptamine |
| (75)<br>Aminoguanidine<br>+<br>3,5-Dihydroxy-mandelic aldehyde | 3,5-Dihydroxy-2-(R)-or-(S)-ethyl-iminoguanidine |
| (76)<br>3,5-Dihydroxymandelamine<br>+<br>2,6-Dichlorbenzaldehyde | 2-(3,5-Dihydroxyphenyl-2-(R)-or-2-(S)-hydroxyethylimino-N-(2,6-dichlorobenzylamine |
| (77)<br>3,4,5-Trimethoxyphenyl-acetic acid<br>+<br>2-Hydroxy benzylidine aminoguanidine | 2-(3,4,5-Trimethoxyphenylacetoxy)-benzylideneaminoguanidine |
| (78)<br>5-Hydroxytryptamine<br>+<br>2,6-Dichlorobenzaldehyde | N-(2,6-Dichlorbenzylidene)-3-(5-hydroxyindole)ethylamine |
| (79)<br>2-Hydroxybenzoic acid<br>+<br>Aminoguanidine | 2-(Hydroxybenzamido)-guanidine |
| (80)<br>2-Hydroxybenzoic acid<br>+<br>Aminoguanidine<br>+<br>Guanidonoacetic acid | 2-(Guanidinoacetoxybenzamido)-guanidine |
| (81)<br>2-Acetoxybenzoic acid<br>+<br>Aminoguanidine | 2-Acetoxybenzoylaminoguanidine |
| (82)<br>2-Hydroxybenzamidoguanidine<br>+<br>Theophylline-7-acetic acid | 2-(Theophyiline-7-acetoxy)-benzamidoguanidine |
| (83)<br>2-Hydroxybenzoic acid<br>+<br>Theophylline-7-acetic acid | 2-(Theophylline-7-acetoxy)-benzoic acid |
| (84)<br>3,5-Dichloro-2-hydroxy-benzylideneaminoguanidine<br>+<br>Theophylline-7-acetic acid | 3,5-Dichloro-2-(theophylline-7-acetoxy)-benzylidineaminoguanidine |
| (85)<br>L-Histidine + 2-Hydrazinoimidazole<br>+<br>2,6-Dichlorobenzaldehyde | N-(2-Aminoimidazolyl)-2-(R)-or-2-(S)-(2,6-dichlorobenzylideneamino)-4- |

TABLE II-continued

| Reactants | Product |
|---|---|
| | imidazolylpropionamide |
| (86)<br>2-Propylpentanoic acid<br>+<br>Aminoguanidine | |
| | 2-Propylpentanoylaminoguanidine |
| (87)<br>$N_2,N_4,N_6$,Tris(hydroxymethyl)<br>melamine<br>+<br>3,4-Dimethoxyphenyl<br>propionic acid) (3 mols) | |
| | 2,4,6 Tris(3,4-dimethoxyphenylpropoxy<br>methylamino)-1,3,5-s-triazine |
| (88)<br>4-Ethoxyaniline<br>+<br>Guanidinoacetic Acid | |
| | 4-(4-Ethoxyphenyl)-guanidinoacetamide |
| (89)<br>2-Hydroxybenzoylhydrazine<br>+<br>Guanidinoacetic acid | |
| | 2-(Guanidinoacetoxy)-guanidino-<br>acetamidobenzamide |
| (90)<br>Aminoguanidine<br>6-Hydroxy-2,5,7,8-<br>tetramethylchroman-2-<br>carboxylic acid | |
| | 6-Hydroxy-2,5,7,8-tetramethylchromanyl<br>-2-carboxamidoguanidine |
| (91)<br>2-Hydrazinopyridine<br>+<br>Salicylic acid<br>+<br>Guanidinoacetic acid | |
| | N-(2-Aminopyridyl)-2-(guanidinoacetoxy)-<br>benzamide |
| (92)<br>2-Aminopyrimidine<br>+<br>2,6-Dichorobenzaldehyde | |
| | 2-(2,6-Dichlorobenzylideneamino)-<br>pyrimidine |
| (93)<br>2-Amino-1,3,4-thiadiazole<br>+<br>3,5-Dichlorophenylacetic<br>acid | |
| | 2-(3,5-Dichorophenylacetyl)-2-amino-<br>1,3,4-thiadiazole |
| (94)<br>3-Amino-1,2,4-triazine<br>+<br>1-Theobromineacetic acid | |
| | 3-(2,3,6,7-Tetrahydro-3,7-dimethyl-<br>2,6-dioxo-1(2H)purineacetamido)-1,2,4-<br>triazine |
| (95)<br>Aminoguanidine<br>+<br>5-Hydantoinacetic acid | |
| | 5-(Hydantoinacetamido)-guanidine |
| (96)<br>2-(Aminomethyl)benzimidazole<br>+<br>Theophylline-7-acetic acid | |
| | 2-(Theophylline-7-acetamido)-2-<br>methylbenzimidazole |
| (97)<br>Theophylline-7-acetic acid<br>+<br>4-Amidinobenzamide | |
| | 4-(Amidino)-N-(theophylline-7-acetyl)-<br>benzamide |

TABLE II-continued

| Reactants | Product |
| --- | --- |
| (98)<br>2-Imidazole carboxaldehyde<br>+<br>3,4,5-Trimethoxyaniline | 2-(3,4,5-trimeythoxyphenylaminomethyl)-imidazole |
| (99)<br>4-Amidinobenzamide<br>+<br>2,6- Dichlorophenyl-<br>acetic acid | 4-(Amidino)-N-(2,6-dichlorophenylacetyl)-benzamide |
| (100)<br>2-(Aminomethyl)benzimidazole<br>+<br>3,4,5-Trimethoxybenzaldehyde | 2-(3,4,5-Trimethoxybenzylidineamino)-2-methylbenzimidazole |
| (101)<br>2-Imidazolecarboxaldehyde<br>+<br>2,6-Diisopropylaniline | 2-(2,6-Diisopropylanilino)-2-methyleneimidazole |
| (102)<br>Theophylline-7-acetic acid<br>+<br>3,5-Dichlorophenylhydrazine | 7-(3,5-Dichorophenylhydrazido)-7-acetyltheophylline |
| (103)<br>Aminoguanidine<br>+<br>5-Methoxy-2-methyl-3-indoleacetic acid | 5-Methoxy-2-methyl-3-indoleacetamidoguanidine |
| (104)<br>Guanidinoacetic acid +<br>4-Hydroxy-3-methoxybenzylamine | N-(4-Hydroxy-3-methoxybenzyl)-guanidinoacetamide |
| (105)<br>All-cis-5,8,11,14,17-eicosapentaenoyl-aminoguanidine<br>+<br>4-Hydroxy-3-methoxyphenylacetic acid | N-(All-cis-5,8,11,14,17-eicosapentaenoylaminoamidino)-4-hydroxy-3-methoxyphenylacetamide |
| (106)<br>Guanidinoacetic acid(2 mols)<br>+<br>7-(2,3-Dihydroxypropyl)-theophylline | 7-(2,3-Diguainidinoacetoxypropyl)-theophylline |
| (107)<br>Hydralazine<br>+<br>3,4,5-Trimethoxybenzyl-idineguanidinoacetic acid | N-(3,4,5-Trimethoxybenzylideneguanidino acetyl)-1-hydrazinophthalazine |
| (108)<br>3-(3,4-Dichorophenoxy)-benzaldehyde<br>+<br>Aminoguanidine | 3-(3,4-Dichorophenoxy)-benzylidene aminoguanidine |
| (109)<br>3,4-Dichorophenylacetaldehyde<br>+ | |

TABLE II-continued

| Reactants | Product |
|---|---|
| Aminoguanidine<br>(110)<br>6-Hydroxy-2,5,7,8-<br>tetramethylchroman-2-<br>carboxylic acid (3 mols)<br>+<br>$N_2,N_4,N_6$-Tris-(hydroxymethyl)-<br>melamine | 3,4-Dichorophenylethylaminoguanidine<br><br>2,4,6-Tris-(6-hydroxy-2,5,7,8-<br>tetramethylchroman-2-carbonylmethyl<br>amino)-1,3,5,s-triazine |
| (111)<br>Guanidine<br>+<br>3,4,5-Trimethoxy-<br>benzaldehyde(2 mols) | N,N'-Bis-(3,4,5-trimethoxybenzylidene)<br>guanidine |
| (112)<br>5-Methoxyindole-3-<br>ethylamine<br>+<br>3,4,5-Trimethoxyphenyl-<br>acetic acid | 5-(Methoxy)-N-(3,4,5-trimethoxy-<br>phenylacetyl)-tryptamine |
| (113)<br>Guanidine<br>+<br>Theophylline-7-acetic acid | N,N'-Bis-(theophylline-7-acetyl)-<br>guanidine |
| (114)<br>Guanidine<br>+<br>6-Hydroxy-2,5,7,8-<br>tetramethylchroman-<br>2-carboxylic acid | N,N'-Bis-(6-hydroxy-2,5,7,8-<br>tetramethylchroman-2-carbonyl)-guanidine |
| (115)<br>Aminoguanidine<br>+<br>3,4,5-Trimethoxyphenyl-<br>propionic acid | N-(Guanidino)-3-(3,4,5-trimethoxy-<br>phenyl)-propionamide |
| (116)<br>Theophylline-7-acetylguanidine<br>+<br>6-Hydroxy-2,5,7,8-tetramethylchroman-<br>2-carboxylic acid | N-(6-Hydroxy-2,5,7,8-tetramethylchroman-<br>2-carbonyl)-N'-(theophylline-7-acetyl)-<br>guanidine |
| (117)<br>6-Hydroxy-2,5,7,8-<br>tetramethylchroman-2-<br>carboxylic acid<br>+<br>Guanidinoacetic acid | 6-(Guanidinoacetoxy)-2,5,7,8-<br>tetramethylchroman-2-carboxylic acid |
| (118)<br>5-Hydroxyindole-3-<br>ethylaminoguanidine<br>+<br>6-Hydroxy-2,5,7,8-<br>tetramethylchroman-2-<br>carboxylic acid | 5-(6-Hydroxy-2,5,7,8-tetramethylchroman-<br>2-carbonyl)-5-hydroxyindole-3-ethyl-<br>iminoguanidine |
| (119)<br>6-Hydroxy-2,5,7,8-<br>tetramethylchroman-2- | |

TABLE II-continued

| Reactants | Product |
|---|---|
| carboxylic acid<br>+<br>1-Guanidinoacetoxy-2,3-propanediol | 1-Guanidinoacetoxy-3-(6-hydroxy-2,5,7,8-tetramethylchroman-2-carbonyl)-2-propanol |
| (120)<br>2,4-Bis-(amino)-6-(4-aminobutyramido)-1,2,3-s-triazine<br>+<br>6-Hydroxy-2,5,7,8-tetramethylchroman-2-carboxylic acid<br>+<br>Theophylline-7-acetic acid | 2-(4-Aminobutyramido)-4-(6-hydroxy-2,5,7,8-tetramethylchroman-2-carboxamido)-6-(theophylline-7-acetamido)-1,2,3-s-triazine |
| (121)<br>Theophylline-7-acetic acid<br>+<br>6-Hydroxy-2,5,7,8-tetramethylchroman-2-carboxylic acid | 7-(6-Hydroxy-2,5,7,8-tetramethylchroman-2-carbonyl)-7-acetyltheophylline |
| (122)<br>Theophylline-7-acetic acid<br>+<br>2-(4-Aminophenyl)-6-methylbenzothiazole | 6-(Methyl)-2-(4-theophylline-7-acetamido phenyl)-2-benzothiazole |
| (123)<br>2-Amino-5-nitropyrimidine<br>+<br>6-Hydroxy-2,5,7,8-tetramethyl-chroman-2-carboxylic acid | 2-(6-Hydroxy-2,5,7,8-tetramethylchroman-2-carboxamido)-5-nitropyrimidine |
| (124)<br>6-(Guanidinoacetoxy)2,5,7,8-tetramethylchroman-2-carboxylic acid<br>+<br>2-Aminopyridine | 2-(6-Guanidinoacetoxy)-2,5,7,8-tetramethylchroman-2-carboxamido-2-pyridine |
| (125)<br>6-(Guanidinoacetoxy)2,5,7,8-tetramethylchroman-2-carboxylic acid<br>+<br>4-Aminopyridine | 4-(6-Guanidinoacetoxy)-2,5,7,8-tetramethylchroman-2-carboxamido-4-pyridine |
| (126)<br>4-Aminopyridine<br>+<br>Guanidinoacetic acid | 4-(Guanidinoacetamido)-pyridine |
| (127)<br>Guanidinoacetic acid (2 mols)<br>+<br>Diethylstilbestrol | 4,4'-(1,2-Diethyl-1,2-ethenediyl)bis-phenoldiguanidinoacetate ester |
| (128)<br>6-(Guanidinoacetoxy)-2,5,7,8-tetramethylchroman-2-carboxylic acid<br>+<br>Dietheylstilbestrol | 2-[4,4'-(1,2-Diethyl-1,2-ethenediyl) |

TABLE II-continued

| Reactants | Product |
|---|---|
| | phenol]-6-(guanidinoacetoxy)-2,5,7,8-tetramethylchroman-2-carbonyl-2-phenol ester |
| (129)<br>6-Chloro-1,2-dihydro-17-hydroxy-3'H-cyclopropa[1,2]Pregna-1,4,6-triene-3,20-dione + guanidino acetic acid | |
| | 6-Chloro-1,2,Dihydro-17-guanidino-acetoxy-3'H-cyclopropa[1,2]pregna-1,4,6-triene-3,20-dione |
| (130)<br>2-Hydroxybenzoic Acid<br>+<br>Guanidinoacetic acid | |
| | 2-Guanidinoacetoxybenzoic acid |
| (131)<br>2-Hydroxybenzoic acid<br>+<br>6-(Guanidinoacetoxy)-2,5,7,8-tetramethylchroman -2-carboxylic acid | |
| | 2-[6(guanidinoacetoxy)-2,5,7,8-tetramethylchroman-2-carbonyl]-2-benzoic acid ester |
| (132)<br>6-Chloro-1,2-dihydro-17-hydroxy-3'H-cyclopropa[1,2]pregna-1,4,6-triene-3,20-dione<br>+<br>6-Hydroxy-2,5,7,8-tetramethylchroman-2-carboxylic acid | |
| | 2-(6-Chloro-1,2-dihydro-17-hydroxy-3'H-cyclopropa[1,2]pregna-1,4,6-triene-3,20-dione)-2-(6-hydroxy-2,5,7,8-tetramethyl-chroman)-2-carboxylic acid ester |
| (133)<br>6-Hydroxy-2,5,7,8-tetramethyl-chroman-2-carboxylic acid<br>+<br>N-Guanidinoacetamido-1-aminophthalazine | |
| | N-(6-Hydroxy-2,5,7,8-tetramethylchroman-2-carboxamido)-N-amidinoacetamido-1-aminophthalazine |
| (134)<br>Cyproteronesuccinate(Na+)<br>+<br>Hydralazine | |
| | 17-(Cyproteronesuccinamido)-17-amino-phthalazine |
| (135)<br>4-Aminobenzamido-guanidine<br>+<br>6-Hydroxy-2,5,7,8-tetramethyl-chroman-2-carboxylic acid | |
| | 4-N-(6-Hydroxy-2,5,7,8-tetramethyl-chroman-2-carboxamido)-4-benzamidoguanidine |
| (136)<br>5-(Amino)-3,5-dideoxy-D-glycero-D-galacto-2-nonulosonic acid<br>+<br>Guanidinoacetic acid | |
| | 5-(guanidinoacetamido)-3,5-dideoxy-D-glycero-D-galacto-2-nonulosonic acid |
| (137)<br>Alpha-D-glucose<br>+<br>Aminoguanidine | |
| | Alpha-D-glucosyl-1-aminoguanidine |
| (138)<br>Guanidineacetic acid<br>+<br>6-Hydroxy-2,5,7,8-tetramethyl- | |

TABLE II-continued

| Reactants | Product |
| --- | --- |
| chroman-2-carboxylic acid<br>+<br>Theophylline-7-acetoc acid | 6-(Theophylline-7-acetoxy)-2-5-7-8-tetramethylchroman-2-carbox-amidoguanidine |
| (139)<br>6-(Guanidinoacetoxy)-2,5,7,8-tetramethylchroman-2-carboxylic acid<br>+<br>Salycylic acid | 2-[6-(Guanidinoacetoxy)-2,5,7,8-tetramethylchroman-2-carbonyl]-2-hydroxybenzoicacid ester |
| (140)<br>2-(6-Chloro-1,2-dihydro-17-hydroxy-3'-H-cyclopropa[1,2]pregna-1,4,6-triene-3,20-dione)-6-(hydroxy-2,5,7,8-tetramethyl-chroman-2-carboxylic acid ester<br>+<br>1-(Succinamido)-1--aminophthalazine | 17-[2-6-(N-1-Aminophthalazino-1-amido-propionyl)-2,5,7,8-tetramethylchroman-2-carbonyl]-17-cyproterone ester |
| (141)<br>6-(Guanidinoacetoxy)-2,5,7,8-tetramethylchroman-2-carboxylic acid<br>+<br>Cyproterone | 17-[6-(Guanidinoacetoxy)-2,5,7,8-tetramethylchroman-2-carbonyl]-17-cyproterone ester |
| (142)<br>3,5-Dichloro-2-hydroxy-benzylideneaminoguanidine<br>+<br>6-Hydroxy-2,5,7,8-tetramethyl-chroman-2-carboxylic acid | 2-[(6-Hydroxy-2,5,7,8-tetramethyl-chroman-2-carbonyl)-2-(3,5-dichloro-2-oxybenzylidene]-aminoguanidine ester |
| (143)<br>4,4'-(1,2-Diethyl-1,2-ethenediyl)-4'-guanidinoacetoxy-phenyl-4'-phenol<br>+<br>6-Hydroxy-2,5,7,8-tetramethyl-chroman-2-carboxylic acid | 4-4'-(1,2-Diethyl-1,2-ethenediyl)-4-guanidinoacetoxyphenyl-4'-(6-hydroxy-2,5,7,8-tetramethylchroman-2-carbonyl)-phenol ester |
| (144)<br>Testosterone<br>+<br>Guanidinoacetic acid | 17-Guanidinoacetoxytestosterone |
| (145)<br>Aminoguanidine<br>+<br>2-Acetoxy-3,5-dichloro-benzaldehyde | 2-Acetoxy-3-5-dichlorobenzylidene-aminoguanidine |
| (146)<br>Testosterone<br>+<br>6-Guanidinoacetoxy-2,5,7,8-tetramethylchroman-2-carboxylic acid | 17-(6-Guanidinoacetoxy-2,5,7,8-tetramethylchroman-2-carbonyl)-testosterone ester |

TABLE II-continued

| Reactants | Product |
| --- | --- |
| (147)<br>Estradiaol<br>+<br>Ganidineacetic acid | Bis(3,17-guanidinoacetoxy)estradiaole |
| (148)<br>Estrone<br>+<br>Guanidineacetic acid | 3-(Guanidinoacetoxy)-estrone |
| (149)<br>6-Guanidinoacetoxy-2,5,7,8-tetramethylchroman-2-carboxylic acid + estrone | 3-(6-Guanidinoacetoxy-2,5,7,8-tetramethylchroman-2-carbonyl)-3-estrone ester |
| (150)<br>5-Guanidinamidopentanoic acid<br>+<br>2,6-Di-tert-butyl-4-methylphenol | 1-(5-Guanidinamidopentanoyl)-2,6-di-tert-butyl-4-methylphenol ester |
| (151)<br>Prostaglandin $G_1$(PGE$_1$<br>aminoguanidine | N-(PGE$_1$carboxamido)-guanidine |
| (152)<br>PGE$_1$ + hydralazine | N-(PGE$_1$carboxamido)-1-aminophthalazine |
| (153)<br>6-(PGE$_1$carboxy)-2,5,7,8-tetramethylchroman-2-carboxylic acid<br>+<br>Hydralazine | N-[(6-PGE$_1$carbonyl)-2,5,7,8-tetramethyl-chroman-2-carboxamido]-1-aminophthlazine |
| (154)<br>Cyproterone + PGE$_1$ | 17-(PGE$_1$carbonyl)-17-cyproterone ester |
| (155)<br>Testosterone<br>+<br>PGE$_1$ | 17-(PGE$_1$carbonyl)-17-testosterone ester |
| (156)<br>Estrone + PGE$_2$ | 3-(PGE$_2$carbonyl)-3-estrone ester |
| (157)<br>PGE$_2$+ 4,4'-(1,2-diethyl-1,2-ethenediyl)bis-phenol | 4-(PGE$_2$carbonylphenyl)-4-4'(1,2-diethyl-1,2-ethenediyl)-4-phenol |
| (158)<br>Estradiol + PGE$_2$ | Bis(3,17-PGE$_2$carbonyl)-estradiole ester |
| (159)<br>1-(Guanidinoacetoxy)-2,3-propanediol<br>+<br>Theophylline-7-acetic acid | 1-(Guanidinoacetoxy)-3-(theophylline-7-acetoxy)-2-propanol |
| (160)<br>4-Aminobutyric acid<br>+<br>4-isopropylbenzaldehyde | 4-N-(4-Isopropylbenzylideneamino)-4-butyric acid |
| (161)<br>Hydralazine<br>+<br>3,4,5-Trimethoxybenzaldehyde | N-(3,4,5-Trimethoxyethyleneamino)-1-aminophthalazine |

TABLE II-continued

| Reactants | Product |
|---|---|
| (162)<br>2-Methylaminobenzimidazole<br>+<br>2,6-Dichlorobenzaldehyde | 2-(2,6-Dichlorobenzylideneamino)-2-methyl-benzimidazole |
| (163)<br>Aminomethylamidine<br>+<br>2-6-Diisopropylbenzaldehyde | 2,6-Diisopropylbenzylideneamino methylamidine |
| (164)<br>Ethylenediamine<br>+<br>Theophylline-7-acetic acid (2 mols) | 1,2-Bis(theophylline-7-acetamido)-ethane |
| (165)<br>3,4,5-Trimethoxyphenyl-butyric acid<br>+<br>Hydralazine | N-(3,4,5-Trimethoxyphenylbutyramido)-1-aminophthalazine |
| (166)<br>Hydralazine<br>+<br>All-cis-5,8,11,14,17-eicosapentaenoic acid | N-(All-cis-5,8,11,14,17-eicosapentaenoyl-amino)-1-aminophthalazine |
| (167)<br>Guanidineamido-carbonylpentanoic acid<br>+<br>Choline | Guanidinamidocarbonyl-1-cholinepentanoic acid ester |
| (168)<br>1-3-Dinitro-2-propanol<br>+<br>Guanidineacetic acid | 1,3-Dinitro-2-guanidinoacetoxypropane |
| (169)<br>2,6-Diisopropylanillin<br>+<br>Indole-3-carboxaldehyde | N-(Indole-3-methylene)-2,6-diisopropyl-anillin |
| (170)<br>Glycerol + $PGE_1$ (2 mols) | 1,3-Di-$PGE_1$-2-propanol-ester |
| (171)<br>4-(3,5-Dichlorobenzylidine-amino)benzoic acid<br>+<br>Aminoguanidine | 4-N-(3,5-Dichlorobenzylidineamino)-1-guanidinobenzamide |
| (172)<br>6-(Guanidinoacetoxy)-2,5,7,8-tetramethylchroman-2-carboxylic acid<br>+<br>4-Aminobutyric acid | 4-N-(6-Guanidinoacetoxy)-2,5,7,8-tetra-methylchroman-2-carboxamido)-4-butyric acid |
| (173)<br>Aminoguanidine<br>+<br>2-(All-cis-5,8,11,14,17-eicosapentaenoyloxy)-benzoic acid | 2-(All-cis-5,8,11,14,17-eicosapentaenoyl)-2-oxy-1-(guanidino)- |

TABLE II-continued

| Reactants | Product |
|---|---|
| | benzamide |
| (174) Glycerol + All-cis-5,8,11,14,17-eicosapentaenoic acid (2 mols) | 1,3-Bis-(all-cis-5,8,11,14,17-eicosapentaenoyloxy)-2-propanol |
| (175) Melamine + All-cis-5,8,11,14,17-eicosapentaenoic acid (3 mols) | 2,4,6-Tris(-all cis-5,8,11,14,17-eicosapentaeneamido)-1,3,5-s-triazine |
| (176) L-Arginine + 2,6-Disopropylaniline | N-(-2,6-Diisopropylphenyl)-L-arginineamide |
| (177) 2,4,6-Trimethoxybenzaldehyde + Aminoguanidine | 2,4,6-Trimethoxybenzylidineamino-guanidine |
| (178) Guanidineacetic acid + 2,6-Dimethylaniline | N-(2,6-Dimethylphenyl)-guanidino-acetamide |
| (179) Guanidine + All-cis-5,8,11,14,17-eicosapentaenoic acid (2 mols) | Bis-N,N'-(all-cis-5,8,11,14,17-eicosapentaenoylamino)-imine |
| (180) Hydralazine + Guanidinoacetic acid | N-(Guanidinoacetamido)-1-aminophthlazine |
| (181) 2-Amino-5-ethyl-1,3,4-thiadiazole + 2,6-Dichlorobenzaldehyde | 2-(2,6-Dichlorobenzylideneamino)-5-ethyl-1,3,4-thiadiazole |
| (182) 2,6-Dichlorobenzylidene-aminoguanidine + Theophylline-7-acetic acid | N-(2,6-Dichlorobenzylideneamino)-N'-(theophylline-7-acetyl)-guanidine |
| (183) 2-(3,4-Dihydroxyphenyl)-2-hydroxyacetaldehyde + Trolox-guanidineamide | N-(6-Hydroxy-2,5,7,8-tetramethylchroman-2-carbonyl)N'-(3,4-dihydroxyphenyl)-2-(R)-or-2-(S)-hydroxyethylguanidine |
| (184) Megosterol + Guanidinoacetate | 17-(Guanidinoacetoxy)-megostrol |
| (185) Medroxyprogesterone + Guanidinoacetic acid | 17-(Guanidinoacetoxy)-medroxy- |

TABLE II-continued

| Reactants | Product |
| --- | --- |
| | progesterone |
| (186)<br>Hydroxyprogesterone<br>+<br>Guanidinoacetic acid | |
| | 17-(Guanidinoacetoxy)-progesterone |
| (187)<br>[Z]-2-[4-(1,2-Diphenyl-<br>1-butenyl)-phenol<br>+<br>Guanidinoacetic acid | |
| | [Z]-2-[4-(1,2-Diphenyl-1-butenyl)-<br>phenoxy]-guanidineacetate ester |
| (188)<br>2-Guanidinobenzimidazol<br>+<br>Indole-3-carboxaldehyde | |
| | 2-(Indole-3-methyleneamino)-2-<br>amidinobenzimidazol |
| (189)<br>Phenylacetic Acid<br>+<br>Guanidine | |
| | Phenylacetamidoamididine |
| (190)<br>1,4-Diguanidinobutane<br>(Commercially available product as arcaine) | |
| (191)<br>2,6-Dichlorobenzaldehyde<br>+<br>3,7-Dihydro-8-amino-<br>1,3,7-trimethyl-1H-<br>purine-2,6-dione | |
| | 3,7-Dihydro-8-(2,6-dichlorobenzylidene<br>amino)-1,3,7-trimethyl-1H-purine-2,6-<br>dione |
| (192)<br>4,4'-[Pentanediylbis(oxy)]<br>bis-benzenecarboximidamide<br>(Commercially available as pentamidine) | |
| (193)<br>Cytosine + 2,6-Dichlorobenzaldehyde | |
| | 4-N-(2,6-Dichlorobenzylideneamino)-2-<br>oxypyrimidine |
| (194)<br>3,4,5-Trimethoxybenzaldehyde<br>+<br>3,5-Diamino-1,2,4-triazole | |
| | 3,5-Bis(3,4,5-trimethoxybenzylidene<br>amino)-1,2,4-triazole |
| (195)<br>Trolox<br>+<br>3,5-Diamino-1,2,4-triazole | |
| | 3,5-Bis-(6-hydroxy-2,5,7,8-tetramethyl-<br>chroman-2-carboxamido)-1,2,4 triazole |
| (196)<br>5-Hydroxyindole-3-acetaldhyde<br>+<br>3,4,5-Trimethoxybenaldehyde<br>+<br>3,5-Diamino-1,2,4-triazole | |
| | 3-(5-Hydroxyindole-3-ethylamino)-5-<br>(3,4,5-trimethoxybenzylideneamino)-<br>1,2,4-triazole |
| (197)<br>8-Aminocaffeine<br>+<br>Acetylsalicylic acid | |
| | 3,7-Dihydro-8-N-(2-acetoxybenzamido)-<br>1,3,7-trimethyl-1H-purine-2,6-dione |
| (198)<br>Cytosine +<br>D-glucose | |
| | 4-N-(1-Glucosylamino)-cytosine |
| (199)<br>Theophylline-7-acetic acid | |

TABLE II-continued

| Reactants | Product |
|---|---|
| +<br>2,6-Dichlorbenzaldehyde<br>+<br>3,5-Diamino-1,2,4-triazole | 3-(2,6-Dichlorobenzylideneamino)-5-(theophylline-7-acetamido)-1,2,4-triazole |
| (200)<br>Trolox +<br>Betaine +<br>3,5-Diamino-1,2,4-triazole | 3-(6-Hydroxy-2,5,7,8-tetramethylchroman-2-carboxamido)-5-(N,N,N-trimethylmethanaminiumcarboxamido)-1,2,4-triazole |
| (201)<br>Theophylline-7-acetic acid +<br>3,5-Diamino-1,2,4-triazole +<br>Acetylsalicylic | 3-(-2-Acetoxybenzamido)-5-(theophylline-7-acetamido)-1,2,4-triazole |
| (202)<br>Theophylline-7-acetic acid +<br>2-Guanidinoacetoxybenzoic acid +<br>3,5-Diamino-1,2,4-triazole | 3-(-2-Guanidinoacetoxybenzamido)-5-(theophylline-7-acetamido)-1,2,4-triazole |
| (203)<br>8-Aminocaffeine +<br>2-Guanidinoacetoxy-benzoic acid | 3,7-Dihydro-8-(2-guanidinoacetoxyphenyl-carboxamido)-1,3,7-trimethyl-1H-purine-2,6-dione |
| (204)<br>P-Hydroxyanilin +<br>Guanidinoacetic Acid | N-(4-Guanidinoacetoxy)-guanidino-acetanilid |
| ((205)<br>8-Aminocaffeine +<br>Trolox | 3,7-Dihydro-8-(6-hydroxy-2,5,7,8-tetramethylchroman-2-carboxamido)-1,3,7-trimethyl-1H-purine-2,6-dione |
| (206)<br>Trolox + Cytosine +<br>Guanidineacetic Acid | 4-N-(-6-Guanidinoacetoxy-2,5,7,8-tetra-methylchroman-2-carboxamido)-4-2-(hydroxy)-pyrimidine |
| (207)<br>Trolox + 8-Aminocaffeine +<br>Guanidineacetic acid | 3,7-Dihydro-8-N-(-2-guanidinoacetoxy-2,5,7,8-tetramethylchroman-2-carboxamido)-1,3,7-trimethylxanthine |
| (208)<br>Thioctic acid<br>(Alpha-lipoic acid)<br>+<br>Aminoguanidine | N-(1,2-Dithiolane-3-pentanainido)-guanidine |
| (209)<br>Thioctic acid + 3,5-Diamino-1,2,4-triazole | 3,5-Bis-(1,2-dithiolane-3-pentanamido)-1,2,4-triazole |
| (210)<br>Aminoguanidine +<br>3,3'Thiodipropionic acid | 3,3'-Thiodipropanamidoguanidine |
| (211) | |

TABLE II-continued

| Reactants | Product |
|---|---|
| Maleic Acid + Aminoguanidine | Cis-1,2-ethylene-bis-(carboxamido)-guanidine |
| (212) Theophylline-7-acetic acid + 3,5-Diamino-1,2,4-triazole + Glycine | 3-(Glycylamido)-5-(theophylline-7-acetamido)-1,2,3-triazine |
| (213) 8-Aminocaffeine + 2-(4-Amino-3,5-dichlorophenyl)-2-hydroxyethylaldehyde | 8-[2-(4-Amino-3,5-dichlorophenyl)-2-hydroxyethylene]-8-imino-1,3,7-trimethylxanthine |
| (214) Cafaminol + Guanidineacetic acid | 8-[(2-Guanidinoacetoxyethyl methylamino)-caffeine |
| (215) 8-Aminocaffeine + GABA | 8-(4-Aminobutyramido)-1,3,7-trimethyl-xanthine |
| (216) 2'-Deoxyadenosine + Guanidineacetic acid | 9-(2'-Deoxy-5'-guanidinoacetoxy)-9-beta-D-ribofuranosidoadenine or 2'-deoxyadenosine-5-'guanidinoacetic acid ester |
| (217) N-(-4-)Chlorophenyl)-N'-(1-methyl-ethyl)imido-dicarbonimidic diamide (Available commercially as chlorguanide) | |
| (218) 4-Chlorobutyric Acid + Dimethoxybenzylidene-guanidine | 4-N-(2,6-Dimethoxybenzylideneamino)-4-amidinobutyric acid |
| (219) 4-Chloro-3,5-xylenol + 2-Hydrazinoimidazole | 2-(2,6-Dimethyl-4-hydroxyphenylamino)-2-aminoimidazole |
| (220) 8-Chlorocaffeine + 5-Hydroxytryptamine | 8-N-(5-Hydroxyindole-3-ethylamino)-8-(1,3,7-trimethyl)-xanthine |
| (221) 7-(2-Chloroethyl)-theophylline + Aminoguanidine | 7-(Guanidinoaminoethyl)-7-(1,3-dimethyl)-xanthine |
| (222) 8-Chlorocaffeine + 4-Aminobutyric Acid | 4-N-(8-Amino-1,3,7-trimethylxanthine)-4-butyric acid |
| (223) 4-Amidinobenzamide + Chlorodiphenylmethane | N-(Diphenylmethyl)-4-(amidino)- |

TABLE II-continued

| Reactants | Product |
|---|---|
| | Benzamide |
| (224) 8-Chlorotheophylline + Hydralazine | |
| | 1-N-(Theophylline-8-amino)-1-amino-pthalazine |
| (225) 2-Chloroadenosine + Guanidine | |
| | 6-Amino-2-guanidinopurineriboside |
| (226) 4-Chlorophenoxyacetic acid + Aminoguanidine | |
| | 4-Chlorophenoxyacetamidoguanidine |
| (227) 4-Chlorophenoxyacetamido-guanidine + Aminoguanidine | |
| | 4-Aminoguanidinophenoxyacetamido-guanidine |
| (228) 2-Amino-1,3,4-thiadiazole + 8-Chlorocaffeine | |
| | 2-(8-caffeineamino)-1,3,4-thiadiazole 2-N-(1,3,7-Trimethylxanthine-8-amino)-1,3,4-thiadiazole |
| (229) Cyheptamide + 8-Chlorocaffeine | |
| | 8-N-(10,11-Dihydro-5H-dibenzo[a,d]cycloheptene-5-carboxamido)-8-(1,3,7-trimethyl)-xanthine |
| (230) 4,6-Dichloro-2-(methylthio)-pyrimidine + aminoguanidine | |
| | 4,6-Diaminoguanidino-2-(methylthio)-pyrimidine |
| (231) 4-Chlorophenoxyacetamido-guanidine + cyheptamide | |
| | 5-N-(10,11-Dihydro-5H-dibenzo[a,d]cycloheptene-5-carboxamido)-5-(phenoxyacetamido)-guanidine |
| (232) 3,5-Diamino-1,2,4-triazole + 8-chlorocaffeine | |
| | 3,5-Bis-(7-methyl-8-theophyllineamino)-1,2,4-triazole |
| (233) Biotin + 4-Amidinobenzamide | |
| | N-(Hexahydro-2-oxo-1H-thieno[3,4-d]-imidazole-4-pentanoyl)-4-amidinobenzamide |
| (234) Biotin + Aminoguanidine | |
| | N-(Hexahydro-2-oxo-1H-thieno[3,4-d]-imidazole-4-pentanamido-4-guanidine |

The major sub-genuses of compounds listed herein, include compounds having an acyclic guanidino moiety, such as the first compound in Table I, and compounds wherein the guanidino moiety is part of an aromatic, cyclic group, such as the s-triazine group, as shown, for example, by the fourth compound in Table I, as well as compounds wherein the guanidino group is part of a non-aromatic, either saturated or unsaturated cyclic group, such as in Compounds 2 and 92–95.

The conditions which have been found to be effective in carrying out the preparation reactions exemplified by Table II, are substantially the same as those set forth in the co-pending application Ser. No. 689,712.

Preferably, these guanidino compounds of the present invention can be transformed from the free base into the form of their physiologically acceptable salts by customary methods, as described, for example, in U.S. Pat. No. 3,975,533. Useful such salts, include, for example, the salts of inorganic acids, such as hydrochloric, hydrobromic, hydriodic, sulfuric or phosphoric acids, as well as of organic acids including acetic, malic, ethionic, malonic, citric, benzoic, succinic, sulfamic, lactic, tartaric, cinnamic, gluconic, ascorbic, and pamoic acids. The compounds can also usefully form quaternary ammonium salts with a variety of organic esters of sulfuric, hydrohalic and aromatic sulfonic acids. Among such esters are methyl chloride and bromide, ethyl chloride, propyl chloride, butyl chloride, isobutyl chloride, benzyl chloride, and bromide, phenethyl bromide, naphthylmethyl chloride, dimethylsulfate, diethylsulfate, methylbenzene sulfonate, ethyltoluene sulfonate, ethylene chlorohydrin, propylene chlorohydrin, allyl bromide, methallyl bromide, and crotyl bromide.

Although it is preferred that compounds having anesthetic properties be administered parenterally, all of these compounds can be usefully administered orally, or by other means well known to the art.

Thus, the compounds of the present invention can be used as medicaments for mammals in the form of pharmaceutical preparations suitable for administration orally, parenterally, intraperitoneally, intravenously, by dermal patch, or as nasal spray, depending on their intended use and activity. These compounds can be administered in a substantially pure form, with other active ingredients which may be desirable, or dissolved or diluted in a suitable pharmaceutical vehicle. The compounds are generally crystalline solids or oils which can be at least partially soluble in commonly used organic solvents. They are also generally soluble in liquid pharmaceutical vehicles, including water, especially when they are formed as their physiologically acceptable salts. Generally, the acid addition salts are more soluble in water than are the free base compounds, per se. Formulation in a pharmaceutical vehicle can be carried out in accordance with techniques and in vehicles which are wholly conventional to those skilled in the art for the intended mode of administration.

Non-parenteral modes of administration can be preferable, especially where anaesthesia is not sought, for the compounds of this invention. For example, preparations for oral administration can be in either liquid or solid form, including for example syrups, elixirs, powders, capsules or tablets. The materials are preferably prepared for unit dosage form as powders which are preferably pressed into tablets or suitably encapsulated in, for example, conventional gelatine capsules. Any powders or compressed tablets can generally also comprise the usually suitable excipients and/or diluents, such as starch, lactose, stearic acid, magnesium stearate, dextrin or polyvinylpyrrolidone.

Other suitable solid carriers include magnesium stearate, sicaryl alcohol, talc, vegetable oils or fats, alcohols such as benzyl alcohols, gums, waxes, alkylene or polyalkylene glycols, such as propylene glycol or polypropylene glycol and any other well known carriers.

Suitable sterile solutions or suspensions can be prepared for parenteral or intraperitoneal administration, e.g., intravenous, containing for example water, dextrose, physiological saline, benzyl alcohol, ethyl oleate, methylcellulose, dimethyl sulfoxide, polyethylene glycol liquid, as well as other liquid excipients well known in the pharmaceutical or veterinary art. Other auxiliary pharmaceutical materials which can be present include preservatives, stabilizers, wetting or emulsifying agents, or osmotic salts or buffering agents, as is well known to the pharmaceutical or veterinary art. As these formulations are generally well known and conventional, more specific instructions need not be presented for purposes of defining this invention.

Typical, illustrative species of this class of pharmaceuticals are the following:

1-(2-Chloro-6-(trifluoromethyl)-benzylideneamino)-guanidine;

1-(2-Chloro-3,6-bis(trifluoromethyl)-benzylideneamino)-guanidine;

1-(2-Chloro-6-bromobenzylideneamino)-guanidine;

1-(2,6-Dibromobenzylideneamino)-guanidine;

1-(2-Bromo-6-methylbenzylideneamino)-guanidine;

1-(2,3,6-Tribromobenzylideneamino)-guanidine;

1-(2-Chloro-6-propylbenzylideneamino)-guanidine;

1-(2,4,6-Trichlorobenzylideneamino)-guanidine;

1-(2,6-Dichloro-4-methylbenzylideneamino)-guanidine;

1-(2-Bromo-6-fluorobenzylideneamino)-guanidine;

1-(2,6-Dichlorobenzylideneamino)-2-propynyl-guanidine;

1-(2,6-Dichlorobenzylideneamino)-1,2,3-trimethyl-guanidine;

1-(2,6-Dichlorobenzylideneamino)-,2,3-vinylene-guanidine;

1-(2,6-Dibromo-4-methylbenzylideneamino)-guanidine;

1-(2-Chloro-alpha-methylbenzylideneamino)-guanidine hydrochloride;

1-(2-(Trifluoromethyl)-alpha-methylbenzylideneamino)-guanidine hydrochloride;

1-(2-Chlorobenzylideneamino)-guanidine;

1-(2,4-Dichloro-alpha-methylbenzylideneamino)-guanidine,

Arcaine & Pentamidine, and the corresponding acid addition salts of the lower carboxylic acids, i.e., of fewer than six carbon atoms.

The pronounced hypothermia effect from the administration of these guanidino compounds can be a useful adjunct to the anesthetic effect, especially during lengthy or critical surgical procedures, such as during neurosurgery, cardiovascular surgery or organ transplant procedures. Specifically, the core temperature of a mammal can be allowed to drop by as much as about 15 degrees C., or even more, and be maintained at that low temperature without any danger to the organism. The lower temperatures decrease the possibility of and/or prevent from significant damage to major organs, e.g., the brain, during surgery, in the event of any serious malfunction or error. Further, it provides for a relatively bloodless surgical field of operation, and thus may obviate intentional stoppage of blood flow.

Although the core temperature drops significantly, the mammal is even less susceptible to injury from extreme variations of temperatures than an untreated mammal. For example, after administration of a guanidino compound, such as guanabenz, a mammal can be subjected to extremely low or elevated temperatures, e.g. as low as minus 20° C., or as high as 42° C., without injury. This resetting of the thermoregulator can provide protection for mammals during thermogenic or cryogenic surgical procedures.

Most useful from a clinical perspective, the guanidino compounds, as well as their antagonists, are easily titratable; and thus it is possible independently, and at almost any desired rate, to counteract the anesthetic or hypothermic effect of guanidino compounds by the use of a suitable antagonist. Specifically, for example, if it is desired to block or terminate the hypothermic effect, an alpha 2-adrenoceptor antagonist can be used, either prior to, together with, or after the administration of guanabenz, which will cause the core temperature to return towards and be maintained at, about normal levels, substantially without reducing the anesthetized condition of the mammal. Indeed, by, preferably, first administering a hypothermia antagonist, prior to administration of the guanidino compound, the anesthetic effect may be enhanced, and occurs more quickly. An example of such effect-specific alpha$_2$-antagonists, is tolazoline, and e.g., the compounds 98–101, 162, 163 in Tables I and II Contrariwise, if an anesthetic effect is not desired, but a hypothermic effect is desired, it is possible either to reduce or eliminate the anaesthetic effect of a guanidino compound having both activities, or to select a compound which does not have anesthetic properties, but does have hypothermic properties. If it is desirable to administer one of the guanidino compounds, without anesthetic effect, while maintaining the hypothermic effect, the guanidino compound can be combined with, e.g., a xanthine, such as aminophylline or isopropylmethyl xanthine, or a beta-agonist, such as isoproterenol or clenbuterol. Some antagonists will reverse both the hypothermic and anesthetic effects of guanidino compounds. Examples of such a selective alpha2-antagonist are Yohimbine, and compounds 96, 97 and 122 in Tables I and II. The effect can also be partially reversed, or reversed in stages, if desired, by administering several smaller aliquots of the antagonist. Interestingly, Naloxone, was not found to be a useful antagonist, indicating that the anesthesia is not induced through the opiate receptors.

Certain of the compounds produce a profound hypothermia, but without anesthetizing. In addition, it has been found that these guanidino compounds have other useful properties which complement or are in addition to the above two effects. Table III, following, sets forth a list of the other properties of these guanidino compounds, which arise from their alpha-adrenergic agonist activity, combined with any inherent activity of the reactants chosen to achieve the final compound.

TABLE III

The Activities and Properties of the Guanidino and Other Agonist or Antagonist Compounds of This Invention 1) Treatment and prevention of Neurological Damage, by disease or trauma, e.g., Retard progression of and/or ameliorate neurological degenerative disease such as:
   a) Amyotrophic lateral sclerosis
   b) Parkinson's Syndrome or Disease
   c) Alzheimer's Disease
   d) Cerebral Palsy
   e) Muscular Dystrophy
   f) Multiple Sclerosis
   g) Traumatic CNS injury (head trauma and spinal cord trauma Paraplegia and Hemiplegia);
   h) Cerebrovascular Accidents (CVS) Minimizes Reperfusion Injury and Thromboemblic Stroke;
   i) minimizes or inhibits the side-effects of opiate withdrawal
2) Antispasticity and muscle relaxant
3) Bronchodilator (treats Emphysema and asthma, controls exaggerated mucous secretions)
4) Tonic stimulation of motor neurons; Retards and/or stops the loss of muscle mass
5) Serotonergic agonist excites coordinated motor activity and immediate weight bearing rapidly in spinal cord injured mammals treated with adrenoceptor active drugs
6) Inhibits formation of tight three dimensional dense collagen (scar tissue) formation that occurs during injury induced hypoxia
7) Stimulate release of the growth hormone and other growth factors which contribute to regeneration and repair of nerve tissue.
8) Increases blood perfusion pressure; treatment of Traumatic Spinal, Septic and Cardiovascular Shock
9) Antiinflammatory (used in acute inflammation/Edema from Arthritis, Rheumatoid or osteo-arthritis)
10) Analgesic (Cluster headaches, migraine)
11) Antioxidants; also can be used alone or in conjunction with other drugs for treatment of carcinoma during radiation therapy or accidental exposure to radiation
12) Antifungal (may be used alone or in conjunction with other drugs for treatment of HIV infections and AIDS); Topically for dermatologically inflammatory conditions; as from eczema and psoriasis
13) Cause Retardation or atrophy of tumors
14) Treatment of Nephrosclerosis, systemic Lupus erythematosis; Scleroderma and allergic reactions
15) Treatment of Gastrointestinal stress-induced ulcers; anti-emetic; pro-kinetic (increase or retard G.I motility)
16) Nasal decongestant (vasoconstriction of the mucosal membrane)
17) Anti-hypertensive
18) Inhibition of excess adipose deposition (Enhancement of lean body mass)
19) Anti-hyperlipoproteinemic (treatment of Atherosclerosis, retards plaque formation on the arterial walls)
20) Anti-epileptic
21) Anti-coagulant (blood)
22) Anesthetic,
23) Antipyretic, Hypothermic
24) Calcium channel blocker
25) Anti-colon carcinoma
26) Androgenic antagonist
27) Estrogenic antagonist (breast cancer treatment)
28) Anabolic (with little or no virilization)
29) NMDA (glutamate) receptor antagonist Except for items numbered 22 and 24–28 in Table III, substantially all of the guanidino compounds of this invention, as a result of their structure-activity relationship, are potent with respect to all of the above activities. However, as would be expected, various compounds have different, higher levels of, activities and properties which are listed as "Specific Properties", with the Compounds numbered, in Table IV, below, according to the numbers in Tables I and II.

TABLE IV

| Example No. | Specific Properties |
| --- | --- |
| 1 | 10, 15 |
| 2 | 10, 15 |
| 3 | 10, 23 |
| 4 | 5, 22 |
| 5 | 5, 23 |
| 6 | 9, 15, 21, 23, 25 |
| 7 | 3, 15, 22, 23 |
| 8 | 15, 22, 23 |
| 9 | 3, 10, 12, 15, 23, 25 |
| 10 | 10, 12, 23, 25 |
| 11 | 23, 24 |

TABLE IV-continued

| Example No. | Specific Properties |
|---|---|
| 12 | 22, 23 |
| 13 | 22, 23 |
| 14 | 2, 21, 22, 23 |
| 15 | 2, 23 |
| 16 | 2, 22, 23 |
| 17 | 22, 23 |
| 18 | 2, 15, 22, 23 |
| 19 | 2, 15, 23, 24 |
| 20 | 2, 15, 22, 23 |
| 21 | 2, 15, 23 |
| 22 | 2, 15, 23, 24 |
| 23 | 3, 8, 12, 25 |
| 24 | 15, 22, 23 |
| 25 | 2, 15, 23 |
| 26 | 2, 10, 23 |
| 27 | 8, 17 |
| 28 | 5, 23 |
| 29 | 5, 22, 23 |
| 30 | 15, 23 |
| 31 | 2, 3, 15, cholinergic |
| 32 | 1, 15, cholinergic |
| 33 | 2, 12, 13 |
| 34 | 2, 12, 13 |
| 35 | 3, 12, 15 |
| 36 | 3, 15 |
| 37 | 5, 12 |
| 38 | 5 |
| 39 | 2, 3, 12, 15 |
| 40 | 10, 12, 15, 25 |
| 41 | 2, 4 |
| 42 | 10, 12, 15, 24 |
| 43 | 1, 9, 10, 11, 19, 23 |
| 44 | 1, 3, 23 |
| 45 | 1, 2, 8, 15 |
| 46 | 1, 2, 12, 22, 23 |
| 47 | 8, 23, 24 |
| 48 | 1, 2, 5, 23 |
| 49 | 1, 2, 8 |
| 50 | 2, 15, 22, 23 |
| 51 | 2, 15, 17 |
| 52 | 5, 23 |
| 53 | 3, 8, 14, 23 |
| 54 | 3, 8, 14, 23 |
| 55 | 1, 2, 23 |
| 56 | 1, 2, 14, 24 |
| 57 | 3, 8, 14 |
| 58 | 2, 12, 13, 14 |
| 59 | 2, 12, 13, 14 |
| 60 | 2, 12, 13, 14 |
| 61 | 2, 12, 13, 14 |
| 62 | 2, 12, 13, 14 |
| 63 | 2, 10–15, 19 |
| 64 | 2, 10–15, 19 |
| 65 | 5, 23 |
| 66 | 2, 22–24 |
| 67 | 2, 10, 14, 15 |
| 68 | 2, 3, 22, 23, 24 |
| 69 | 2, 3, 22, 23 |
| 70 | 2, 3, 8, 12, 23 |
| 71 | 2, 9, 10, 12, 25 |
| 72 | 3, 5, 23 |
| 73 | 2, 10 |
| 74 | 5 |
| 75 | 2, 3, 8, 16 |
| 76 | 2, 3, 22, 23 |
| 77 | 10, 12, 25 |
| 78 | 5 |
| 79 | 10, 12, 25 |
| 80 | 10, 12, 25 |
| 81 | 10, 12, 25 |
| 82 | 3, 10, 12, 25 |
| 83 | 3, 10, 12, 25 |
| 84 | 3, 10, 12, 25 |
| 85 | 2, 15, 22, 23 |
| 86 | 2, 19, 23 |
| 87 | 2, 10, 24 |
| 88 | 10, 12, 25 |
| 89 | 10, 12, 23, 25 |
| 90 | 8, 9, 10, 11, 13, 14, 19 |
| 91 | 9, 10, 12, 25 |
| 92 | 2, 13, 14, 22, 23 |
| 93 | 2, 3, 14, 23 |
| 94 | 2, 8 |
| 95 | 2, 10, 20 |
| 96 | 3, adrenergic antagonist, 12 |
| 97 | 3, 2, 2, antagonist, 12 |
| 98 | adrenergic antagonist |
| 99 | adrenergic antagonist |
| 100 | adrenergic antagonist |
| 101 | adrenergic antagonist |
| 102 | 3, 14, 16, 17 antagonist |
| 103 | 5 |
| 104 | 2 |
| 105 | 9, 11, 13, 14, 15, 19 |
| 106 | 2, 3 |
| 107 | 2, 17 |
| 108 | 2, 13, 22, 23 |
| 109 | 22, 23 |
| 110 | 8, 9, 10, 11, 13, 14, 19 |
| 111 | 10, 22, 23 |
| 112 | 5, 8 |
| 113 | 8, 9, 10, 16 |
| 114 | 8, 9, 10, 11, 13, 14, 19 |
| 115 | 2, 8, 23 |
| 116 | 8, 9, 10, 11, 13, 14, 19 |
| 117 | 8, 9, 10, 11, 13, 14, 19 |
| 118 | 5, 10, 11 |
| 119 | 9, 10, 11, 12, 13, 14, 19 |
| 120 | 2, 11, 12, 13, 14, 19 |
| 121 | 3, 11, 12, 15 |
| 122 | 3, adrenergic antagonist, 15, 7 |
| 123 | 2, 8, 9, 10, 11–15 |
| 124 | 2, 8, 9, 10, 11, 14 |
| 125 | 5, 8, 9, 10, 11, 14 |
| 126 | 5, 9, 10 |
| 127 | 27 |
| 128 | 27 |
| 129 | 26 |
| 130 | 9, 10, 12, 25 |
| 131 | 9, 10–15, 25 |
| 132 | 11, 26 |
| 133 | 8–15, 17 |
| 134 | 8, 11, 26 |
| 135 | 9–15 |
| 136 | 9–11, 14 |
| 137 | 2, 9, 10 |
| 138 | 2, 3, 8–14 |
| 139 | 2, 9–14, 23, 25 |
| 140 | 26 (ESP Topical to treat male pattern baldness) |
| 141 | 3, 8–16, 26 |
| 142 | 11, 25, 27 |
| 143 | 27 |
| 144 | 26, 28 |
| 145 | 3, 8–16, 25 |
| 146 | 19, 26, 28 |
| 147 | 27 |
| 148 | 27 |
| 149 | 19, 27 (possible injection into corpus cavernosum or insertion into uretha to bring about erection in impotent male) |
| 150 | 2, 9, 11 |
| 151 | 6–11 (anti-impotence) |
| 152 | 6–11        " |
| 153 | 6–11        " |
| 154 | 26 |
| 155 | 26, 28 |
| 156 | 27 (some agonist activity) |
| 157 | 27 (      "              ) |
| 158 | 27 |
| 159 | 3, 8, 10 |
| 160 | 2, 4, 6 |
| 161 | 10, 17 |

TABLE IV-continued

| Example No. | Specific Properties |
|---|---|
| 162 | 14, 17 adrenergic antagonist, 22, 23 |
| 163 | 14, 17, adrenergic antagonist, 22, 23 |
| 164 | 3, 15, anesthesia antagonist |
| 165 | 8, 17 |
| 166 | 8, 17, 19 |
| 167 | Adrenergic, cholinergic, 22, 23 |
| 168 | 8, 9, 12, 22, 23 |
| 169 | 5, 22, 23 |
| 170 | 8, 9, 12, Vasodilator |
| 171 | 10, 12, 22, 23 |
| 172 | 2, 8, 9, 10, 11, 19 |
| 173 | 8–11, 19, 21, 25 |
| 174 | 8–11–19 |
| 175 | 9, 10, 19, 22, 23 |
| 176 | 2, 9, 17, 22, 23 |
| 177 | 2, 13–15, 22, 23 |
| 178 | 2, 13, 22, 23 |
| 179 | 17, 19, 22, 23 |
| 180 | 8–10, 13, 14, 22, 23 |
| 182 | 3, 7–15 |
| 183 | 8–16, 19 |
| 184 | 27, Progestin, androgenic |
| 185 | 27, " |
| 186 | 1927, Progestin, androgenic |
| 187 | 27, Progestin |
| 188 | 5, 9, 10, 13 |
| 189 | 2, 4, 6, 10 |
| 190 | 1, 2, 4, 6–11, 15–19, 29 |
| 191 | 1–4, 6–13, 16–19 |
| 192 | 1, 2, 8–10, 15, 29 Adrenergic antagonist |
| 193 | 1, 2, 8–10, 13, 17, 22, 29 |
| 194 | 1, 2, 4, 5, 8–10, 17 |
| 195 | 1, 2–5, 7–11, 17, 21 |
| 196 | 1, 4–5, 8 |
| 197 | 1–4, 6–13, 19, 21, 23, 25 |
| 198 | 1–4, 6–12, 14, 15, 22, 29 |
| 199 | 1, 4, 6–13, 19, 21, 25 |
| 200 | 1, 2–4, 8–11, 14, 17, 21 |
| 201 | 1–5, 8–14, 19, 20, 23, 25 |
| 202 | 1–14, 18–20, 23, 25 |
| 203 | 1–14, 16, 18–20, 23, 25, 29 |
| 204 | 1, 2, 6–10, 13–15, 17, 23 |
| 205 | 1, 2–5, 7–11, 14–17, 21, 22 |
| 206 | 1, 2, 8–10, 13, 17, 22, 23, 29 |
| 207 | 1, 2–10, 13, 17, 22, 23, 29 |
| 208 | 1, 4, 6–11, 14, 21, 22 |
| 209 | 1, 4, 8–14, 17, 22 |
| 210 | 1, 2, 6–10, 15, 17, 29 |
| 211 | 1, 2, 6, 11, 15, 17, 29 |
| 212 | 1, 2, 8–11, 13, 17–19, 23 |
| 213 | 1–6, 8–12, 16–20 |
| 214 | 1–12, 15, 16, 19, 29 |
| 215 | 1–6, 8–12, 15–20 |
| 216 | 1–4, 6–12, 14, 15, 22, 29 |
| 217 | 1, 4, 6–9, 16, 17, 19 antimalarial |
| 218 | 1, 4, 6–10, 16, 17, 23, 29 |
| 219 | 1, 4, 6–10, 15, 16, 17, 22, 23, 29 |
| 220 | 1–10, 17, 23, 26 |
| 221 | 1–4, 6–10, 14, 16–19, 23, 29 |
| 222 | 1–4, 6–10, 4, 16–19, 23, 29 |
| 223 | 1, 2, 4, 6, 9, 10, 14, 15, 17, 23, 29 Adrenergic antagonist |
| 224 | 1–4, 6–15, 17, 19, 23 |
| 225 | 1, 2, 4, 6–9, 13–15, 17, 29 |
| 226 | 1, 2, 4, 6–10, 17, 22, 23, 29 |
| 227 | 1, 2, 4, 6–10, 17, 23, 29 |
| 228 | 1, 2, 4, 6–19, 23, 29 |
| 229 | 1–10, 16–17, 23 |
| 230 | 1, 2, 4, 6–12, 15, 17, 22, 23, 29 |
| 231 | 1, 2, 4–10, 16–17, 22, 23, 29 |
| 232 | 1, 2, 4, 6–19, 22, 23, 29 |
| 233 | 1, 2, 4, 6, 9, 10, 14, 15, 17, 23, 29 Antialopecia, adrenergic antagonist |
| 234 | 1, 2, 4, 6–10, 14, 15, 17, 23, 29 |

Behavioral Responses

Following administration of the anesthesia-antagonist, or after the guanidino compound has been metabolized, i.e., about three-to-eight hours after administration (depending upon the dose), the treated mammal awakens, giving the appearance of being well rested and alert, without the "hang-over" and other debilitating effects associated with the administration of commonly used general anaesthetics. Although, guanabenz is well known for its hypotensive effect, it has relatively moderate hypotensive effect in the supine position, and therefore, during surgery. This property is shared by other guanidino compounds.

To induce anesthesia, the active anesthetic agent, e.g., guanabenz, is preferably administered intravenously with an initial unit dosage of at least about 4 mg and preferably, to a large mammal, from about 8 mg to about 25 mg, but optimally not more than about 15 mg. It is preferable to titrate drugs slowly to achieve the desired level of anesthesia and to avoid overdosage, and possible hypertensive spike, which results from administration as a bolus; the guanidino compound is preferably initially administered over a period of about two to about five minutes.

Oral administration, specifically to achieve hypothermia or the other effects listed in Table III, above, requires from about 20 mg. to about 50 mg. of a guanidino compound. For example, in laboratory rats it has been found that the I.P. administration of 12 mg guanabenz per kilogram of body weight is a sufficient amount to initially place the rats in an anesthetized condition; when dealing with a 60 to 75 kg mammal it has been found that the total amount administered in the initial single dose, e.g., by intravenous injection, need not be greater than about 0.5 mg/kg, and preferably in the range of from about 0.05 to about 0.3 mg/kg, to provide the desired anesthetic and hypothermic effect.

The anesthetic-effective guanidino compounds, e.g., the acetate addition salt of guanabenz, are most preferably administered intravenously, in 5 to 10 ml of a 5% dextrose solution, containing between approximately 1 and about 2 mg/ml of guanabenz, or an appropriate amount of another guanidino compound, to induce anesthesia. The guanidino compounds can also be administered in other suitable liquid carriers well known to those skilled in the art, such as physiologic saline solution, benzyl alcohol, ethyloleate, methylcellulose, or polyethylene glycol. After the subject mammal is initially placed under anesthesia, the anesthetic state can be maintained by, e.g., a continuing intravenous drip using the 5% aqueous dextrose solution. To induce anesthesia the guanidino compound in solution is preferably administered discontinuously in an amount of from about 1.0 to about 2.0 mg per minute, over a period of from about 2 to about 5 minutes. It can then be titrated discontinuously, via an intravenous drip, in 50 to 100 ml 5% dextrose solution, containing 0.1 to 0.2 mg/ml of the guanidino compound for a period of up to 24 hours, or even longer if necessary, to maintain the state of anesthesia/hibernation. Rats have been maintained for up to 12 days in a pseudo-hibernating condition. This condition can increase the success rate for surgery, and provide an extremely effective recuperative condition after a surgical procedure for traumatic injury.

To provide purely hypothermic activity, it is usually advisable to administer drugs orally, unless it is not feasible to do so, for example when the mammal is unconscious.

As is shown in Table II, above, most of the novel compounds of the present invention in accordance with Formulae I, II, or III, above, can be prepared by reacting at least two compounds; the first compound ("A") includes a guanidino group, which can be present, for example, as part of a heterocyclic group, e.g., an amino-triazine group, an amino-arylimidazole, e.g., 2-aminobenzimidazole, or 2-aminoimidazoline group, (or an equivalent thio- or oxo-2 compound where one of the nitrogen atoms forming any of the above groups is replaced by a sulphur atom or oxygen atom, respectively); the second compound ("B") comprises a lipophilic moiety, and a co-reactive substituent selected, for example, from the group of beta-hydroxyphenylacetic acid, aldehyde or amine, coreactive with a moiety on Compound "A". More generally, one of the above A and B compounds preferably include a free and reactive carbonyl group, (such as a carboxyl group, and aldehyde group), or a hydroxyl group or amino (—NH2) group, or other groups. The other of the above A and B compounds includes another group or groups, which are mutually reactive with the substituent on the first compound. Most preferably, the "A" compound reacts with the B compound through one of the primary or secondary amino nitrogen atoms forming part of the guanidino or aminoguanidino moiety.

Suitable group "A" reactant compounds include guanidine, aminoguanidine, guanidineacetic acid, 2-guanidinobenzimidazole, 2-aminoimidazole, 2-aminodihydrothiazine, 2-hydrazinoimidazoline, 3,5-Diamino-1,2,4-triazine, 2,4,6-triamino-1,3,5-s-triazine, 2,4-diamino-6-phenyl-1,3,5-s-triazine, 2,4-bis(diethylamino)-6-hydrazino-1,3,5-s-triazine, 4-methyl-4H-1,2,4-triazole-3-thiole, 4,5,diphenyl-2-imidazole-thiole, 2-(4-aminophenyl-6-methyl)-2-benzothiazole, 2-aminopurines, 2-aminopyrimidines, 2-aminocytidine, other acyclic or cyclic groups containing the guanidino moiety as defined by formula I, above, and their acid addition salts.

The following examples provide common procedures for preparing species which are preferred for their activity within the group of novel compounds constituting the invention. These procedures are similar to methods commonly used in the preparation of organic chemicals, and as previously described in my copending application Ser. no. 189,464, and its continuation, serial No.689,712. These illustrative compounds within the present invention may, of course, also be prepared by other paths.

EXAMPLE 1

Preparation of Bis-(4-methylbenzylidene)-Guanidine

4-Methylbenzaldehyde (MBA) (0.50 mols-60 grams) is admixed with guanidine hydrochloride (0.25 mols, 25 grams) in molar ratio of 2:1. They are then heated under reflux in 150 ml of toluene under a Dean Stark water collector trap for approximately 17 hours to collect the theoretical amount of $H_2O$ evolved. The hot solution is rapidly decanted to ensure the removal of insoluble residues. The solution is then evaporated to dryness on a rotary evaporator. The crude immine is then recrystalized twice from absolute ethanol.

The resultant product is shown as Number 3 in Tables I and II.

EXAMPLE 2

Preparation 2,4-Bis-(2,6-dichlorobenzylideneamino)-6-(5-hydroxyindole-3-ethylamino)-13,5-s-triazine (Compound. 4)

This asymmetrical compound, i.e., which has more than one substituent on the amino groups of melamine, is prepared by the following procedure:

In a 5L. 3-neck flask, are combined 63 g. (0.50M) of melamine and 200 ml of Bis-(2-methoxyethyl)-ether. This is heated to 85° C. under nitrogen, with a Herschberg stirrer. Through a pressure-equalizing separatory funnel, there is added dropwise, over a 4-hr. period, a mixture of 132.5 g of 5-benzyloxy-indole-3-acetaldehyde and 174 g of 2,6-dichlorobenzaldehyde, in 750 ml of warm Bis-(2-methoxyethyl) ether. During this period the temperature is slowly elevated to 120° C., and the elevated temperature is maintained for an additional 8-hr. period. At the end of this period, the solvent is removed under high vacuum on a rotary evaporator.

The resultant oil is chromatographed on Florisil, using a mixture of ethylacetate/benzene/pyridine (8:2:0.01), to obtain the product (Compound 4) in a yield of 34%. Electrospray-mass spectrometry indicated a single peak of m/e (613). The product is homogeneous on the following three thin-layer chromatographic systems ethylacetate: benzene:pyridine (8:2:0.01); butylacetate:butanol:ether: pyridine (8:3:1:0.01); methylacetate:hexane:pyridine (10:2:0.01).

EXAMPLE 3

The Preparation of 2-(Phenylacetyl)-2-hydrazinoimidazole (Compound 15)

Phenylacetic acid (PAA), 0.037 moles (5g) was heated under reflux with an excess of $SOCl_2$ for 60 minutes at a temperature of 75–80° C. After the reaction was completed, the excess $SOCl_2$ was eliminated by vacuum evaporation, using a water pump (40–50° C.). This process was repeated two to three times, each time adding benzene to aid in elimination of SOCl2 and yielding phenylacetyl chloride (PAC). Then, 0.018 mole of 2-hydrazino-2-imidazoline.HBr (3.5 g) was suspended in ether and shaken with 2N NaOH (2–5 equivalents) on an ice bath, until it was completely dissolved. The PAC was then added dropwise very slowly from a funnel with vigorous shaking. Excess NaOH was present to drive the reaction to completion. After the addition of PAC, the mixture was stirred at 0C for an additional 15–30 minutes. The ether layer was washed with water, then with saturated $NaHCO_3$. It was then dried over $Na_2SO_4$, filtered and was brought to complete dryness. The solid residue from the ether layer was then crystallized from an ethanol-water mixture (70–80% ethanol). The yield, was approximately 55% without subjecting the residual amide to further separation from the aqueous layer.

EXAMPLE 4

The Preparation of 2-(Indole-3-aminomethyl)-2-amidinobenimidazol (Compound 188)

A mixture of 0.035 moles of Indole-3-carboxaldehyde (ICA) (5 g) and 2-Guanidino-benzimidazole (GBI) (6 g) in 100–150 ml. of toluene was heated under reflux in a water collector, Dean Stark trap, for as long a period as required to collect the theoretical amount of water (12 hours) as follows: the reaction was first stopped after 2 hours and was then left to stand overnight at room temperature (25° C.). The next day the refluxing was resumed and carried out for 10 hours in order to collect the additional water evolving from the reaction of the aldehyde with the amine. After approximately 12 hours, the hot solution was rapidly decanted in order to remove any insoluble residue. It was then evaporated to dryness on the steam bath to a crude immine, that was later crystallized from absolute ethanol.

EXAMPLE 5

The Preparation of 2-(Indole-3-Methylene)-2-hydrazinoimidazole (Compound 52)

A mixture of 0.035 moles each of Indole-3-carboxaldehyde (ICA) (5 g) and 2-Hydrazine-2-imidazoline.Hbr (HIM) (6.34g) in 100–150 ml of toluene was heated under reflux under a water collector trap (Dean Stark) for as long a period as required to collect the theoretical amount of water (12 hours) as follows: the reaction was first stopped after 2 hours and left to stand overnight at room temperature (25° C.). The refluxing was resumed the next day and carried out for 10 hours in order to collect the additional water evolving from the reaction of the aldehyde with the amine. After approximately 12 hours, the still hot solution was rapidly decanted in order to remove any insoluble residue. It was then evaporated to dryness on the steam bath to a crude immine, which was later crystallized from absolute ethanol.

EXAMPLE 6

The Preparation of Phenylacetamidoamidine (Compound No.189)

Specifics

Phenylacetic acid (PAA) 0.037 mols 5 g) was added to excess $SOCl_2$ and heated under reflux for 60 minutes at the temperature of 75–8° C. After the reaction was completed, the excess $SOCl_2$ was eliminated under vacuum evaporation using a water pump (40–50° C.). This process was repeated 2 or 3 times, each time adding benzene to aid in SOCl2 elimination. Since phenylacetylchloride PAC is not volatile (b.p. about 160° C.), $SOCl_2$ evaporates and PAC remains in the flask. Guanidine (0.018 mole 1.72 g) was shaken with 2N NaOH (2–5 eq.) on an ice bath until it was completely dissolved. Excess NaOH was added either to neutralize HCl evolving from the reaction of acyl chloride (PAC) with guanidine or to act as a catalyst in the reaction. PAC was then added very slowly, dropwise, from a funnel with vigorous shaking. After the addition of PAc, the mixture was stirred at 0° C. for 15–30 minutes. The resulting pale yellow colored solid was filtered with Whatman #1 filter paper, the pH of the suspension was determined and adjusted to between 8–8.5, by the addition of dilute HCl, before filtering with the filter paper (W#1). The yellow solid was recrystallized twice with ethanolic mixture (80% EtOH/H2O).

EXAMPLE 7

Preparation of 2,4,6-Tris(2,6-dichlorobenzylideneamino)-1,3,5-s-Triazine (Compound No. 18)

A 3:1 ratio mixture of 2.6 dichlorobenzaldehyde and melamine was stirred together with a stoichiometric amount of toluene-sulfonic acid as a catalyst, in 150 ml of diglyme as a solvent. The mixture was stirred manually and then heated under reflux for 17 hours in a Dean Stark water trap, until the theoretical amount of water was collected. A hot filtration of the insoluble residue was performed. The hot yellow colored filtrate was cooled and then evaporated at 100° with a rotary evaporator under high (2 microns) vacuum. The precipitate was then recrystallized twice with a mixed solvent (absolute ethanol and hexane).

Additional Preparations

Following the same procedures as in Examples 1 and 2, additional compounds can be prepared by reacting the reagents as shown in Table I to form the compounds as presented in Table II.

The pharmacologic procedures of the present invention and compositions for use in such procedures are illustrated by the following examples. These are intended merely to exemplify the invention and to clarify the method of operation, without being exclusive of the full scope of this invention.

EXAMPLES 8–12

A group of four laboratory rats each weighing approximately 310–350 grams were treated by injecting 4 mg guanabenz intraperitoneally, in the form of the acetate salt dissolved in 1 ml of a sterile 5% dextrose aqueous solution. A fifth rat was treated with merely an equal amount of the dextrose solution without guanabenz acetate. The rats were subjected to an electrical tail stimulation, by electrodes attached to their tails, to determine the point of positive (threshold) vocalization.

The normal vocalization threshold, and the point at which the control rat vocalized was approximately 7 volts. Beginning seven minutes after injection of the guanabenz solution, the four test rats all failed to vocalize after a shock of 10 volts; thereafter, as shown, the animal became profoundly anesthetized and no vocalization response was obtained even when stimulated at 40 Volts. To bring the rats out of anesthesia, the rats were then injected with 40 mgs. of aminophylline, also in 1 ml of a 5% aqueous dextrose solution. The rat's pain threshold was again tested; as shown, vocalization that was absent during guanabenz anesthesia, returned within 6 minutes after injection of the aminophylline at 12 volts, and then was present at the normal threshold of 7 volts, by 8 minutes after the injection of aminophylline. The normal threshold for vocalization was reestablished, as there was no vocalization at 6 volts following recovery from anesthesia.

The rats were maintained under anaesthesia for a period of 50 minutes before injection of the aminophylline.

EXAMPLES 13–36

The core temperatures of another twenty test rats were measured: eight rats were injected with guanabenz exactly as in Examples 8–12; another eight were injected with the same quantity of Compound No. 13 (Melazine) in Tables I and II, also in 5% dextrose solution; and eight rats were used as a control and injected only with the vehicle, i.e., 5% dextrose solution. The core temperatures (colonic measurement) of the eight guanabenz-treated test rats dropped from an average normal value of 36.5° C. to 22.5° C., and the eight Melazine-treated rats to 21.5° C., within 25 to 45 minutes, and stabilized at that level. Room temperature was 21.5° C. The mean intraperitoneal temperatures of guanabenz- and Melazine-treated rats dropped to 31.5° C. and 30.2° C., respectively, as did the temperature of their abdominal cavity. The temperatures of the liver and the kidneys each dropped to about 33.5° C. for the guanabenz-treated rats and 32.7° C. for the Melazine-treated rats. The control rats, injected only with the carrier dextrose solution, maintained a relatively constant temperature during the entire test period under identical conditions of the test. The guanabenz-treated rats were anesthetized, but the Melazine-treated rats remained awake. An injection of aminophylline to three of the rats treated with guanabenz caused them to awaken, but had practically no effect on body temperature; injection of the aminophylline to three of the melazine-treated rats had no discernible effect.

Six of the anesthesized rats were also injected with aminophylline, they then received an injection of tolazoline (an alpha adrenergic antagonist); within 25 minutes the anesthesia-hypothermia induced by guanabenz was completely reversed and the body temperatures of the rats had returned to normal.

The fourth pair of guanabenz-treated rats were injected I.P. with 10 mg Yohimbine in a 5% aqueous dextrose solution. These rats were brought out of anesthesia by yohimbine and their hypothermia was simultaneously reversed, rendering the rats awake, with their body temperature returning to normal.

EXAMPLES 37–43

Four additional rats were treated with the guanabenz solution as in Examples 8–12, administered intraperitonally. The core temperatures were again monitored; they dropped to 21° C. (room temperature). Approximately 30 minutes after receiving the guanabenz injection, the rats were placed in a temperature controlled room maintained at minus (−) 30° C. (plus or minus 0.5° C.).

The core temperatures of the four treated rats, as well as that of two control rats who received only the dextrose solution, were continuously monitored. It was found that approximately 15 minutes after placement within the cold room, the average core temperature of the two control rats dropped to minus (−) 20° C. At the same time, the core temperatures of the four rats treated with guanabenz was at approximately plus (+) 16° C. Thus, as a further beneficial effect, guanabenz does not produce the usual poikilothermic condition, and, once a reduced temperature is set, in fact, it protects against any dangerous further temperature drops or excessive increases, by resetting, the mammals' thermoregulator (thermostat), and thus protecting against extremes of temperature fluctuations.

EXAMPLES 44–47

A further two rats received, intraperitonally, the same quantity of guanabenz acetate as in Examples 8–12, at an ambient temperature of 21° C. The core temperatures of the rats were allowed to fall to approximately 30° C., after about 15 minutes. At that time, the rats were placed in a temperature controlled room maintained at 42° C., together with 2 control rats treated only with the dextrose solution. Within three minutes, the control rats expressed extreme agitation and vocalization, and attempted to escape from what appeared to be an uncomfortably hot temperature. The treated rats remained under anesthesia and the core temperatures in each case remained unchanged at 30° C.

EXAMPLES 48–59

In the following three sets of experiments, laboratory rats each weighing 300–350 gms., were injected with guanabenz acetate alone or with other compounds, to test their effect on core temperature, analgesia, and anesthesia, as determined by evoking several reflexes.

Nos. 28–53: At a room temperature of 21° C., three pairs of rats were injected (I.P.) with guanabenz acetate (G, 12 mg/kg) or diazepam (D, 6 mg/kg) or a combination (G+D). Twenty minutes after injection, the core temperature of the G-treated and (G+D)-treated rats was reduced to about 31° C. There was no change in the core temperature of the D-treated rats. The patellar, urethro-anal (bulbocavernosis), startle, and corneal reflexes were absent after 30 minutes in G-treated animals, indicating profound anesthesia, but all such reflexes were present in the D-treated animals. In the rats treated with the combination of drugs G, and D, the urethro-anal and vestibular reflexes were absent; other reflexes, i.e., withdrawal, tail compression, corneal, and righting were present, indicating no anesthesia (probably resulting from the inhibition of c-AMP phosphodiesterase enzyme by the Diazepam, which is similar to the effect of the xanthines), and thus counteracts the state of anesthesia.

Nos. 54–61: At a room temperature of 19.4° C., each of four pairs of rats were injected I.P. with either guanabenz acetate (12 mg/kg), or guanabenz acetate (12 mg/kg) plus pentabarbital (25 mg/kg), or pentabarbital alone (25 mg/kg), or ketamine (80 mg/kg), respectively. The mean core temperature of the pairs of rats dropped to 24.3° C., 32.1° C., 29.3° C., and 34.5° C., respectively, one hour after injection. All of the reflexes tested in Examples 48–53 had disappeared in all of the animals. Animals receiving guanabenz acetate showed mydriasis, profound exophthalmia and micturition. In the anesthetized animals treated with guanabenz acetate, the ears, the forelimb digits and the hindlimb digits, were pink as compared with the semi-cyanotic appearance of the ears and digits of the animals treated with pentabarbital and ketamine that did not survive the given doses of the drugs.

EXAMPLE 62

A 70 kg mammal is administered 6 mg guanabenz dissolved in 1 ml of sterile 5% dextrose aqueous solution, administered by intravenous injection over a period of three minutes. After exhibiting deep sedation, within five minutes after injection, the mammal falls into profound anesthesia. The large mammal does not overtly react to the noxious stimulation of pin-pricks at its upper extremity (digits), and does not exhibit the corneal reflex.

An intravenous drip of 5% aqueous dextrose solution containing 0.1 mg guanabenz/ml is administered beginning about 120 minutes after the initial injection, at a constant rate of 1 ml/min, over an additional period of 30 minutes. The large mammal continues under profound anesthesia for an additional about two hours. Thereafter, an intravenous injection containing 20 mg of aminophylline is administered over a period of five minutes. The large mammal is fully awakened within about 20 minutes, appearing alert and refreshed.

The period of time required to fully reverse the anesthesia can be increased or decreased by proportionally changing the amount of the antagonist. After metabolism of guanabenz, the mammal will spontaneously awaken, within about three to six hours after the I.V. drip is discontinued.

EXAMPLES 63–66

Examples 8–12 are repeated except that an equal dosage bolus (4 mg) of tolazoline in dextrose solution is intravenously administered approximately twenty minutes before commencing the first bolus injection of the guanabenz acetate.

The four Sprague-Dawley rats become anesthetized within five minutes, and remain under anesthesia for as long as four hours without further administration of the guanabenz.

EXAMPLES 67–70

Two rats received, intraperitonally, the same quantity as in Examples 8–12 of Compound No. 18, the acetate salt of 2,4-6-Tris-(2,6-dichlorobenzylideneamino)-1,3,5-s-triazine, at an ambient temperature of 21° C. The core temperatures of the rats were allowed to fall to approximately 30° C. At that time, the rats were placed in a temperature controlled room maintained at 42° C., together with two control rats treated only with the dextrose solution. Within two minutes, the control rats expressed extreme agitation and vocalization, and attempted to escape from what appeared to be an uncomfortably hot temperature. The treated rats remained calm, but active, and the core temperatures of each treated rat remained unchanged at 30° C.

EXAMPLES 71–86

Efficacy of the treatment with compounds of this invention very low ambient temperatures is demonstrated by the following examples:

Sprague-Dawley rats (8) were injected, IP, with 12 mg/kg each of guanabenz in 5% aqueous dextrose solution and eight other rats were injected with the carrier solution only. All sixteen rats were placed in a temperature-controlled room maintained at 4–5° C. immediately after injection. The brain temperatures of all 16 rats were recorded after 45 minutes: the control rats maintained a substantially constant average brain temperature of approximately 36.7° C., the brain temperature of the guanabenz-treated rats dropped from the original mean of 37° C. to a mean of 27° C. The colonic, or core, temperature of the eight guanabenz-treated rats was measured after 15, 20, 28, 37, 40 and 45 minutes. The temperature was found to have dropped to approximately 24° C. after 15 minutes, to 22° C. after 22 minutes, to 20° C. after 30 minutes, and down to 17° C. after 45 minutes. The core temperature had its major drop during the initial 15 to 20 minutes time period. Ultimately, the core temperature reached a value of 10° C. lower than the brain temperature. Mammals treated with the guanidino compounds possessing hypothermic properties are protected from extreme temperature fluctuations. They resume normal behavior after this experiment, i.e., drinking, eating and grooming, etc.

It is of interest to note that some of the same neuroprotective compounds which provide relief from the effects of severe trauma or other injuries to the central nervous system, can also serve as effective anesthetic agents during surgical procedures. For example, for an accident victim that has suffered severe spinal injury, the same compound, e.g., guanabenz, can provide anesthesia as well as neuroprotection. It is thus possible, under,e.g., guanabenz anesthesia, to provide the surgical treatment necessary to correct any mechanical effects of the accident, i.e., removing any bone compression or bone fragments, while simultaneously starting the medical treatment of the individual, using the same anesthetic compound.

Chronically injured mammals can also be successfully treated utilizing the compounds and procedures of this invention. The following comprise a useful method for functional restoration:

All animal species admitted with traumatic spinal cord injury will receive high quality nursing care. The paralyzed animals will be examined by x-ray, cat scan or MRI. It is preferable to use both of the latter procedures to localize the area of the injury and determine if the compromised spinal cord is in need of decompression. All necessary neurosurgical procedures should be performed to correct and remove any adhesions or compression of the spinal cord. For any such operation, guanabenz (12 mg/kg) should be used as an anesthesia.

During the laminectomy surgery, after the dura has been exposed, if scar tissue has formed, the area of the scar at the lesion site can be frozen by liquid nitrogen using an instrument (formed of a steel bowl attached to a tube 18 cm long, 0.8 cm diameter, with a concave surface at the end and containing a hole 1 mm in diameter, in the middle, through which liquid nitrogen drips onto the scar). After 5 minutes of freezing the scar tissue, the animals are then resutured. Alternatively, collagenase alone or with streptokinase, can be applied to the scar tissue. It is also useful to apply both liquid nitrogen and collagenase.

If the neuroradiological methods demonstrate no compression of the spinal cord, laminectomy is unnecessary. However, the scar tissue should still be softened. The area of the scar can be localized fluoroscopically, and preferably collegenase (and possibly streptokinase) is directed to the area of the lesion obviating the need for performing the laminectomy.

The animals are treated with a guanidino compound, e.g., guanphylline or aminoguanphylline, twice daily (1 mg/kg). Approximately 10, 14 and 20 days after treatment with, e.g., guanphylline or aminoguanphylline is commenced, these animals can also be treated with a serotonergic ("5-HT") receptor agonist; such as quipazine (1–2 mg/kg). Such serotonergic compounds can accelerate the recovery period, i.e., shorten the period after which time the animals become mobile. The animals should then continue to be treated systemically with the guanidino compound twice daily for six to eight weeks, or until functional recovery has been achieved.

Many rats and cats have been treated with several alphaadrenoceptor agonists in order to ascertain which drug has the least side effects and reduces the time period for recovery. Aminoguanphylline, guanphylline, 7-(guanidinoacetyl)-theophylline have been found efficacious.

The purpose of liquid nitrogen is to reduce the structural integrity of the collagen laden, glial scar tissue, by freezing and defrosting. Collagenase then initiates a debridgement of the scar without attacking the nervous and osseous tissue. If required, streptokinase, or alteplase, both plasminogen activators can also be used to bring about a complete debridgement. In addition to 3-amino-propionitrile (a latherogen), 5-fluorodeoxyuridine and dehydroproline can be used to arrest further glial and fibroblastic invasion of the scar region, respectively. Aminoguanidine, aminoguanphylline, clonidine, guanabenz, and guanphylline also interfere with formation of the scar.

Maintaining treatment for several months is needed for primates.

We have found that subjecting the animals to other physiological manipulations and exercise is effective in the recovery process, e.g., the use of treadmill, retrograde (sciatic nerve) stimulation, and functional electrical stimulation.

The patentable embodiments of this invention which are claimed are as follows:

1. A method for treating a mammal having a damaged central nervous system, as the result of trauma or disease, for reestablishing previously destroyed neurological functions in a traumatized or diseased mammal, or for controlling spasticity, and for providing protection from such injury to the central nervous system, the method comprising administering to the mammal at least one pharmacologically active compound as the primary therapeutic agent, the pharmacologically active compound comprising two neurologically active groups, one neurologically active group comprising a first guanidino-containing moiety, and the second neurologically active group comprising an alkylated xanthine group and providing beta-agonist activity, the pharmacologically active compound thus providing a combination of neurological receptor activity designed to stimulate the appropriate alpha-adrenergic and beta-adrenergic receptors in the central nervous system and thus tonically stimulate motor neurons, in a mammal having a damaged central nervous system, the pharmacologically active compound being administered in a dosage amount and at a dosage rate sufficient to at least partially restore the lost neurological function or to control spasticity, the guanidino-containing moiety being connected to the xanthine group through an aliphatic bridging group substituted on a xanthine ring nitrogen atom and to one of the guanidino nitrogen atoms.

2. A method for treating a mammal having a damaged central nervous system, as the result of trauma or disease, for reestablishing previously destroyed neurological functions in a traumatized or diseased mammal, or for controlling spasticity, and for providing protection from such injury to the central nervous system, the method comprising administering to the mammal at least one pharmacologically active compound as the primary therapeutic agent, the pharmacologically active compound comprising two neurologically active groups, one neurologically active group comprising a guanidino-containing moiety, and the second neurologically active group comprising an alkylated xanthine group and providing beta-agonist activity, the pharmacologically active compound thus providing a combination of neurological receptor activity designed to stimulate the appropriate alpha-adrenergic and beta-adrenergic receptors in the central nervous system and thus tonically stimulate motor neurons, in a mammal having a damaged central nervous system, the pharmacologically active compound being administered in a dosage amount and at a dosage rate sufficient to at least partially restore the lost neurological function or to control spasticity, wherein the first neurologically active group is selected from the group consisting of a guanidino, aminoguanidino, 2-imidazolino, 2-hydrazinoimidazolino and 2-guanidinobenzimidazolino groups.

3. The method of claim 1, in the pharmacologically active compounds, the aliphatic bridging group includes a carboxyl group, a carbonyl group, or an oxygen, nitrogen, or sulfur atom, and the bridging group is connected to a nitrogen atom of the guanidino group by a double bond.

4. The method of claim 1, in the pharmacologically active compounds the guanidino moiety is connected to an aliphatic carbon atom of the bridging group and the bridging group is connected to the 1-position or the 7-position nitrogen atom of the xanthine group through an aliphatic carbon atom on the bridging group, but excluding compounds where a guanidino group is attached to the 7-nitrogen atom of the xanthine group through an aliphatic hydrocarbyl group.

5. The method of claim 1, wherein the pharmacologically-active compound is selected from the group consisting of guanidino-7-acetyltheophylline, aminoguanidino-7-acetyltheophylline, and theobromine-1-acetylguanidine.

6. A method for treating a mammal having a damaged central nervous system, as the result of trauma or disease, for reestablishing previously destroyed neurological functions in a traumatized or diseased mammal, or for controlling spasticity, and for providing protection from such injury to the central nervous system, the method comprising administering to the mammal at least one pharmacologically active compound as the primary therapeutic agent, the pharmacologically active compound comprising two neurologically active groups, one neurologically active group comprising a first guanidino-containing moiety, and the second neurologically active group comprising an alkylated xanthine group and providing beta-agonist activity, the pharmacologically active compound thus providing a combination of neurological receptor activity designed to stimulate the appropriate alpha-adrenergic and beta-adrenergic receptors in the central nervous system and thus tonically stimulate motor neurons, in a mammal having a damaged central nervous system, the pharmacologically active compound being administered in a dosage amount and at a dosage rate sufficient to at least partially restore the lost neurological function or to control spasticity, the pharmacologically active compound being selected from the group consisting of the following compounds:

Guanidino-7-Acetyltheophylline,
2-Guanidinobenzimidazolyl-7-Acetyltheophylline,
3,4,5-Trimethoxybenzylidene-2-Hydrazinoimidazole,
2-Hydrazinoimidazolyl-7-Acetyltheophylline,
Theobromine-1-Acetyl Guanidine,
Theophylline-7-Acetylamidoguanidine,
Theobromine-1-Acetylamidoguanidine,
Theophylline-7-Acetyliminoguanidine,
2,4,6-Tris(7-Acetamidotheophylline)-1,3,5-s-Triazine,
2,4-Bis(2,6-Dicholorbenzylideneimino)-6-(7-Acetamidotheophylline)-1,3,5-s-Triazine,
2,4-Bis(1-Naphthylacetamido)-6(7-Acetamidotheophylline)-1,3,5-s-Triazine,
2,4-Bis(7-Acetamidotheophylline)-6-(2,6-Dichlorobenzylideneamino)-1,3,5-s-Triazine,
Theophylline-7-Ethyleneiminoguanidine,
2-(Theophylline-7-acetamido)-2-amino-benzimidazole,
2-Amino-4-(nicotinamido)-6-(theophylline-7-acetamido)-1,3,5-s-triazine, 2-(Amino)-4-(6-aminohexanamido)-6-theophylline-7-acetamido)-1,3,5-s-triazine,
2-(Amino)-4-(2-acetoxybenzamido)-6-(theophylline-7-acetamido)-1,3,5-s-triazine,
Theobromine-1-acetamido-guanidine,
2-(Amino)-4-(nicotinamido)-6(theobromine-1-acetamido)-1,3,5-s-triazine,
2-(Amino)-4-(2,6-dichlorophenyl-acetamido)-6-(theobromine-1-acetamido)-1,3,5-s-triazine,
2-(Amino)-4-(2,6-dichlorophenyl-acetamido)-6-(theobromine-1-acetamido)-1,3,5-s-triazine,
3,5-Dichloro-2-(theophylline-7-acetoxy)-benzylidineaminoguanidine
3-(2,3,6,7-Tetrahydro-3,7-dimethyl-2,6-dioxo-1(2H) purineacetamido)-1,2,4-triazine,
2-(Theophylline-7-acetamido)-2-methylbenzimidazole
4-(Amidino)-N-(theophylline-7-acetyl)-benzamide,
7-(3,5-Dichorophenylhydrazido)-7-acetyltheophylline,
7-(3,5-Dichorophenylhydrazido)-7-acetyltheophylline,
N,N'-Bis-(theophylline-7-acetyl)-guanidine,
N-(6-Hydroxy-2,5,7,8-tetramethylchroman-2-carbonyl)-N'-(theophylline-7-acetyl)-guanidine,
2-(4-Aminobutyramido)-4-(6-hydroxy-2,5,7,8-tetramethylchroman-2-carboxamido)-6-(theophylline-7-acetamido)-1,2,3-s-triazine,
6-(Methyl)-2-(4-theophylline-7-acetamido-phenyl)-2-benzothiazole,
6-(Theophylline-7-acetoxy)-2-5-7-8-tetramethylchroman-2-carboxamidoguanidine,
1-(Guanidinoacetoxy)-3-(theophylline-7-acetoxy)-2-propanol,
N-(2,6-Dichlorobenzylideneamino)-N'-(theophylline-7-acetyl)-guanidine,
3,7-Dihydro-8-(2,6-dichlorobenzylidene amino)-1,3,7-trimethyl-1H-purine-2,6-dione,
3,7-Dihydro-8-N-(2-acetoxybenzamido)-1,3,7-trimethyl-1H-purine-2,6-dione, 3-(2,6-Dichlorobenzylideneamino)-5-(theophylline-7-acetamido)-1,2,4-triazole,
3-(-2-Acetoxybenzamido)-5-(theophylline-acetamido)-1,2,4-triazole,
3-(-2-Guanidinoacetoxybenzamido)-5-(theophylline-7-acetamido)-1,2,4-triazole,
3,7-Dihydro-8-(2-guanidinoacetoxyphenyl-carboxamido)-1,3,7-trimethyl-1H-purine-2,6-dione,
3,7-Dihydro-8-(6-hydroxy-2,5,7,8-tetramethylchroman-2-carboxamido)-1,3,7-trimethyl-1H-purine-2,6-dione,
3,7-Dihydro-8-N-(-2-guanidinoacetoxy-2,5,7,8-tetramethylchroman-2-carboxamido)-1,3,7-trimethylxanthine,
3-(Glycylamido)-5-(theophylline-7-acetamido)-1,2,3-triazine
8-[2-(4-Amino-3,5-dichlorophenyl)-2-hydroxyethylene]-8-imino-1,3,7-trimethylxanthine,
8-[(2-Guanidinoacetoxyethyl methylamino)-caffeine,
8-(4-Aminobutyramido)-1,3,7-trimethyl-xanthine,
8-N-(5-Hydroxyindole-3-ethylamino)-8-(1,3,7-trimethyl)-xanthine,
7-(Guanidinoaminoethyl)-7-(1,3-dimethyl)-xanthine,
4-N-(8-Amino-1,3,7-trimethylxanthine)-4-butyric acid,
1-N-(Theophylline-8-amino)-1-amino-pthalazine,
2-(8-caffeineamino)-1,3,4-thiadiazole-2-N-(1,3,7-Trimethylxanthine-8-amino)-1,3,4-thiadiazole,
8-N-(10,11-Dihydro-5H-dibenzo[a,d]cycloheptene-5-carboxamido)-8-(1,3,7-trimethyl)-xanthine, and
3,5-Bis-(7-methyl-8-theophyllineamino)-1,2,4-triazole,
2-(Acetoxybenzamido)-4-(2,6-dichlorobenzylideneamino)-6-(theophylline-7-acetamido)-1,3,5-s-triazine;
2-(Amino)-4-(1-carboxamido-N,N,N-trimethylmethaniminium)-6-(theophylline-7-acetamido)-1,3,5-s-triazine;
2-Amino-4-(nicotinamido)-6-(theophylline-7-acetamido)-1,3,5-s-triazine;
2-(Amino)-4-(2-acetoxybenzamido)-6-(theophylline-7-acetamido)-1,3,5-s-triazine;
2-(2,6-Dichlorbenzylideneamino)-4-(3,5-dihydroxy-2-(R)-or-(S)-ethylimino)-6-(theophylline-7-acetamido)-1,3,5-s-triazine;
2-(Acetoxybenzamido)-4-(amino)-6-(1-naphthylacetamido)-1,3,5-s-triazine;
4-(Amidino)-N-(theophylline-7-acetyl)-benzamide;
N-(6-Hydroxy-2,5,7,8-tetramethylchroman-2-carbonyl)-N'-(theophylline-7-acetyl)-guanidine;
3,7-Dihydro-8-N-(2-acetoxybenzamido)-1,3,7-trimethyl-1H-purine-2,6-dione;
3-(2,6-Dichlorobenzylideneamino)-5-(theophylline-7-acetamido)-1,2,4-triazole;
3,7-Dihydro-8-(6-hydroxy-2,5,7,8-tetramethylchroman-2-carboxamido)-1,3,7-trimethyl-1H-purine-2,6-dione;
3-(Glycylamido)-5-(theophylline-7-acetamido)-1,2,3-triazine;
8-[2-(4-Amino-3,5-dichlorophenyl)-2-hydroxyethylene]-8-imino-1,3,7-trimethylxanthine
8-(4-Aminobutyramido)-1,3,7-trimethyl-xanthine;
8-N-(5-Hydroxyindole-3-ethylamino)-8-(1,3,7-trimethyl)-xanthine;
1-N-(Theophylline-8-amino)-1-amino-pthalazine;
8-N-(10,11-Dihydro-5H-dibenzo[a,d]cycloheptene-5-carboxamido)-8-(1,3,7-trimethyl)-xanthine;
3,5-Bis-(7-methyl-8-theophyllineamino)-1,2,4-triazole.

* * * * *